United States Patent
Lloyd et al.

(10) Patent No.: US 6,511,977 B1
(45) Date of Patent: Jan. 28, 2003

(54) POTASSIUM CHANNEL INHIBITORS AND METHOD

(75) Inventors: John Lloyd, Yardley, PA (US); Heather J. Finlay, Lawrenceville, NJ (US); Wayne Vaccaro, Yardley, PA (US); Karnail S. Atwal, Newtown, PA (US); Michael F. Gross, Durham, NC (US); Kerry L. Spear, Raleigh, NC (US)

(73) Assignee: Bristol-Myers Squibb Company, Princeton, NJ (US)

( * ) Notice: Subject to any disclaimer, the term of this patent is extended or adjusted under 35 U.S.C. 154(b) by 14 days.

(21) Appl. No.: 09/670,285

(22) Filed: Sep. 25, 2000

Related U.S. Application Data

(62) Division of application No. 09/375,955, filed on Aug. 17, 1999, now Pat. No. 6,150,356.
(60) Provisional application No. 60/098,709, filed on Sep. 1, 1998.

(51) Int. Cl.[7] ............... C07D 491/052; A61K 31/35
(52) U.S. Cl. ............... 514/233.8; 514/252.14; 514/252.18; 514/253.04; 514/302; 544/127; 544/331; 544/362; 546/115; 546/116
(58) Field of Search .................. 544/127, 331, 544/362; 546/115, 116; 514/233.8, 252.14, 252.18, 253.04, 302

(56) References Cited

U.S. PATENT DOCUMENTS

| | | | |
|---|---|---|---|
| 5,082,858 A | 1/1992 | Garcia et al. | 514/456 |
| 5,140,031 A | 8/1992 | Atwal et al. | 514/302 |
| 5,151,442 A | 9/1992 | Garcia et al. | 514/456 |
| 6,184,221 B1 * | 2/2001 | Gerlach et al. | 514/233.5 |

FOREIGN PATENT DOCUMENTS

| | | |
|---|---|---|
| EP | 389861 B1 | 8/1995 |
| EP | 807629 A1 | 11/1997 |
| WO | WO97/25983 | 7/1997 |
| WO | WO97/26300 | 7/1997 |
| WO | WO98/04521 | 2/1998 |
| WO | WO99/37607 | 7/1999 |

OTHER PUBLICATIONS

Lohrman et al., "A New Class Of Inhibitors . . . ", Pflugers Arch–Eur. J. Physiol. (1995) 429: 517–530.
Atwal et al., "Cardioselective Anti–Ischemic ATP–Sensitive Potassium Channel Openers", J. Med. Chem. (1993) vol. 36, 3971–3974.
Evans et al., "Short Efficient Synthesis Of 2,2–Dimethyl–2H–Pyranopyridines", Synthetic Communications, 18(10), 1111–1118 (1988).
Ding, "A Convenient Synthesis Of 6–Substituted–2, 2–Dimethyl–2H–1–Benzopyrans", Synthetic Communications, 26 (22),4267–4273 (1996).
Atwal et al., "A Facile Synthesis Of Cyanoguanidines From Thioureas", Tetrahedron Letters, vol. 30, 7313–7316 (1989).
Bargar et al., "3,4–Dihydro–2–phenyl–2H–pyranol[2,3–b] pyridines with Potent Antirhinovirus Activity", J. Med. Chem. (1986), 29, 1590–1595.

* cited by examiner

*Primary Examiner*—Deepak R. Rao
(74) *Attorney, Agent, or Firm*—Burton Rodney

(57) ABSTRACT

Indanes, benzopyrans and analogues thereof are potassium channel inhibitors and blockers of IKur and have the structure

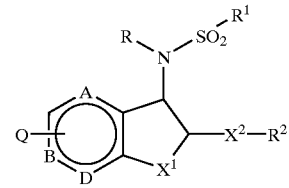

where A, B, D, Q, $X^1$, R, $R^1$, $X^2$ and $R^2$ are as defined herein. These compounds are useful as antiarrhythmic agents. In addition, a method is provided for preventing cardiac arrhythmia employing the above compounds.

11 Claims, No Drawings

POTASSIUM CHANNEL INHIBITORS AND METHOD

This is a division of U.S. application Ser. No. 09/375,955 filed Aug. 17, 1999 now U.S. Pat. No. 6,150,356, which claims priority from U.S. application Ser. No. 60/098,709 filed Sep. 1, 1998.

FIELD OF THE INVENTION

The present invention relates to indanes and benzopyrans and analogues thereof which are potassium channel inhibitors and thus are useful as antiarrhythmic agents.

BRIEF DESCRIPTION OF THE INVENTION

In accordance with the present invention, novel indanes and benzopyrans and analogues thereof are provided which are potassium channel inhibitors and have the structure

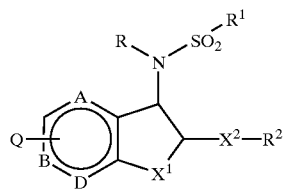

including pharmaceutically acceptable salts thereof, prodrug esters thereof, and all stereoisomers thereof, wherein A, B and D are independently selected from CH or N;
$X^1$ is

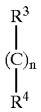

(where n is 1, 2 or 3), O, $NR^5$, S, SO, $SO_2$,

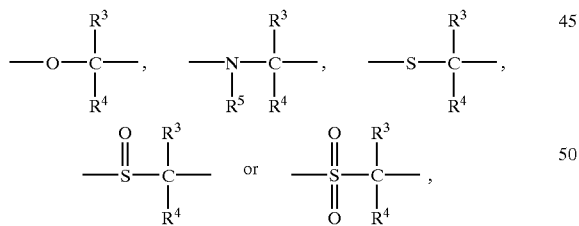

wherein the hetero atom in each of the above groups is linked to the aromatic ring;
(where $R^3$ and $R^4$ are independently H, alkyl, arylalkyl or cycloalkyl, or $R^3$ and $R^4$ can be taken together with the carbon to which they are attached to form a 5 to 8 carbon containing ring; and $R^5$ is H, alkyl, alkenyl, aryl, arylalkyl, cycloalkyl or cycloalkylalkyl);
R is H, alkyl, alkenyl, aryl, arylalkyl, cycloalkyl, heterocycloalkyl, or cycloalkylalkyl;
$R^1$ is alkyl, arylalkyl, aryl, alkenyl, heterocyclo, heterocycloalkyl,

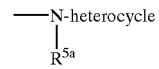

(where $R^{5a}$ can be any of the $R^5$ groups), cycloalkyl, cycloalkylalkyl or

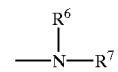

(where $R^6$ and $R^7$ are independently selected from H, aryl, alkyl, arylalkyl or cycloalkyl, or $R^6$ and $R^7$ can be taken together with the nitrogen atom to which they are attached to form a 5 to 8 membered ring); or R and $R^1$ can be taken together with the —N—S— atoms to form a 5- to 8-membered ring;
$X^2$ is a single bond,

or —O— (where $R^8$ is H, alkyl, alkenyl, aryl, arylalkyl, cycloalkyl or cycloalkylalkyl);
$R^2$ is H, alkyl, arylalkyl,

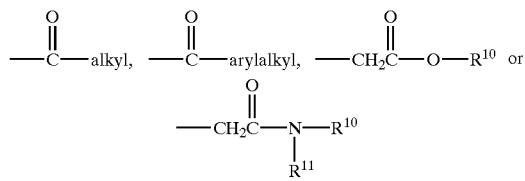

(where $R^{10}$ and $R^{11}$ are independently selected from H, alkyl, arylalkyl or cycloalkyl, or $R^{10}$ and $R^{11}$ can be taken together with the nitrogen to which they are attached to form a 5- to 8-membered ring); and Q is 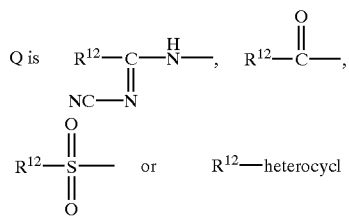

(where $R^{12}$ is alkyl, arylalkyl, aryl,

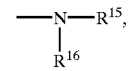

heterocycle, heterocycloalkyl,

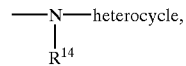

(where $R^{14}$ can be any of the $R^8$ groups), alkoxy, $CF_3$, aryloxy, arylalkoxy, cycloalkyl or cycloalkylalkyl, and where $R^{15}$ and $R^{16}$ are independently selected from H, alkyl, arylalkyl, aryl, heterocyclo, cycloalkyl, amino, aminoalkyl, or heterocycloalkyl, or $R^{15}$ and $R^{16}$ can be taken together with the nitrogen to which they are attached to form a 5- to 8-membered ring which may optionally contain an additional nitrogen atom in the ring and/or an amino group or an aminoalkyl group attached to the ring); and $R^{13}$ is

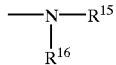

(wherein this moiety is as defined with respect to $R^{12}$);

with the proviso that where $X^1$ is

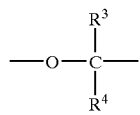

and A, B and D are all carbon, then (1) where Q is

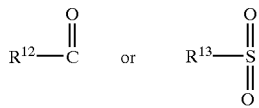

and $R^{12}$ or $R^{13}$ is

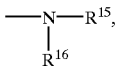

at least one of $R^{15}$ or $R^{16}$ is, aryl, arylalkyl, heterocycle or heterocycloalkyl, or alkyl of 4 to 12 carbons; and/or (2) Q is other than

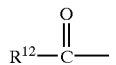

(where $R^{12}$ is methyl, ethyl, $CF_3$ or alkoxy); and/or (3) where Q is

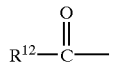

and $R^{12}$ is

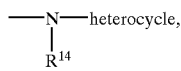

then heterocycle is a monocyclic or bicyclic heterocycle ring containing from 5 to 10 ring members, containing one to five nitrogen atoms, and/or one or two oxygen atoms, and/or one sulfur atom; and/or (4) where Q is

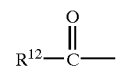

and $R^{12}$ is

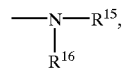

then at least one of $R^{15}$ and $R^{16}$ contains an additional amino group or $R^{15}$ and $R^{16}$ taken together with the nitrogen atom to which they are attached form a ring which contains an additional nitrogen atom in the ring and/or an amino group or an aminoalkyl group attached to the ring; and/or (5) where Q is

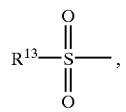

and $R^{13}$ is

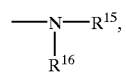

then at least one of $R^{15}$ and $R^{16}$ contains an additional amino group or $R^{15}$ and $R^{16}$ taken together with the nitrogen atom to which they are attached form a ring which contains an additional nitrogen atom in the ring and/or an amino group or an aminoalkyl group attached to the ring.

Preferred compounds of formula I of the invention can have the following structural formulae:

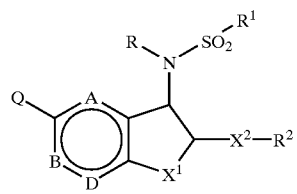

Ia

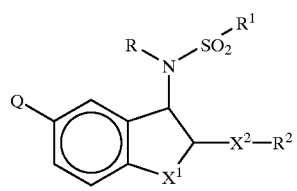

Ib

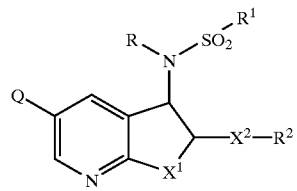

Ic

-continued

[Structure Ic: pyridine-fused with N in ring, Q substituent, R-N(SO₂R¹), X¹, X²-R²]

[Structure Id: pyridine-fused (N position different), Q, R-N(SO₂R¹), X¹, X²-R²]

[Structure Ie: pyrimidine-fused, Q, R-N(SO₂R¹), X¹, X²-R²]

Preferred are compounds of formula I wherein Q is $$\underset{R^{16}}{\overset{R^{15}}{N}}-\overset{O}{\underset{}{C}}- \quad \text{or} \quad \text{heterocycle-}\underset{R^{14}}{N}-\overset{O}{\underset{}{C}}-$$

wherein heterocycle is a monocyclic ring (cycloheteroalkyl ring or heteroaryl ring) containing 5 or 6 ring members which include one or two nitrogen atoms in the ring and/or one oxygen atom in the ring.

Also preferred are compounds of formula I where
R is H;
$R^1$ is aryl or alkyl;
$X^2$ is O or a single bond;
$R^2$ is H;
$X^1$ is $$-O-\underset{R^4}{\overset{R^3}{C}}-, \quad -\underset{H}{N}-\underset{R^4}{\overset{R^3}{C}}- \quad \text{or} \quad -\underset{R^4}{\overset{R^3}{C}}-$$

where $R^3$ and $R^4$ are each H and/or alkyl;
A and B are each CH;
D is N or CH; and
Q is $$-\overset{O}{\underset{}{C}}-\underset{R^{16}}{N}-R^{15} \quad \text{or} \quad -SO_2-\underset{R^{16}}{N}-R^{15}$$

where $R^{15}$ and $R^{16}$ are H, aryl, aralkyl or aminoalkyl. Still more preferred are compounds of formula I where
R is H;
$R^1$ is aryl;
$X^2$ is O or a single bond;
$R^2$ is H;
$X^1$ is $$-O-\underset{CH_3}{\overset{CH_3}{C}}-, \quad -\underset{H}{N}-\underset{CH_3}{\overset{CH_3}{C}}- \quad \text{or} \quad -\underset{R^4}{\overset{R^3}{C}}-;$$

A and B are each CH;
D is N or CH; and
Q is $$-\overset{O}{\underset{}{C}}-\underset{R^{16}}{N}-R^{15} \quad \text{or} \quad -SO_2-\underset{R^{16}}{N}-R^{15}.$$

In addition, in accordance with the present invention, a method for preventing, inhibiting or treating cardiac arrhythmia, including atrial arrhythmia, is provided, wherein a compound of formula I is administered in a therapeutically effective amount which inhibits the IKur potassium channel.

The formula I compound employed in the above method has the structure

IA

[Structure IA: aromatic ring with positions A, B, D, Q substituent, R-N(SO₂R¹), X¹, X²-R²]

including pharmaceutically acceptable salts thereof, prodrug esters thereof, and all stereoisomers thereof, wherein
A, B and D are independently selected from CH or N;
$X^1$ is $$\underset{R^4}{\overset{R^3}{\underset{|}{(C)_n}}}$$

(where n is 1, 2 or 3), O, $NR^5$, S, SO, $SO_2$, $$-O-\underset{R^4}{\overset{R^3}{C}}-, \quad -\underset{R^5}{N}-\underset{R^4}{\overset{R^3}{C}}-, \quad -S-\underset{R^4}{\overset{R^3}{C}}-,$$

$$-\overset{O}{\underset{}{S}}-\underset{R^4}{\overset{R^3}{C}}- \quad \text{or} \quad -\underset{O}{\overset{O}{\underset{}{S}}}-\underset{R^4}{\overset{R^3}{C}}-,$$

wherein the heteroatom in each of the above groups is linked to the aromatic ring;
(where $R^3$ and $R^4$ are independently H, alkyl, arylalkyl or cycloalkyl, or $R^3$ and $R^4$ can be taken together with the carbon to which they are attached to form a 5 to 8 carbon containing ring; and $R^5$ is H, alkyl, alkenyl, aryl, arylalkyl, cycloalkyl or cycloalkylalkyl);

R is H, alkyl, alkenyl, aryl, arylalkyl, heterocycloalkyl, cycloalkyl, or cycloalkylalkyl;

$R^1$ is alkyl, arylalkyl, aryl, alkenyl, heterocyclo, heterocycloalkyl,

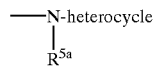

(where $R^{5a}$ can be any of the $R^5$ groups), cycloalkyl, cycloalkylalkyl or

(where $R^6$ and $R^7$ are independently selected from H, aryl, alkyl, arylalkyl or cycloalkyl, or $R^6$ and $R^7$ can be taken together with the nitrogen atom to which they are attached to form a 5 to 8 membered ring); or R and $R^1$ can be taken together with the —N—S— atoms to form a 5- to 8-membered ring;

$X^2$ is a bond,

or —O—

(where $R^8$ is H, alkyl, alkenyl, aryl, arylalkyl, cycloalkyl or cycloalkylalkyl);

$R^2$ is H, alkyl, arylalkyl,

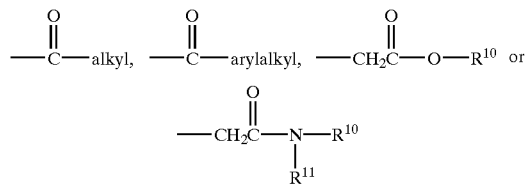

(where $R^{10}$ and $R^{11}$ are independently selected from H, alkyl, arylalkyl or cycloalkyl, or $R^{10}$ and $R^{11}$ can be taken together with the nitrogen to which they are attached to form a 5- to 8-membered ring); and Q is

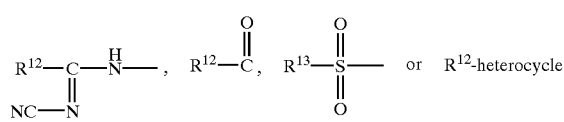

(where $R^{12}$ is alkyl, arylalkyl, aryl,

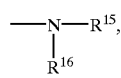

heterocycle, heterocycloalkyl,

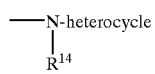

where $R^{14}$ can be any of the $R^8$ groups), alkoxy, aryloxy, arylalkoxy, cycloalkyl or cycloalkylalkyl, and where $R^{15}$ and $R^{16}$ are independently selected from H, alkyl, arylalkyl, heterocyclo, cycloalkyl or heterocycloalkyl, or $R^{15}$ and $R^{16}$ can be taken together with the nitrogen to which they are attached to form a 5- to 8-membered ring (which may optionally contain an additional nitrogen in the ring and/or an amino group or an aminoalkyl group attached to the ring); and $R^{13}$ is

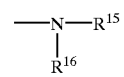

(wherein this moiety is as defined with respect to $R^{12}$).

DETAILED DESCRIPTION OF THE INVENTION

The following definitions apply to the terms as used throughout this specification, unless otherwise limited in specific instances.

Unless otherwise indicated, the term "lower alkyl", "alkyl" or "alk" as employed herein alone or as part of another group includes both straight and branched chain hydrocarbons, containing 1 to 40 carbons, preferably 1 to carbons, more preferably 1 to 12 carbons, in the normal chain,such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various additional branched chain isomers thereof, and the like as well as such groups including 1 to 4 substituents which may be halogen, haloalkyl, alkyl, alkoxy, alkenyl, alkynyl, aryl, arylalkyl, cycloalkyl, cycloalkenyl, amino, hydroxy, heteroaryl, cycloheteroalkyl, alkanoylamino, alkylamido, arylcarbonylamino, acyl, nitro, cyano, thiol, alkylthio or any of the alkyl or aryl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons, forming the ring and which may be fused to one aromatic ring as described for aryl, which include cyclopropyl, cyclobutyl, cyclopentyl, cyclohexyl, cycloheptyl, cyclooctyl, cyclodecyl and cyclododecyl, cyclohexenyl,

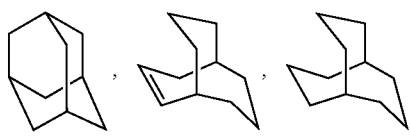

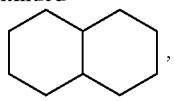

any of which groups may be optionally substituted with 1 to 4 substituents which may be any of the alkyl or aryl substituents set out herein.

The term "cycloalkenyl" as employed herein alone or as part of another group refers to cyclic hydrocarbons containing 5 to 20 carbons, preferably 6 to 12 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings) and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl.

The term "aralkyl", "aryl-alkyl" or "aryllower alkyl" as used herein alone or as part.of another group refers to alkyl groups as discussed above having an aryl substituent, such as benzyl or phenethyl, or naphthylpropyl, oran aryl as defined above.

The term "lower alkoxy", "alkoxy", "aryloxy" or "aralkoxy" as employed herein alone or as part of another group includes any of the above alkyl, aralkyl or aryl groups linked to an oxygen atom.

The term "amino" as employed herein alone or as part of another group may optionally be independently substituted with one or two substituents, which may be the same or different, such asalkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid or any of the alkyl or aryl substituents set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-l-piperazinyl, 4-arylalkyl-l-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

The term "lower alkylthio", "alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group, as defined herein, refers to an organic radical linked to a carbonyl

group; examples of acyl groups include any of the $R^1$ groups attached to a carbonyl, such as alkanoyl, alkenoyl, aroyl, aralkanoyl, heteroaroyl, cycloalkanoyl, cycloheteroalkanoyl and the like.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to carbons, preferably 3 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, cycloalkenyl, amino, hydroxy, heteroaryl, cycloheteroalkyl, alkanoylamino, alkylamido, arylcarbonylamino, acyl, nitro, cyano, thiol, alkylthio or any of the alkyl or aryl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one 20 triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, or any of the alkyl or aryl substituents set out herein.

Where alkyl groups as defined above have single bonds for attachment to other groups at,two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

Suitable alkylene, alkenylene or alkynylene groups $(CH_2)_p$ (where p is 1 to 8, preferably 1 to 5) (which may include alkylene, alkenylene or alkynylene groups) as defined herein, may optionally include 1, 2, or 3 substituents which include any of the alkyl or aryl substituents set out herein.

Examples of alkylene, alkenylene and alkynylene

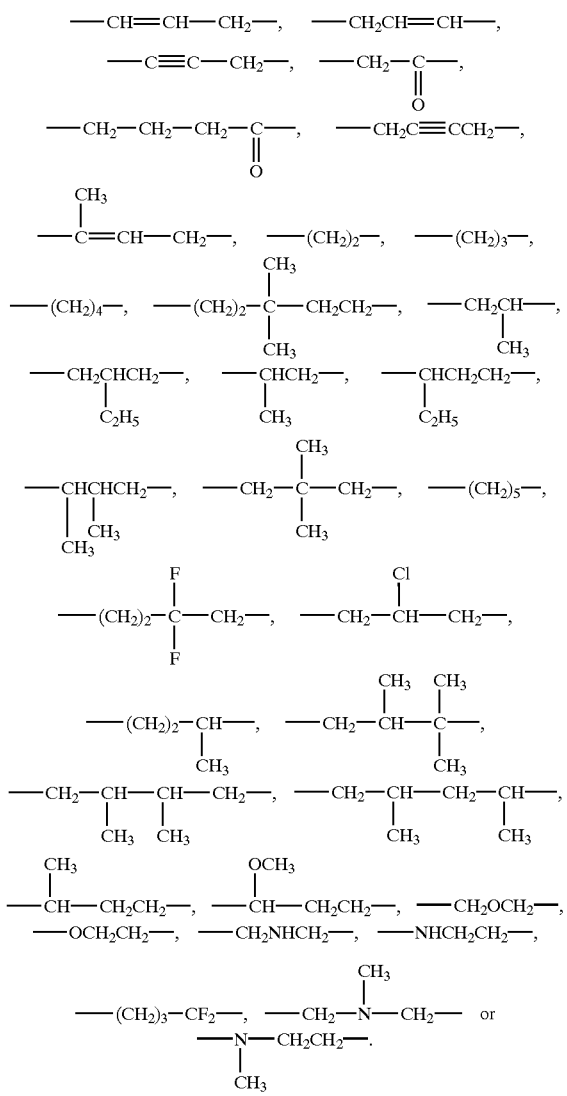

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "heterocycle" or "heterocyclo" as used herein alone or as part of another group refers to a "cycloheteroalkyl" group or a "heteroaryl" group as defined hereinafter.

The term "heterocycloalkyl", as used herein alone or as part of another group refers to a heterocycle linked through a carbon to an alkyl group.

The term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

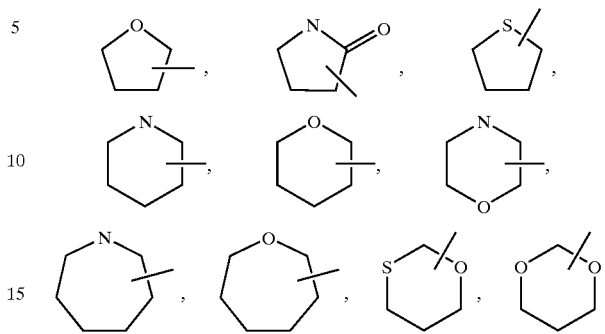

and the like. The above groups may include 1 to 4 substituents such as alkyl, halo, oxo and/or any of the alkyl or aryl substituents set out herein. In addition, any of the above rings can be fused to a cycloalkyl, aryl, heteroaryl or cycloheteroalkyl ring.

The term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the alkyl or aryl substituents set out above. Examples of heteroaryl groups include the following:

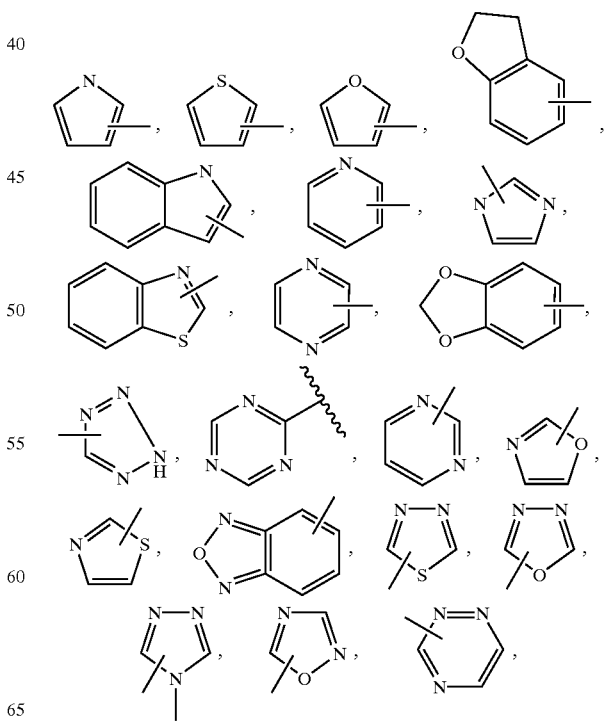

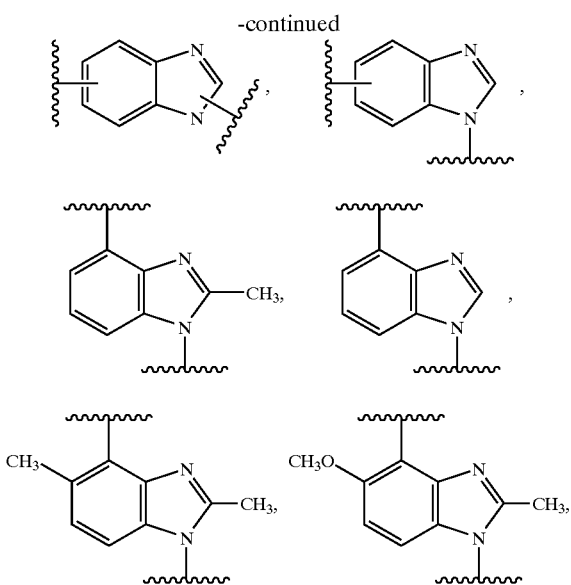

and the like.

The term "cycloheteroalkylalkyl" as used herein alone or as part of another gorup refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a —$(CH_2)_p$— chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo 20 substituents, such as F or Cl, preferably F, such as $CF_3CH_2O$, $CF_3O$ or $CF_3CF_2CH_2O$.

The compounds of formula I can be present as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or such as ($C_1$–$C_4$)-alkyl- or aryl-sulfonic acids which are unsubstituted or substituted, for example by halogen, for example methane- or p-toluene-sulfonic acid. Corresponding acid addition salts can also be formed having, if desired, an additionally present basic center. The compounds of formula I having at least one acid group (for example COOH) can also form salts with bases.

Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

A preferred salt of the compounds of formula I is the monohydrochloride salt.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

It should be understood that the present invention includes prodrug forms of the compounds of formula I such as alkylesters of acids or any of the prodrugs disclosed in "Prodrugs", D. G. Wailer, C. F. George, Br. J. Clin. Pharmac. (1989), 28, 497–507; "Prodrugs for the improvement of drug absorption via different routes of administration", L. P. Balant, E. Doelker, P. Burt, Eur. J. Drug Metab. Pharmacokinet. (1990), 15, 143–153; "Prodrugs as a means to improve the delivery of peptide drugs", H. Bundgaard, Advanced Drug Delivery Reviews (1992), 8, 1–38; "Novel chemical approaches in prodrug design" (1991), Drugs of the Future, 16, 443–458; and in U.S. application Ser. No. 08/641,718, filed May 2, 1996, and in U.S. Pat. No. 5,561, 146 which are incorporated herein by reference.

The compounds of the instant invention may, for example, be in the free or hydrate form, and may be obtained by methods exemplified by the following descriptions.

The compounds of formula I may be prepared by the exemplary processes described in the following reaction schemes. Exemplary reagents and procedures for these reactions appear hereinafter and in the working Examples.

Compounds of formula I of the invention can be repared by using the sequence of steps outlined in General chemes 1 to 8 set out below.

General Scheme 1

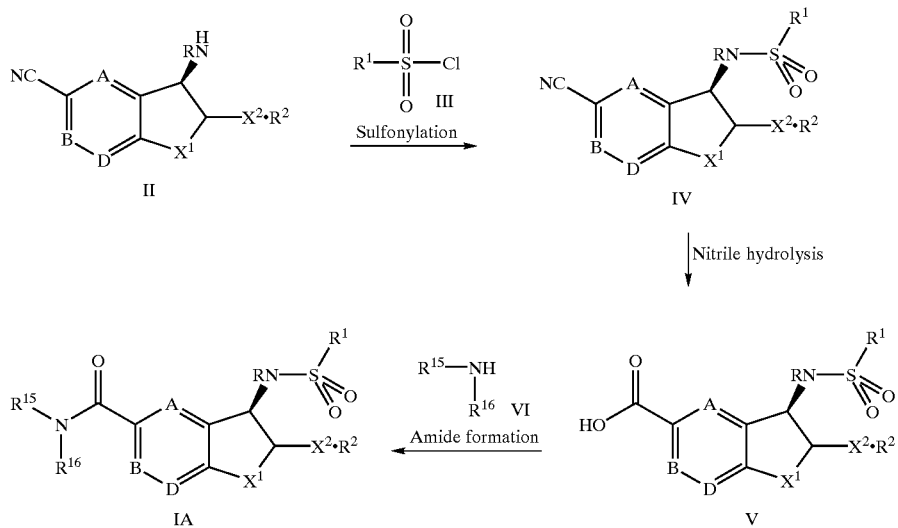

Referring to General Scheme 1, amide compounds of the invention of formula IA may be prepared starting with nitrie II which is made to undergo a sulfonylation by reacting II with a sulfonylating agent III (employing a molar ratio of III:II within the range from about 1:1 to about 10:1) in the presence of a base such as triethylamine or duisopropylethylamine in an inert organic solvent such as acetonitrile and/or dichioromethane, to form sulfonylated compound IV.

Comnpound IV is then subjected to nitrile hydrolysis by treating an aqueous solution of IV with sodium peroxide and then with strong acid such as hydrochloric acid, to form the acid V.

Acid V is treated with amine VI (employing a molar of VI:V within the range from about 1:1 to about 10:1) and a dehydrating agent such as 1-(3-dimethylaminopropyl)-3-ethylcarboiimide with 4-dimethylaminopyeidine in the presence of an inert solvent such as acetonitrile and/or dimethylformamide, to form amide compounds of the invention IA.

The starting nitrile II in General Scheme 1 may be prepared as described in K. Atwal et al, J. Med. Chem. (1993) 36, 3971–3974 and references cited therein.

General Scheme 2

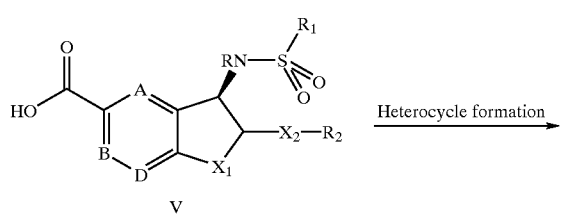

-continued

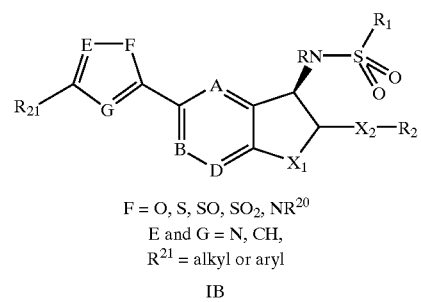

F = O, S, SO, SO$_2$, NR$^{20}$
E and G = N, CH,
R$^{21}$ = alkyl or aryl

IB

Referring to General Scheme 2, compounds of the invention of formula IB may be prepared from acid V employing methods known in the literature and described in "Comprehensive Heterocyclic Chemistry", A. Katritsky et al, Pergamon, Elsevier Science, Inc., (1996).

Where F is oxygen and E and G are nitrogen, compound IB may be prepared by reaction of the acid V with a hydroxyamidine in the presence of a dehydrating agent such as (benzotriazol-1-yloxy.)tripyrrolidinophosphonium hexafluorophosphate (P$_y$BOP) and a tertiary amine such as triethylamine in an inert organic solvent such as dichloromethane. The resulting acylhydroxyamidine can be treated with a base such as potassium, sodium or cesium carbonate in an inert organic solvent such as tetrahydrofuran to provide compound IB.

General Scheme 3

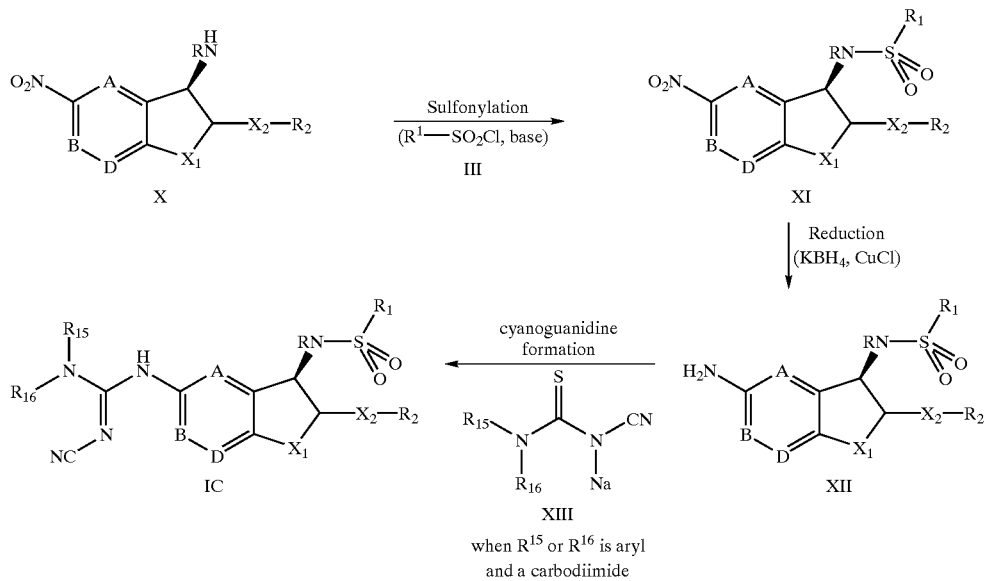

Referring to General Scheme 3, compounds of the invention of formula IC where either $R^{15}$ or $R^{16}$ is aryl may be prepared starting with compound X which is made to undergo sulfonylation by reacting nitro compound X with sulfonylating agent III (employing a molar ratio of III:X within the range from about 1:1 to about 10:1) in the presence of a base such as triethylamine and an inert organic solvent such as dichloromethane to form sulfonylated compound XI.

Compound XI is reduced, for example, by reacting XI with $KBH_4$ in the presence of CuCl to form aniline XII. Aniline XII is then subjected to cyanoguanidine formation by reacting XII with an N-cyanothiourea sodium salt XIII (employing a molar ratio of XIII:XII within the range from about 1:1 to about 5:1) in the presence of a carbodiimide such as 1-(3-dimethylaminopropyl)-3-ethylcarbodiimide and an inert organic solvent such as anhydrous dimethylformamide, dichloromethane or acetonitrile to form cyanoguanidine of the invention IC.

The starting nitro compound X may be prepared following procedures as described in WO9804521.

The sodium salt of a cyanothiourea XIII may be prepared from the corresponding isothiocyanate and cyanamide as described in Atwal, K. S.; Ahmed, S. Z., O'Reilly, B. O. Tetrahedron Letters (1989) 30, 7313.

General Scheme 4

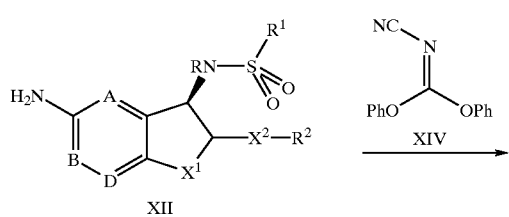

-continued

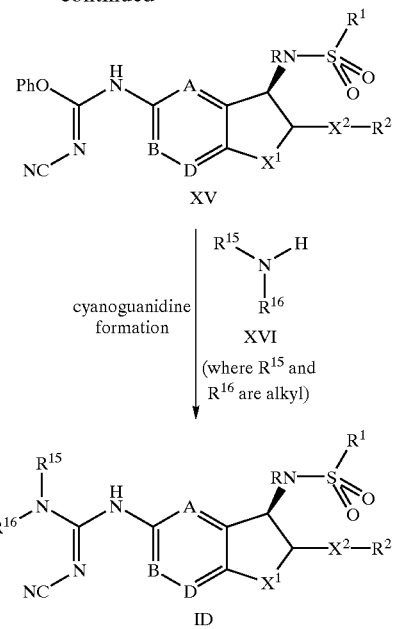

Referring to General Scheme 4, compounds of the invention of formula ID where $R^{15}$ and $R^{16}$ are alkyl may be prepared starting with aniline compound XII which is reacted with diphenyl cyanocarbonimidate XIV (employing a molar ratio of XIV:XII within the range from about 1:1 to about 5:1) in an inert organic solvent such as acetonitrile under reflux conditions to form cyanoimidate XV.

Cyanoimidate XV is then reacted with amine XVI (employing a molar ratio of XVI:XV within the range from about 1:1 to about 5:1) in the presence of inert organic solvents such as isopropanol and dimethylsulfoxide to form cyanoguanidine compound of the invention ID.

General Scheme 5

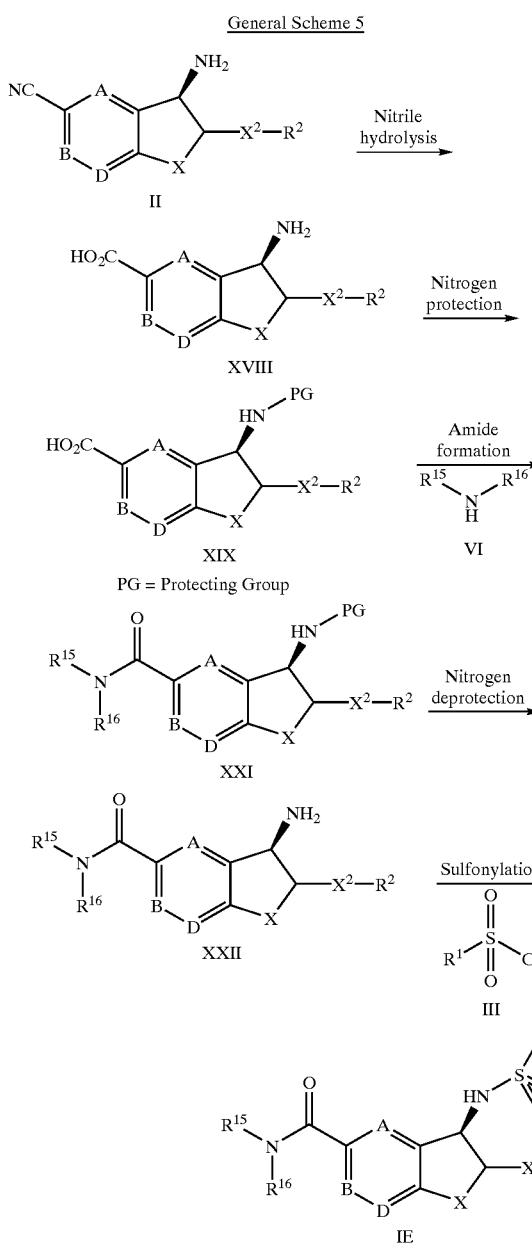

PG = Protecting Group

General Scheme 6

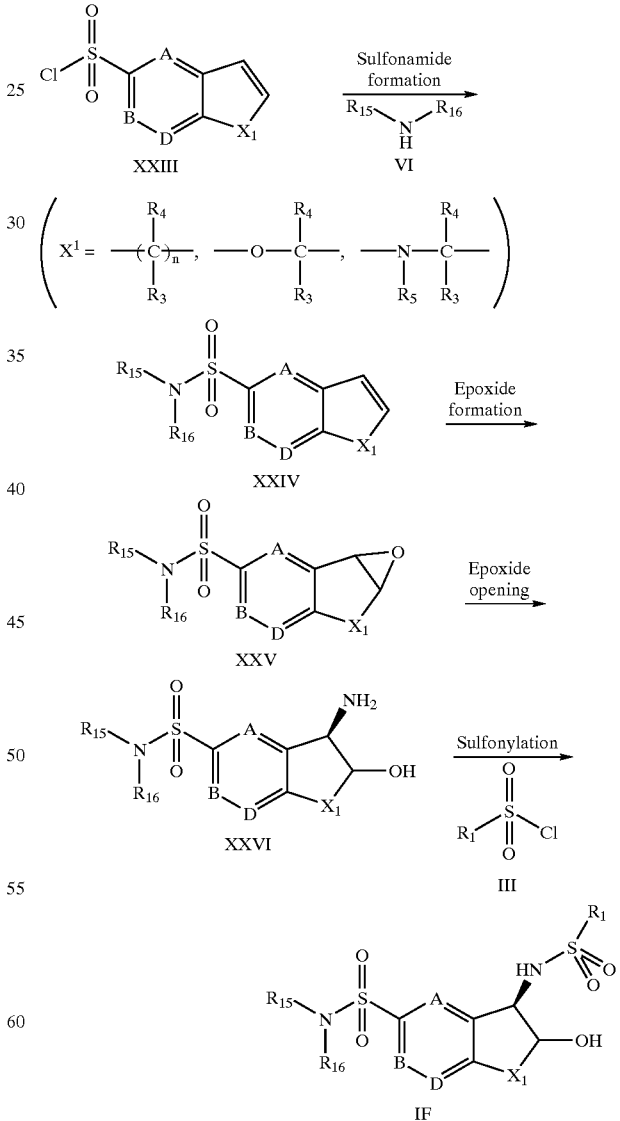

Referring to General Scheme 5, compounds of the invention of the formula IE may be prepared by starting with nitrile II which is made to undergo nitrile hydrolysis with concentrated aqueous acid such as hydrochloric, hydrobromic or sulfuric acid to form the amino acid XVIII.

The amino acid XVIII may be protected using an amine protecting reagent such as di-t-butyldicarbonate (or other suitable reagents described in Theodora Greene, Peter Wuts "Protective Groups in Organic Synthesis" 2nd Ed. Wiley-Interscience, 1991) in water with an organic cosolvent such as t-butanol and, a water soluble base such as sodium hydroxide or sodium bicarbonate to give the acid XIX.

The acid XIX is treated with amine VI (employing a molar ratio of XIX:VI within the range from about 1:1 to about 1:10) and a dehydrating agent such as 1-(3-dimethylaminopropyl)-3-ethyl carbodiimide and or bromo-tris-pyrrolidinophosphonium hexafluorophosphate in the presence of an organic base.such as N,N-diisopropylethylamine or triethylamine in an inert solvent such as acetonitrile and/or dimethylformamide to form the amide XXI.

The amide XXI may be deprotected using the reagent appropriate for the protecting group used, for example, hydrogen chloride in an inert organic solvent such as dioxane, methanol or ethyl acetate for removal of the t-butyloxycarbonyl group, to form the amine XXII.

The amine XXII may be sulfonylated by reaction with a sulfonylating agent III (employing a molar ratio of XXII:III within the range from about 1:1 to about 1:10) in the presence of an organic base such as N,N-diisopropylethylamine or triethylamine in an inert organic solvent such as acetonitrile, N,N-dimethylformamide, dichloromethane or dichloroethane to form compounds of the invention IE.

The starting nitrile II in General Scheme 5 can be prepared as described in the references cited in General Scheme 1.

Referring to General Scheme 6, compounds of the invention IF may be prepared starting from the sulfonyl chloride XXIII which may be reacted with an amine VI (employing a molar ratio of XXIII:VI within the range from about 1:1 to about 1:10) in the presence of an organic base such as N,N-diisopropylethylamine or triethylamine in an inert organic solvent such as acetonitrile, N,N-dimethylformamide, dichloromethane or dichloroethane to form compounds of the formula XXIV.

The sulfonamide XXIV may be epoxidized using an epoxidizing agent such as m-chloroperbenzoic acid or dimethyldioxirane in an inert organic solvent such as dichloromethane or acetone to form the epoxide XXV.

The epoxide XXV may be opened by reaction with concentrated aqueous ammonia either neat or with an organic cosolvent such as methanol or ethanol to form the aminoalcohol XXVI.

The aminoalcohol XXVI may be sulfonylated by reaction with a sulfonylating agent III (employing a molar ratio of XXVI:III within the range from about 1:1 to about 1:10) in the presence of an organic base such as N,N-diisopropylethylamine or triethylamine in an inert organic solvent such as acetonitrile, N,N-dimethylformamide, dichloromethane or dichloroethane to form compounds of the invention IF.

An example of a sulfonyl chloride XXII in General Scheme 6 can be prepared as described in Ding, CZ. Synthetic Comm. 1996, 26, 4267–4273.

General Scheme 7

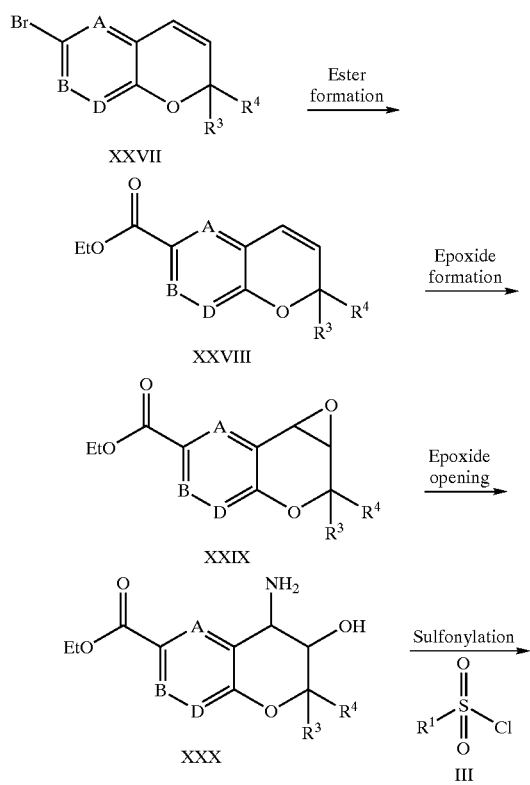

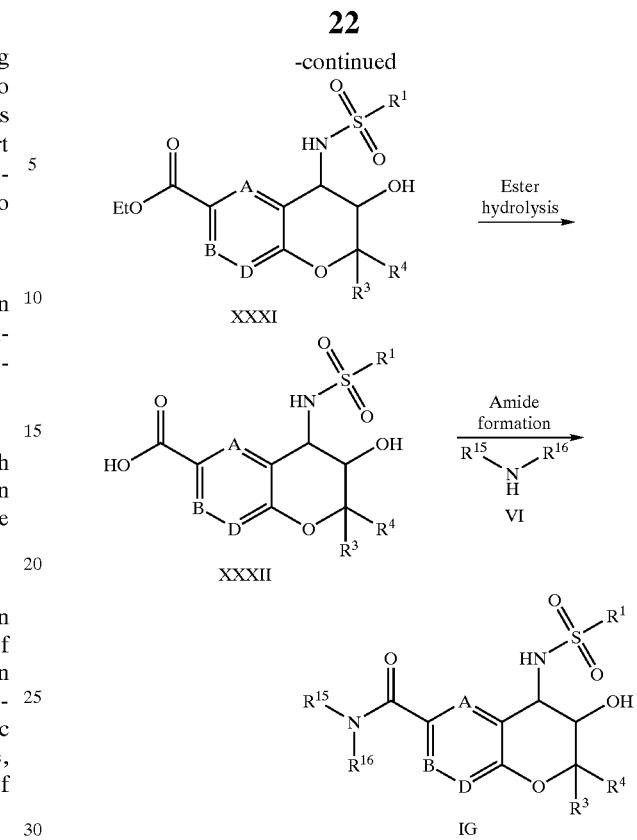

Referring to General Scheme 7, compounds of the invention of formula IG may be prepared starting from bromide XXVII which may be metallated with t-butyllithium in an inert organic solvent such as tetrahydrofuran and the anion reacted with an acylating agent such as ethylchloroformate to form the ester XXVIII.

The ester XXVIII may react with epoxide forming reagents such as N-bromosuccinimide followed by base treatment, m-chloroperbenzoic acid, or dimethyldioxirane to form the epoxide XXIX.

The epoxide XXIX may be opened by reaction with concentrated aqueous ammonia either neat or with an organic cosolvent such as methanol or ethanol to form the aminoalcohol XXX.

The aminoalcohol XXX may be sulfonylated by reaction with a sulfonylating agent III (employing a molar ratio of XXXII:III within the range from about 1:1 to about 1:10) in the presence of an organic base such as N,N-diisopropylethylamine or triethylamine in an inert organic solvent such as acetonitrile, N,N-dimethylformamide, dichloromethane or dichloroethane to form the sulfonamide XXXI.

The ester in compound XXXI may be hydrolyzed using a base such as potassium hydroxide, sodium hydroxide or lithium hydroxide in aqueous solution or in water with an organic cosolvent such as methanol, ethanol, ethylene glycol or dioxane to form the acid XXXII.

The acid XXXII may be treated with amine VI (employing a molar ratio of XIX:VI within the range from about 1:1 to about 1:10) and a dehydrating agent such as 1-(3-dimethylaminopropyl)-3-ethyl carbodiimide and or bromo-tris-pyrrolidinophosphonium hexafluorophosphate in the presence of an organic base such as N,N-diisopropylethylamine or triethylamine in an inert solvent such as acetonitrile and/or dimethylformamide to form compounds of the invention IG.

An example of a bromide XXVII in General Scheme 7 where A and B are CH and D is N can be prepared as described in Barger, T. M.; Dulworth, J. K.; Kenny, M. T.; Massad, R.; Daniel, J. K.; Wilson,T.; Sargent, R. N.; *J. Med. Chem.*, 1986, 29, 1590 and Evans, J. M.; Stemp, G.; *Syn. Comm.*, 1988, 18, 1111.

General Scheme 8

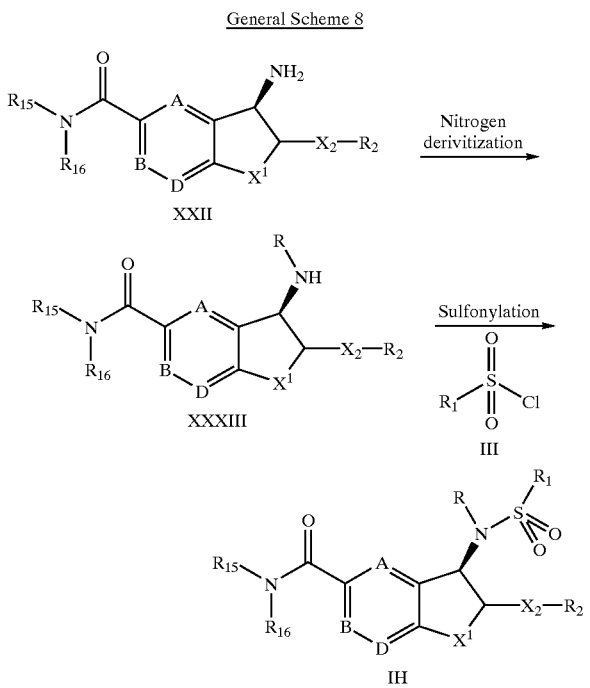

Referring to General Scheme 8, compounds of the invention IH may be prepared from the amine XXII by derivatization of the amine using an alkylating agent such as an alkyl halide or by reductive alkylation using an aldehyde and a suitable reducing agent such as sodium cyanoborohydride, sodium triacetoxyborohydride or borane-pyridine complex in an organic solvent such as methanol, ethanol or acetic acid to form the amine compound XXXIII.

The amine compound XXXIII may be sulfonylated by reaction with a sulfonylating agent III (employing a molar ratio of XXXIII:III within the range from about 1:1 to about 1:10) in the presence of an organic base such as N,N-diisokropylethylamine or triethylamine in inert organic solvent such as acetonitrile, N,N-dimethylformamide, dichloromethane or dichloroethane to form compounds of the invention IH. HA721a Amine compounds XXII in General Scheme 8 have previously been described in General Scheme 5.

In the above Schemes, although the Q moiety is fixed at a definite position in the aromatic ring, it will be understood that the Q moiety may be attached at any appropriate position on the aromatic ring.

The compounds of formula I of the invention exhibit potassium channel inhibitory activity. They are blockers of the delayed rectifier voltage-gated potassium channel termed IKur which has been reported to contain the voltage gated potassium channel Kv 1.5 α-subunit gene product. This gene product is believed to be important in the repolarization of the human atrial action potential. The compounds of the invention are useful in the treatment of cardiac arrhythmia especially those occurring in the atria as well as in cell proliferative disorders, such as leukemia and autoimmune diseases such as rheumatoid arthritis and transplant rejection.

Thus, compounds of formula I of the invention may be used as antiarrhythmic agents, i.e., for the treatment of arrhythmia including atrial arrhythmia. Thus, a composition containing one (or a combination) of the compounds of this invention, may be administered to a species of mammal (e.g., humans, dogs or cats) suffering from an arrhythmic condition.

A single dose, or two to four divided daily doses, provided on a basis of about 0.001 to about 100 mg per kilogram of body weight per day, preferably about 0.1 to about 25 mg per kilogram of body weight per day is appropriate. The substance is preferably administered orally, but parenteral routes such as the subcutaneous, intramuscular, intravenous or intraperitoneal routes or any other suitable delivery system, such as intranasal or transdermal routes can also be employed.

The compounds of this invention can also be formulated in combination with a cyclooxygenase inhibitor such as aspirin or indomethacin, a platelet aggregation inhibitor such as clopidogrel, ticlopidene or aspirin, fibrinogen antagonists or a diuretic such as chlorothiazide, hydrochlorothiazide, flumethiazide, hydroflumethiazide, bendroflumethiazide, methylchlorthiazide, trichloromethiazide, polythiazide or benzthiazide as well as ethacrynic acid tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, angiotensin II antagonists such as losartan, irbesartan or valsartan, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or animal salivary gland plasminogen activators, calcium channel blocking agents such as verapamil, nifedipine or diltiazem, thromboxane receptor antagonists such as ifetroban, prostacyclin mimetics, or phosphodiesterase inhibitors. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to about 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the invention and are of preferred embodiments of the invention, which include compounds of the invention and compounds employed in the method of the invention. It should be understood that there may be other embodiments which fall within the spirit and scope of the invention as defined by the claims appended hereto.

EXAMPLE 1

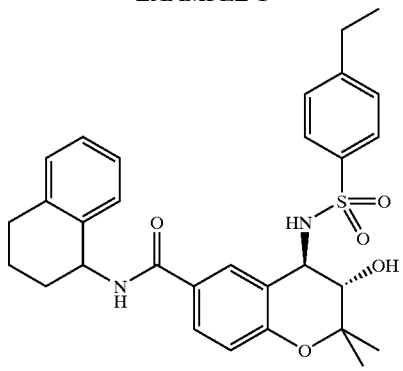

trans-4-Amino-3,4-dihydro-2,2-dimethyl-6-cyano-2H-benzopyran

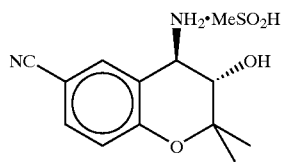
A.

The title compound is prepared as described in K. Atwal et al, J. Med. Chem. (1993) 36, 3971–3974 and references cited therein.

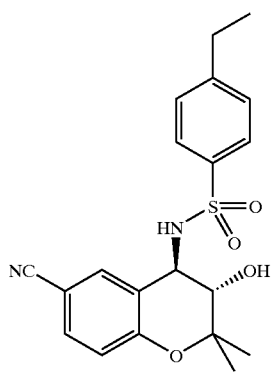
B.

Part A compound (trans-4-Amino-3,4-dihydro-2,2-dimethyl-6-cyano-2H-benzopyran) (5100 mg, 17.8 mmol) and triethylamine (2100 mg; 20.8 mmol) were dissolved in 50 mL of dichloromethane and cooled to 0° C. 4-Ethylbenzene-sulfonyl chloride (3930 mg, 19.2 mmol) in 20 mL of dichloromethane was added dropwise and the reaction was stirred for 1 hour. The pH was then adjusted to 7 with 300 uL of triethylamine. After 1 additional hour the reaction was diluted with dichloromethane (100 mL) and washed with water (30 mL), saturated aqueous ammonium chloride (20 mL) and brine (50 mL). The organic phase was dried over magnesium sulfate, filtered and the solvent removed to provide 5.84 g (85%) of an off-white solid. The solid was used in the next reaction without further purification. LCMS—84% at 3.7 min (YMC S5 C18 4.6×50 mm Ballistic Column) 10–90% MeOH/Water with 0.2% TFA linear gradient over 4 min, 4 mL/min UV Detection at 220 nm, M+H 387.0.

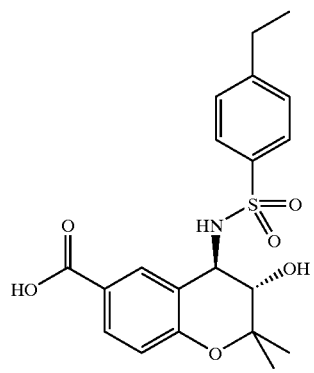
C.

Part B benzopyran (5800 mg, 15 mmol) was added to 200 mL of water with sodium peroxide (5860 mg, 75 mmol) and all the solid dissolved. The solution was heated at 60° C. for 48 hours. Sodium peroxide (2000 mg, 26 mmol) was added and the solution heated for 72 hours. The reaction was acidified by addition of hydrochloric acid (100 mL, 1.0 M, aq.). The mixture was extracted with ethyl acetate (3×75 mL) and the organic phase washed with brine (50 mL) and dried over magnesium sulfate, filtered and the solvent removed to yield 6 g of an off white solid. Purification by flash chromatography on silica gel eluted with 7% methanol, dichloromethane yielded 2.0 g (33%) of title compound in the form of a white solid. HPLC—98% at 3.6 min (YMC S5 C18 4.6×50 mm Ballistic Column) 10–90% MeOH/Water with 0.2% $H_3PO_4$ linear gradient over 4 min, 4 mL/min UV Detection at 220 nm, $^1$H NMR (270 MHz, $CDCl_3$) $^{13}$C NMR (68 MHz, $CDCCl_3$).

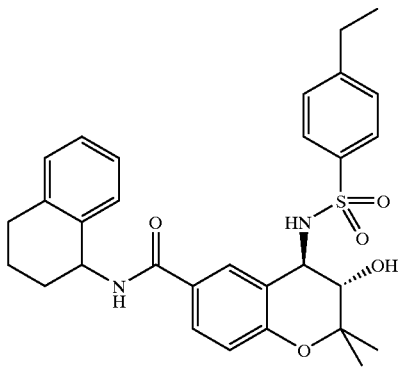
D.

1,2,3,4-Tetrahydro-1-naphthalamine (10.6 mg, 0.072 mmol) was weighed neat into a 16×100 mm test tube. The Part C acid (24.3 mg, 0.06 mmol) was dissolved in 1 mL of acetonitrile with 50 uL of dimethyl formamide. 4-Dirmethylaminopyridine (100 uL of a 0.06M soln in MeCN) and 1-(3-dimethylaminopropyl)-3-ethylcarbodiimide hydrochloride (1.2 mL of a 0.06 M soln in MeCN) were added and the tube was shaken on a vortex mixer overnight. The reaction was loaded onto a strong cation exchange solid phase extraction cartridge (CUBCX 12M6 SPE, 2 g, 6 mL) that had been conditioned by elution with two 10 mL portions of methanol. The cartridge was eluted with 20 mL of 25% methanol/dichloromethane and the solvent removed to provide 25 mg (78%) of a tan solid. HPLC analysis showed 68% of a major product which was purified by reverse phase HPLC (YMC S5 C18 20×100 mm Column) 50–90% MeOH/Water with 0.1% TFA linear gradient over 10 min, 20 mL/min UV detection at 220 nm). The relevant fraction was collected and dried in vacuo to give 18.4 mg (51%) of title compound in the form of a white solid. HPLC—97% at 2.0 min (Phenom-LUNA S5 C18 4.6×30 mm column) 50–90% MeOH/Water with 0.2% $H_3PO_4$ linear gradient over 2 min, 5 mL/min UV detection at 220 nm; $^1$H NMR (400 MHz, $CD_3OD$).

EXAMPLES 2–4

The following compounds were synthesized by the rocedures described in Example 1.

| Example | Structure | Mass spec m/z |
|---|---|---|
| 2 | 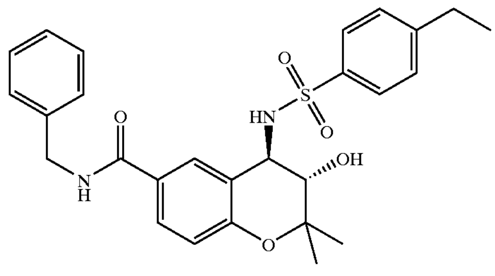 | 495 (M + H) |
| 3 | 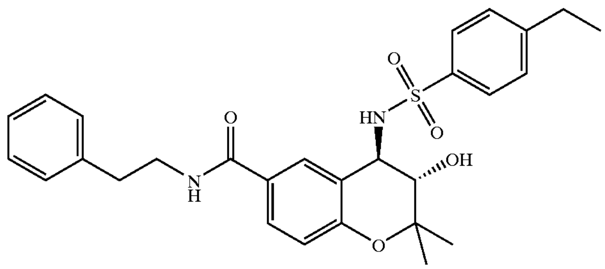 | 509 (M + H) |
| 4 | 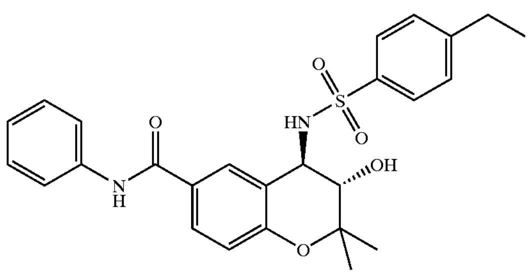 | 481 (M + H) |

Example 5

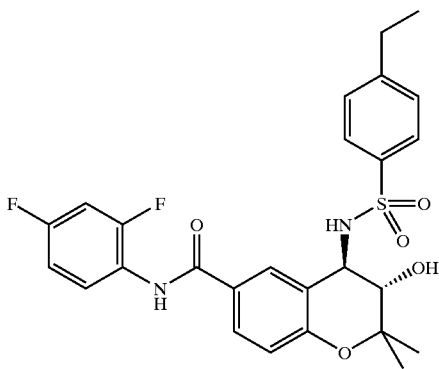

Example 1 Part C acid (24.3 mg, 0.06 mmol) was dissolved in 1 mL of acetonitrile in a 16×100 mm test tube with heating (steam bath). 2,4-Difluoroaniline (8.1 mg, 0.066 nmol) and 1-hydroxy-7-azabenzotriazole (9.0 mg, 0.072 mmol) were added to produce a slurry. 1-(3-Dimethylaminopropyl)-3-ethylcarbodiimide hydrochloride (9.3 mg, 0.066 mmol) in 1 ml of acetonitrile was added and all dissolved. The tube was heated for 6 days at 60° C. in a sand bath and was loaded directly onto a strong cation exchange solid phase extraction cartridge (CUBCX 12M6 SPE, 2 g, 6 mL) that had been conditioned by elution with. two 10 mL portions of methanol, followed by 10 mL of acetonitrile. The cartridge was eluted with 10 mL of 5% methanol/acetonitrile and relevant fraction was collected and dried in vacuo to give mg (97%) of a white solid. HPLC-MS analysis showed 51% of the desired product and 43% of a product consistent with the 1-hydroxy-7-azabenzotriazole (HOAt) ester of the starting acid. The mixture was purified by derivitizing the remaining HOAt ester with N-phenylethylenediamine (4 uL, 0.03 mmol) in 1 ml of acetonitrile. The reaction was shaken on a vortex mixer for 12 hours and was loaded directly onto a strong cation exchange solid phase extraction cartridge (CUBCX 12M6 SPE, 2 g, 6 mL) that had been conditioned by elution with two 10 mL portions of methanol then 10 mL acetonitrile. The cartridge was eluted with 10 mL of 5% methanol/acetonitrile and relevant fraction was collected and dried in vacuo to give 17.7 mg (57%) of the desired title product as a white solid. HPLC—89% at 2.8 min (YMC S5 C18 4.6×50 mm Ballistic Column) 10–90% MeOH/Water with 0.2% $H_3PO_4$ linear gradient over 4 min, 4 mL/min UV detection at 220 nm. $^1$H NMR (400 MHz, $CD_3OD$) 42763-038-18, $^{13}$C NMR (68 MHz, $CD_3OD$)

EXAMPLES 6 TO 41

The following compounds were synthesized using the procedure described in Example 5.

| Example | Structure | Mass spec m/z |
|---|---|---|
| 6 | 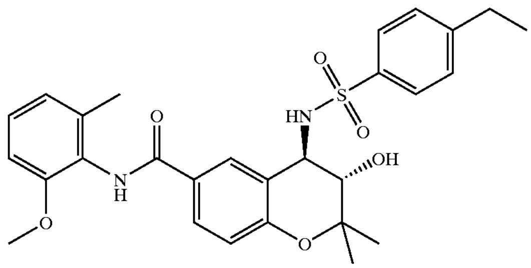 | 525 (M + H) |
| 7 | 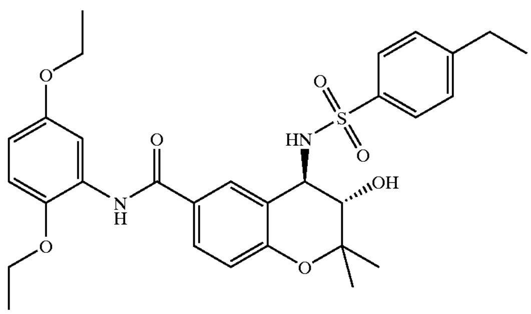 | 569 (M + H) |
| 8 | 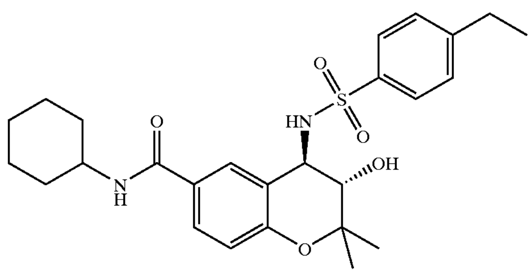 | 487 (M + H) |
| 9 | 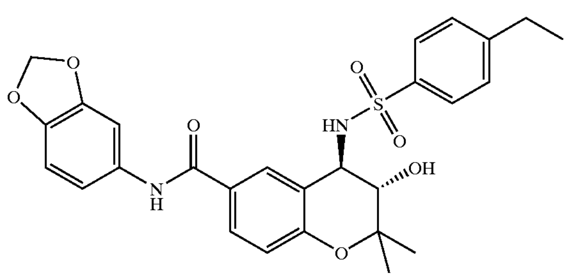 | 525 (M + H) |
| 10 | 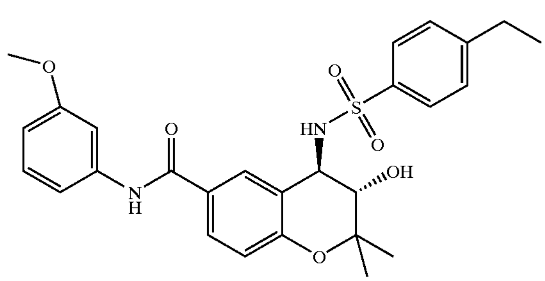 | 511 (M + H) |

-continued

| Example | Structure | Mass spec m/z |
|---|---|---|
| 11 | 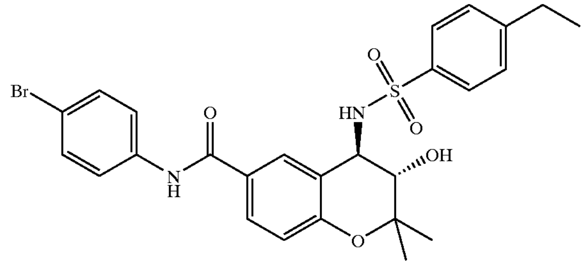 | 560 (M + H) |
| 12 | 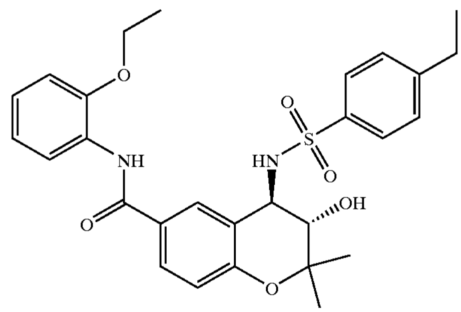 | 525 (M + H) |
| 13 | 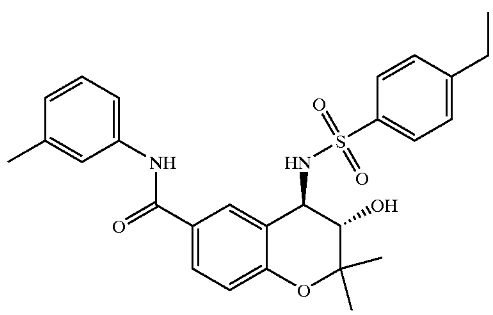 | 495 (M + H) |
| 14 | 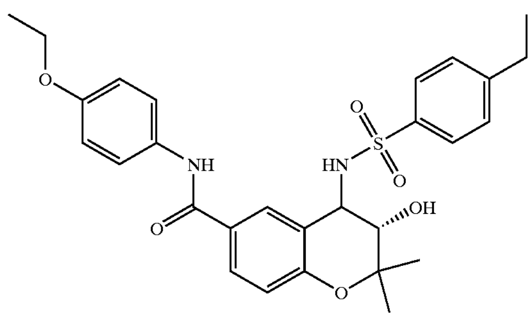 | 525 (M + H) |
| 15 | 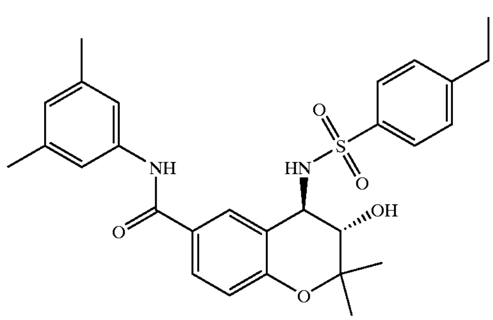 | 509 (M + H) |

-continued

| Example | Structure | Mass spec m/z |
|---------|-----------|---------------|
| 16 | 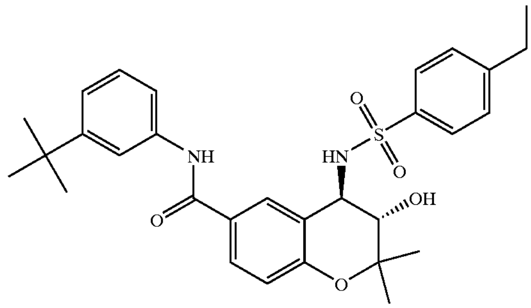 | 537 (M + H) |
| 17 | 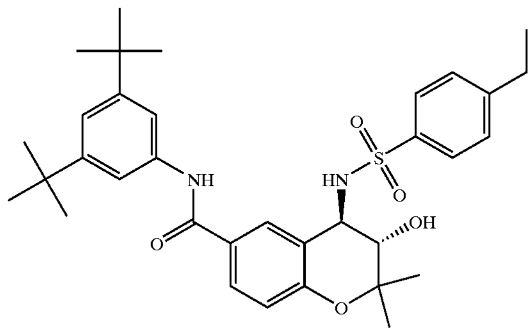 | 593 (M + H) |
| 18 | 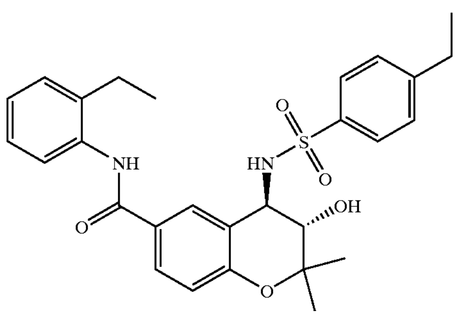 | 509 (M + H) |
| 19 | 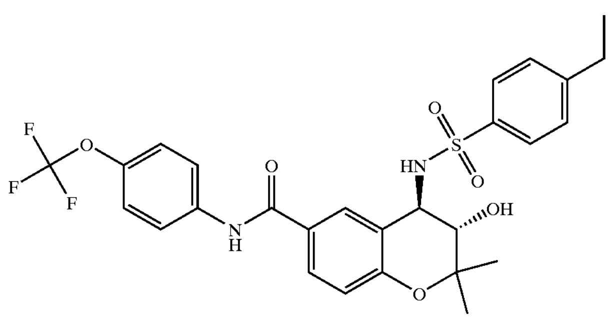 | 565 (M + H) |

-continued

| Example | Structure | Mass spec m/z |
|---------|-----------|---------------|
| 20 | 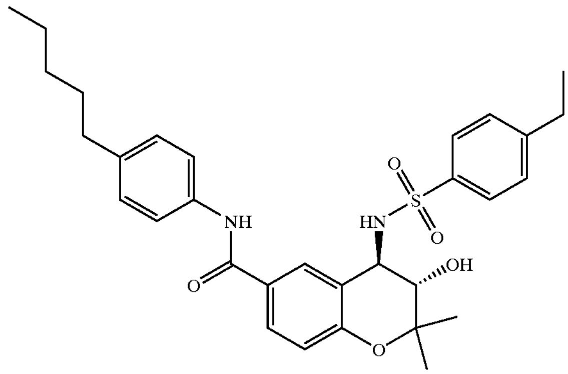 | 551 (M + H) |
| 21 | 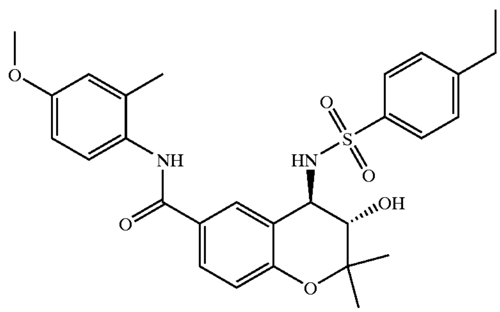 | 525 (M + H) |
| 22 | 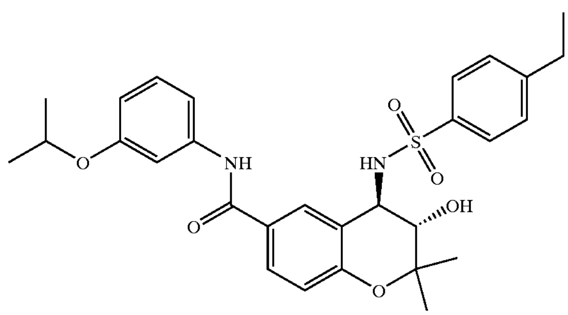 | 539 (M + H) |
| 23 | 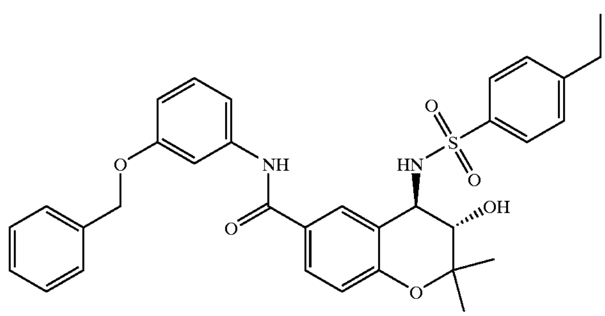 | 587 (M + H) |

-continued

| Example | Structure | Mass spec m/z |
|---|---|---|
| 24 | 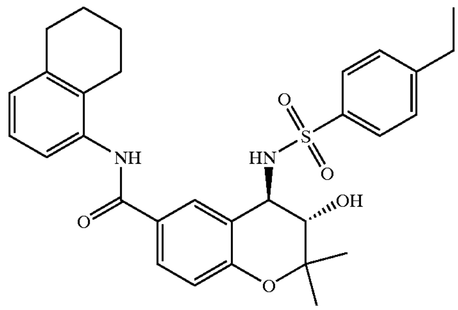 | 535 (M + H) |
| 25 | 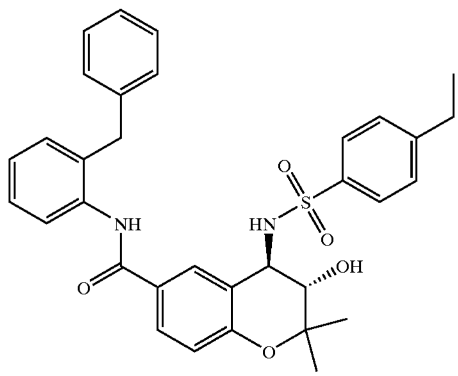 | 571 (M + H) |
| 26 | 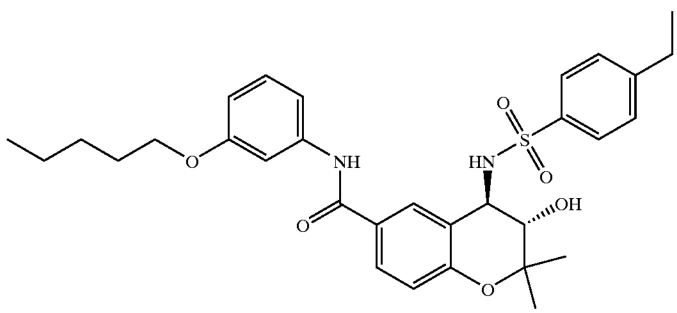 | 567 (M + H) |
| 27 | 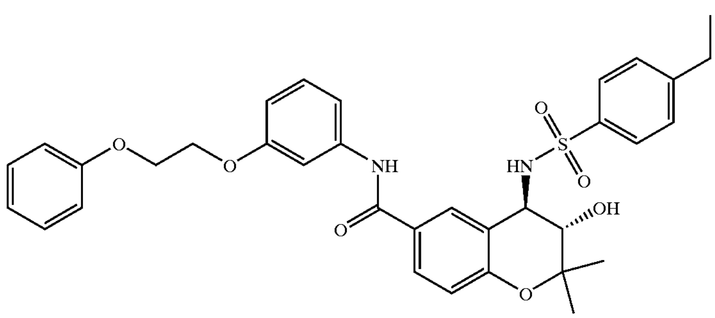 | 617 (M + H) |

| Example | Structure | Mass spec m/z |
|---|---|---|
| 28 | 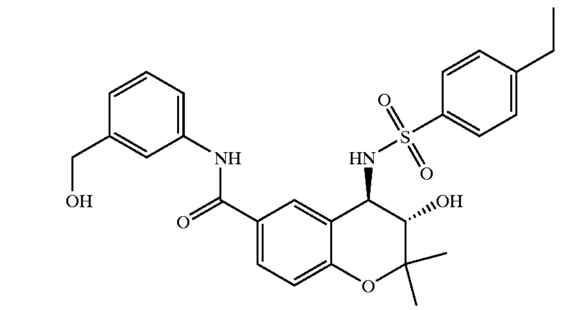 | 511 (M + H) |
| 29 | 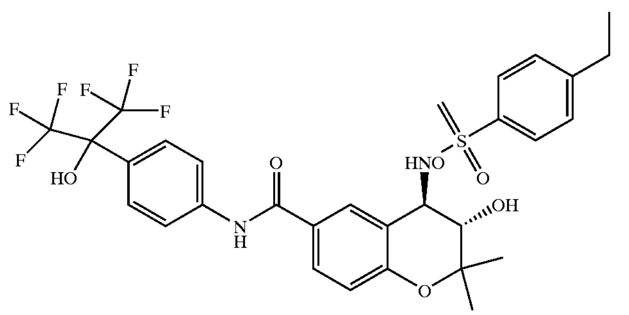 | 647 (M + H) |
| 30 | 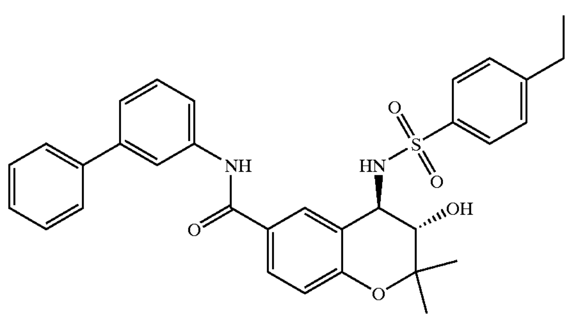 | 557 (M + H) |
| 31 | 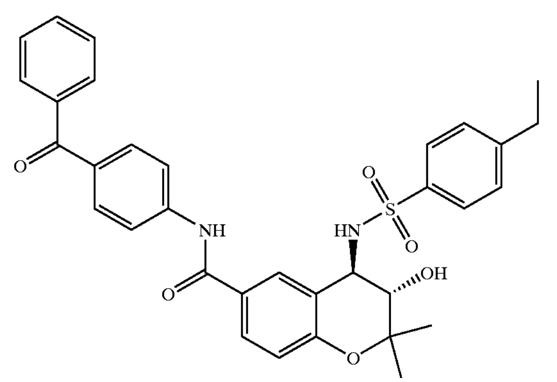 | 585 (M + H) |

-continued

| Example | Structure | Mass spec m/z |
|---|---|---|
| 32 | 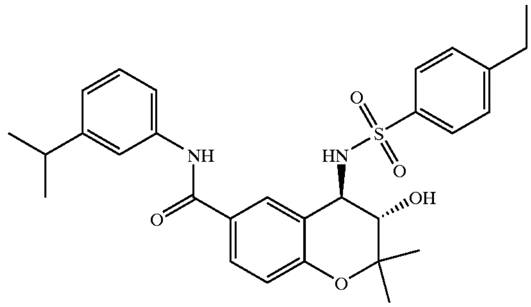 | 523 (M + H) |
| 33 | 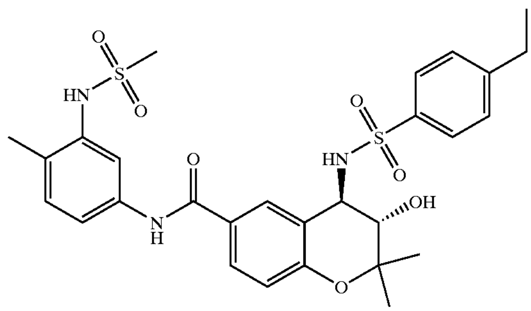 | 588 (M + H) |
| 34 | 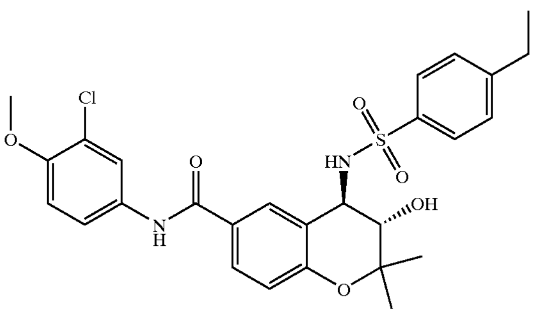 | 545 (M + H) |
| 35 | 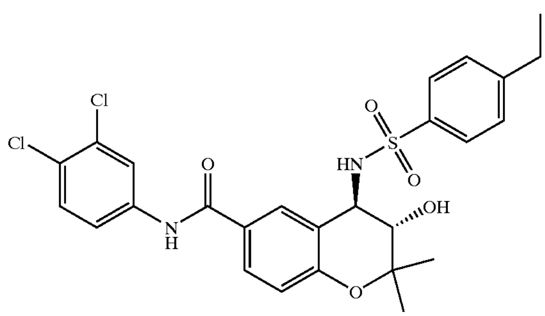 | 549 (M + H) |
| 36 | 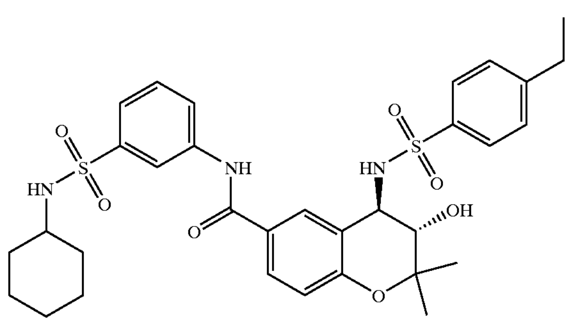 | 642 (M + H) |

| Example | Structure | Mass spec m/z |
|---|---|---|
| 37 | 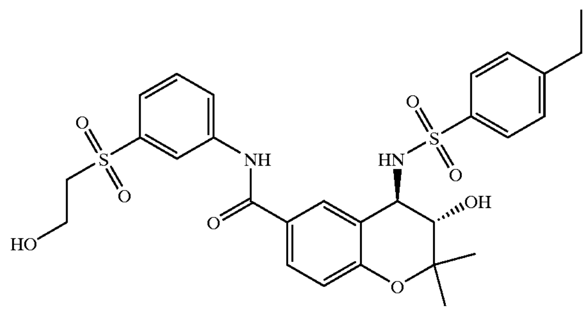 | 589 (M + H) |
| 38 | 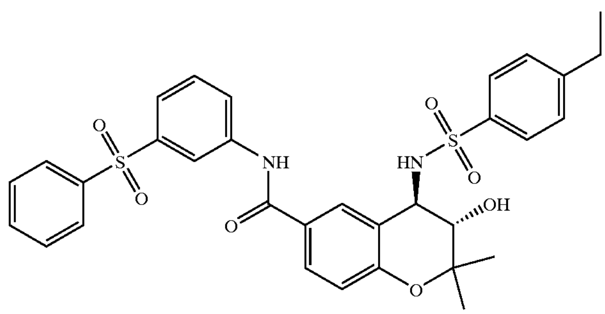 | 621 (M + H) |
| 39 | 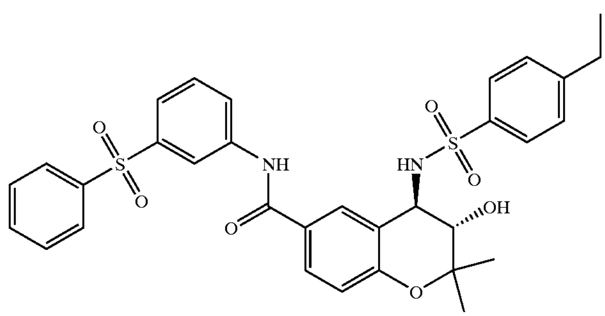 | 495 (M + H) |
| 40 and 41 | 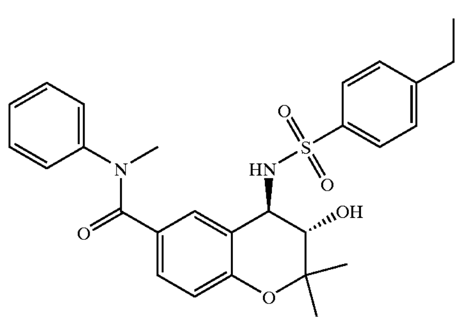 | 481 (M + H) |

EXAMPLE 42

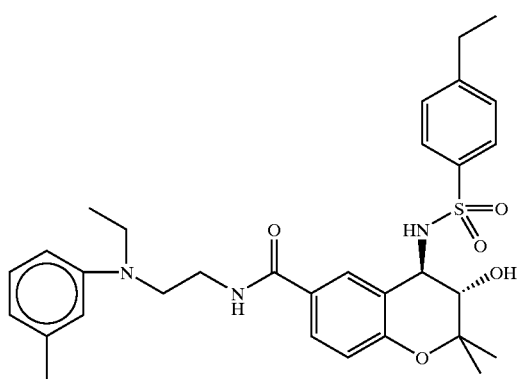

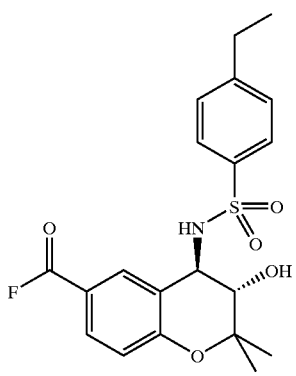

Example 1 Part C benzopyran acid (1000 mg, 2.5 rnmol) was combined with tetramethylfluoroformamidinium hexaflurophosphate (660 mg 2.5 mmol) and triethylamine (522 ul, 3.75 mmol) in dichioromethane and all the solids dissolved. After 15 min the solvent was evaporated and the crude solid was partially redissolved in 2:1 hexane:ethyl acetate and the slurry was placed directly on a silica gel column. The column was eluted with 2:1 hexane:ethyl acetate and relevent fractions were combined to give 740 mg (74%) of a white cry staline solid.

Part A acid fluoride (20.4 mg, 0.05 mmol), N-(2-aminoethyl)-N-ethyl-m-toluidine (8.9 mg, 0.05 mmol) and triethylamine (10.4 ul, 0.075 mmol) were dissolved in 1 mL of acetonitrile in a 16×100 mm test tube and shaken on a vortex mixer. After 15 minutes the contents of the tube was loaded directly onto a strong cation exchange solid phase extraction cartridge (CUBCX 12M6 SPE, 2 g, 6 mL) that had been conditioned by elution with two 10 mL portions of methanol. The cartridge was eluted with 20 mL of methanol which was discarded. The cartridge was then eluted with 10 mL of 1 N ammonia in methanol and the relevant fraction was collected and dried in vacuo to give 28.5 mg (100%) of title compound in the form of a white solid. HPLC—94% at 3.6 min (YMC S5 C18 4.6×50 mm Ballistic Column) 10–90% MeOH/Water with 0.2% $H_3PO_4$ linear gradient over 4 min, 4 mL/min, UV detection at 220 nm; LC-MS 93% at 3.6 min (YMC S5 C18 4.6×50 mm Ballistic Column) 10–90% MeOH/Water with 0.2% TFA linear gradient over 4 min, 4 mL/min UV detection at 220 nm, M+H 566.2. $^1$H NMR (400 MHz, $CD_3OD$)

EXAMPLES 43 TO 107

The following compounds were synthesized using the methods described in Example 42.

| Example | structure | Mass Spec m/Z |
|---|---|---|
| 43 | 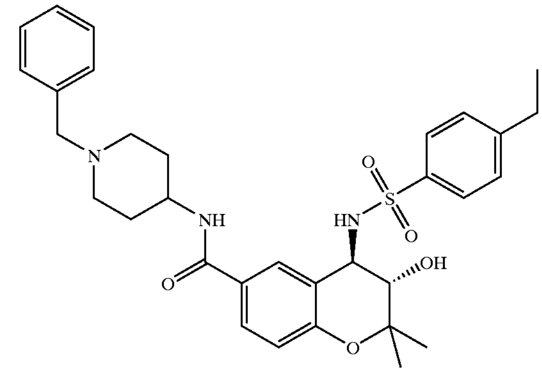 | 578 (M + H) |

-continued

| Example | structure | Mass Spec m/Z |
|---|---|---|
| 44 | 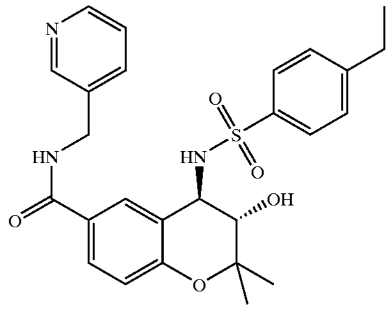 | 496 (M + H) |
| 45 | 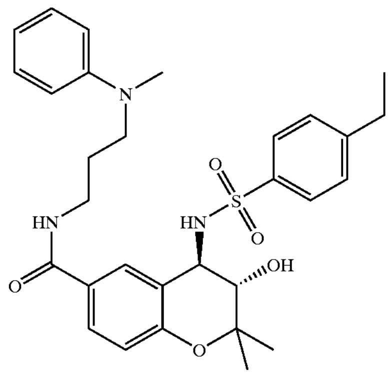 | 552 (M + H) |
| 46 | 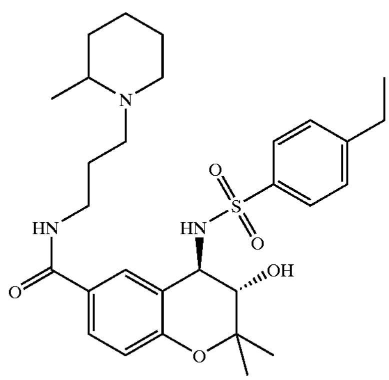 | 544 (M + H) |
| 47 | 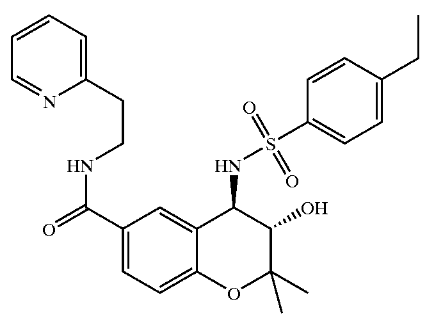 | 510 (M + H) |

| Example | structure | Mass Spec m/Z |
|---|---|---|
| 48 | 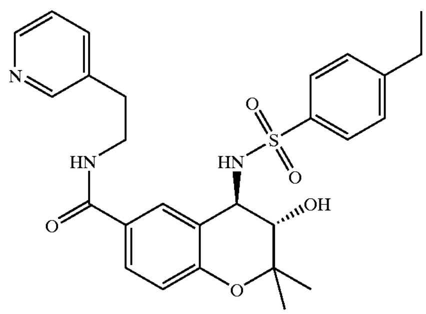 | 510 (M + H) |
| 49 | 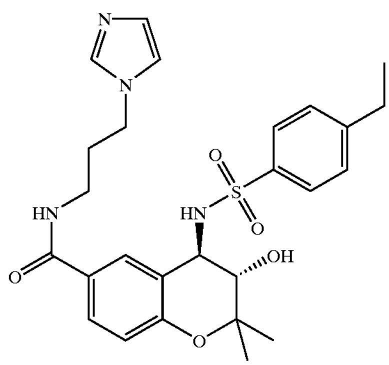 | 513 (M + H) |
| 50 | 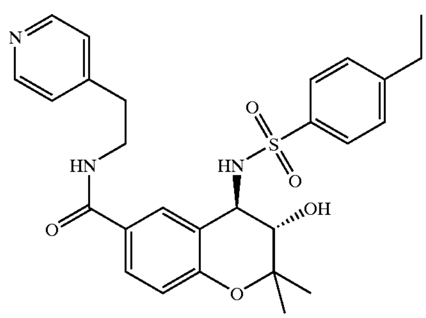 | 510 (M + H) |
| 51 | 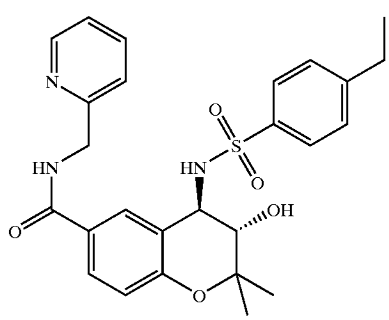 | 496 (M + H) |

-continued

| Example | structure | Mass Spec m/Z |
|---|---|---|
| 52 | 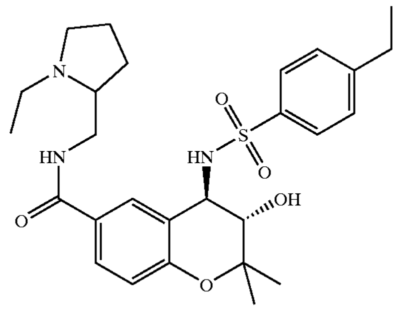 | 516 (M + H) |
| 53 | 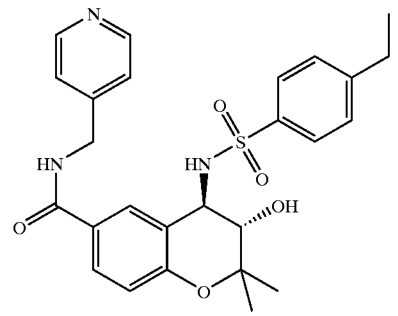 | 496 (M + H) |
| 54 | 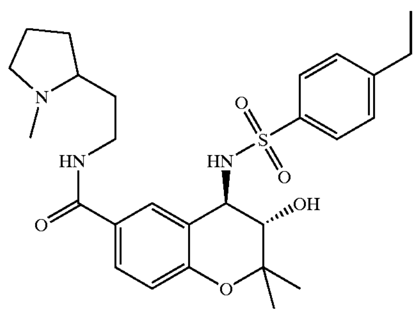 | 516 (M + H) |
| 55 | 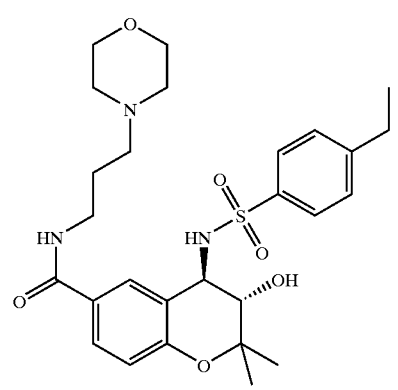 | 532 (M + H) |

-continued

| Example | structure | Mass Spec m/Z |
|---|---|---|
| 56 | 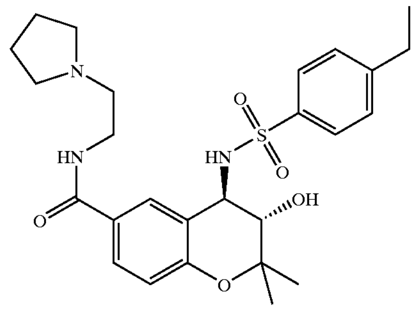 | 502 (M + H) |
| 57 | 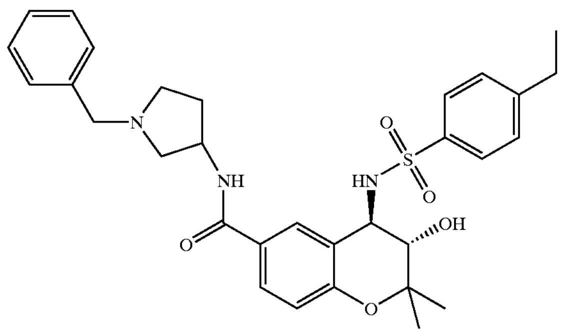 | 564 (M + H) |
| 58 | 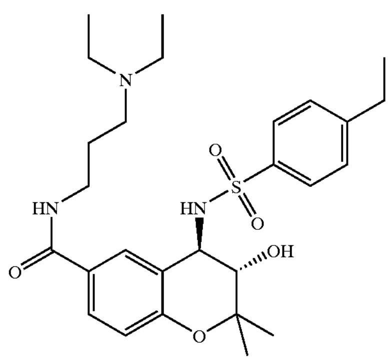 | 518 (M + H) |
| 59 | 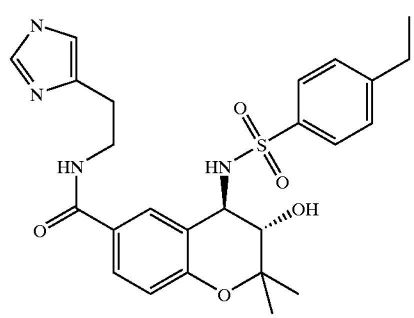 | 499 (M + H) |

-continued

| Example | structure | Mass Spec m/Z |
|---|---|---|
| 60 | 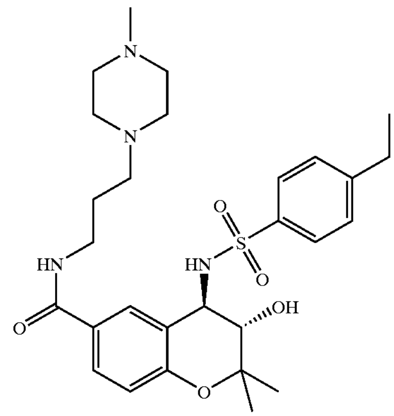 | 545 (M + H) |
| 61 | 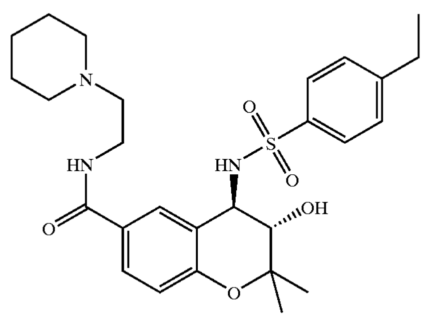 | 516 (M + H) |
| 62 | 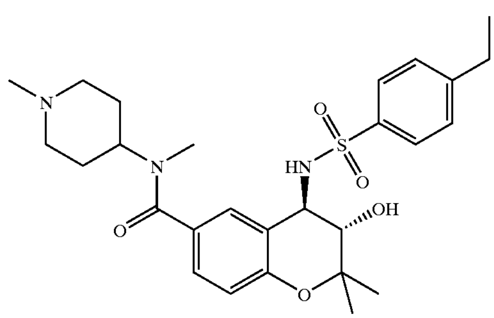 | 516 (M + H) |
| 63 | 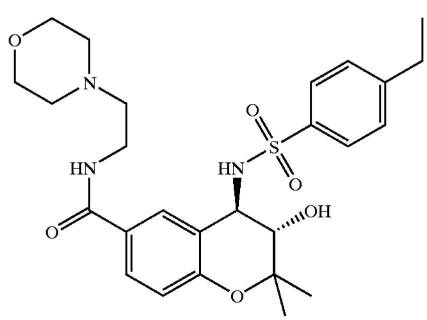 | 518 (M + H) |

-continued

| Example | structure | Mass Spec m/Z |
|---------|-----------|---------------|
| 64 | 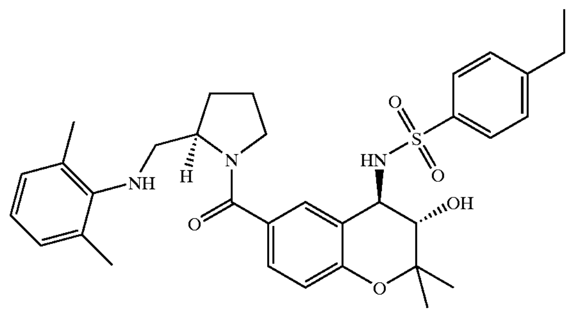 | 592 (M + H) |
| 65 | 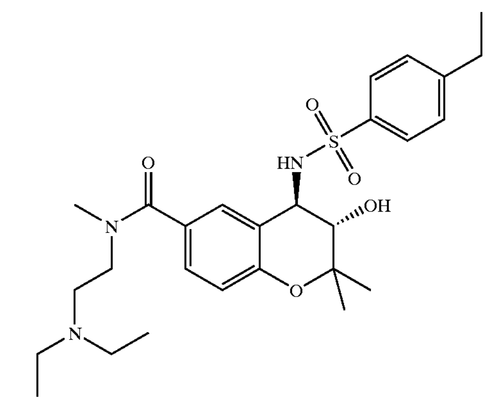 | 518 (M + H) |
| 66 | 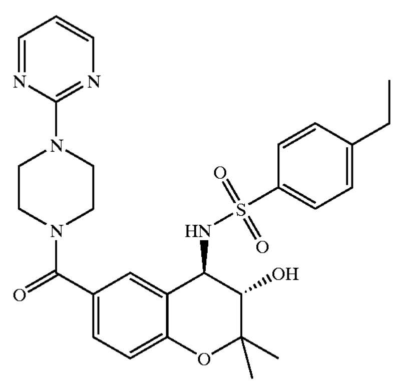 | 552 (M + H) |
| 67 | 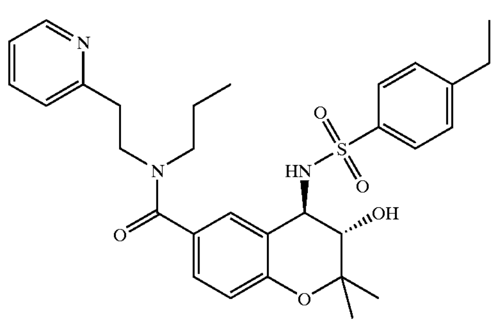 | 552 (M + H) |

-continued
| Example | structure | Mass Spec m/Z |
|---|---|---|
| 68 | 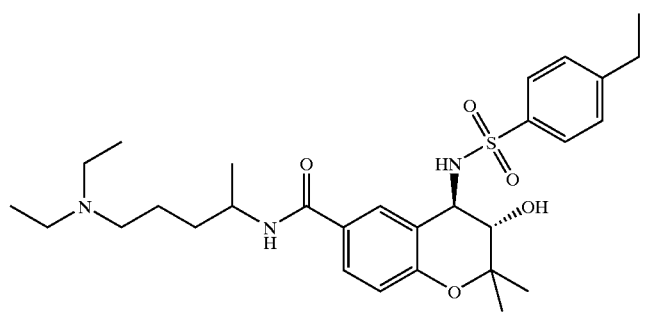 | 546 (M + H) |
| 69 | 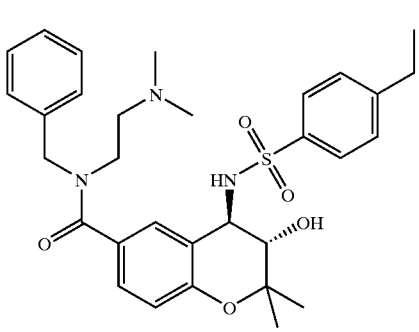 | 566 (M + H) |
| 70 | 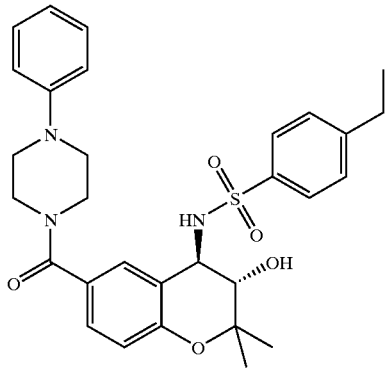 | 550 (M + H) |
| 71 | 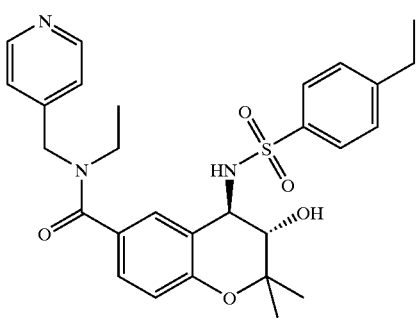 | 524 (M + H) |

-continued
| Example | structure | Mass Spec m/Z |
|---|---|---|
| 72 | 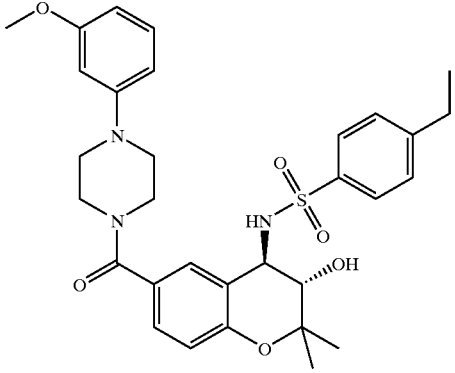 | 580 (M + H) |
| 73 | 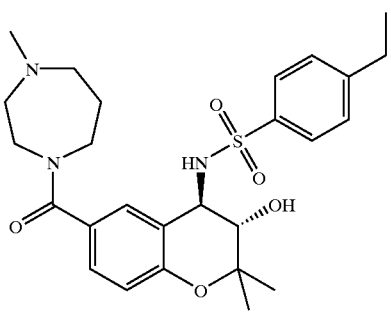 | 502 (M + H) |
| 74 | 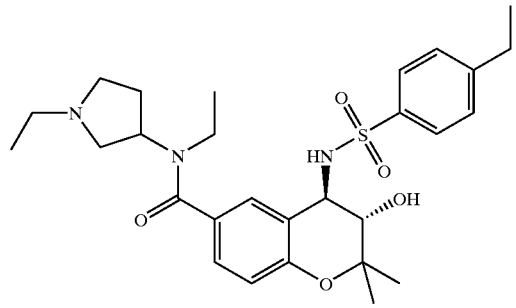 | 530 (M + H) |
| 75 | 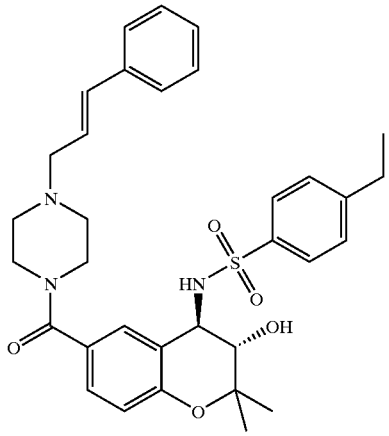 | 590 (M + H) |

-continued
| Example | structure | Mass Spec m/Z |
|---|---|---|
| 76 | 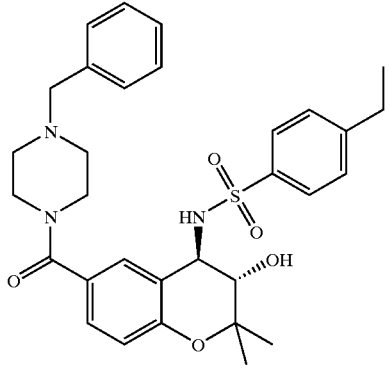 | 564 (M + H) |
| 77 | 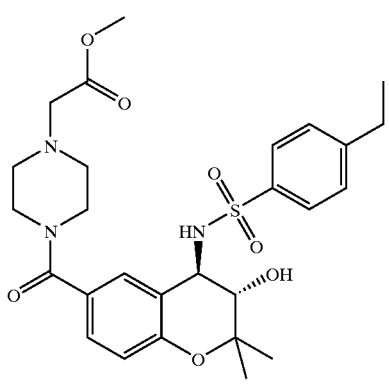 | 560 (M + H) |
| 78 | 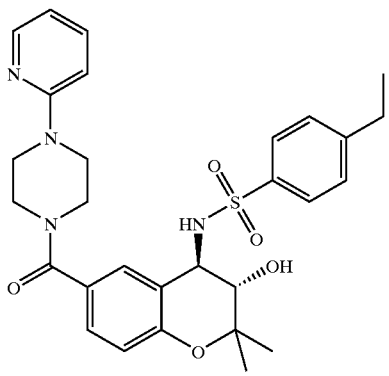 | 551 (M + H) |
| 79 | 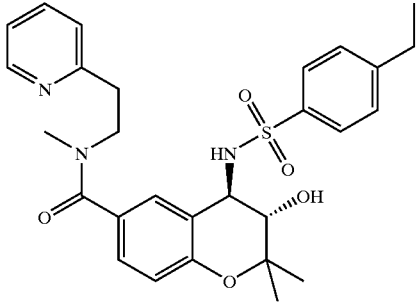 | 524 (M + H) |

-continued

| Example | structure | Mass Spec m/Z |
|---------|-----------|---------------|
| 80 | 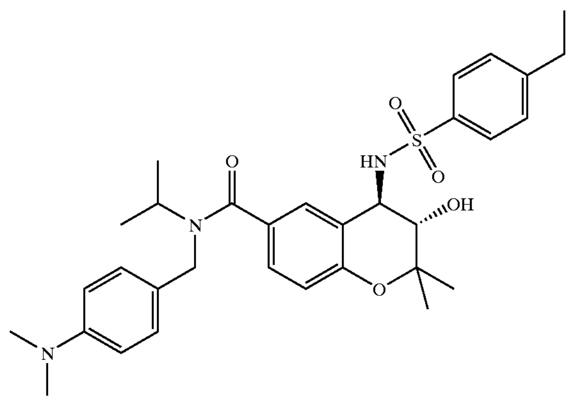 | 580 (M + H) |
| 81 | 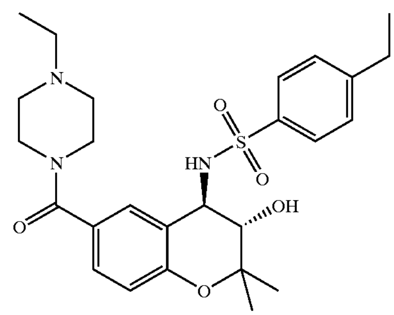 | 502 (M + H) |
| 82 | 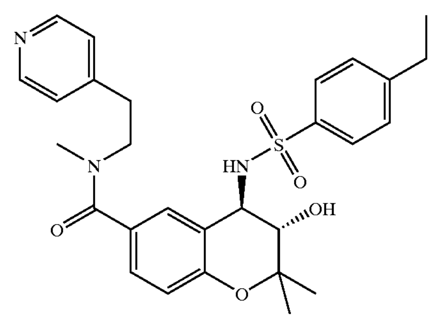 | 524 (M + H) |
| 83 | 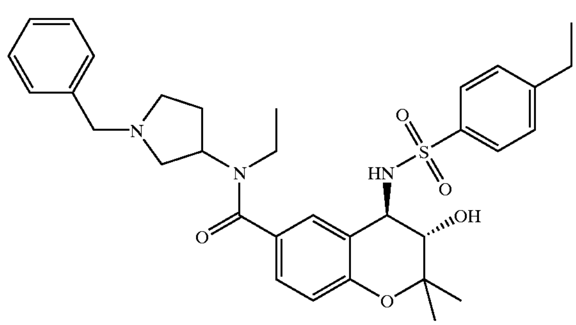 | 592 (M + H) |

-continued
| Example | structure | Mass Spec m/Z |
|---------|-----------|---------------|
| 84 | 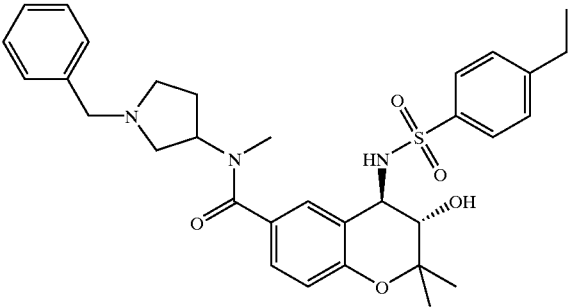 | 578 (M + H) |
| 85 | 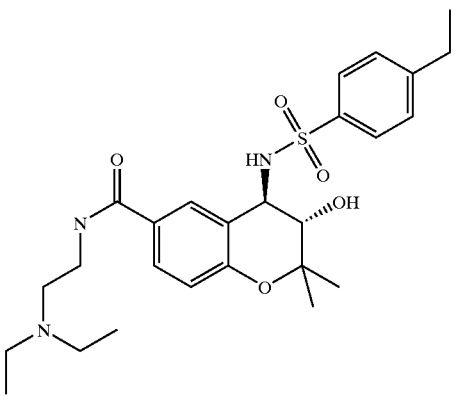 | 504 (M + H) |
| 86 | 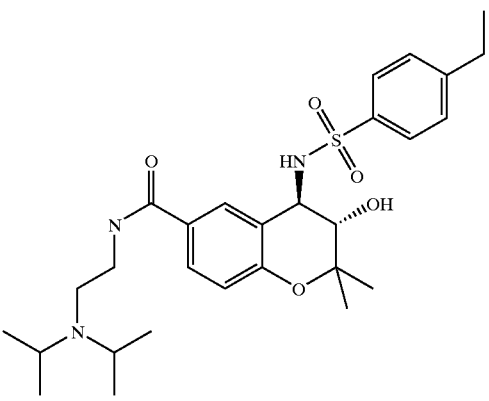 | 532 (M + H) |
| 87 | 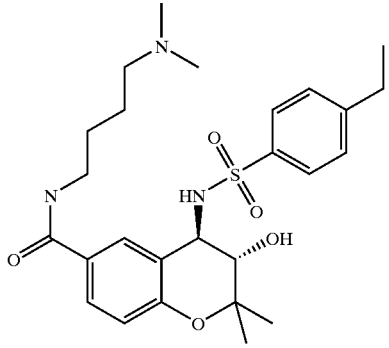 | 504 (M + H) |

-continued

| Example | structure | Mass Spec m/Z |
|---|---|---|
| 88 | 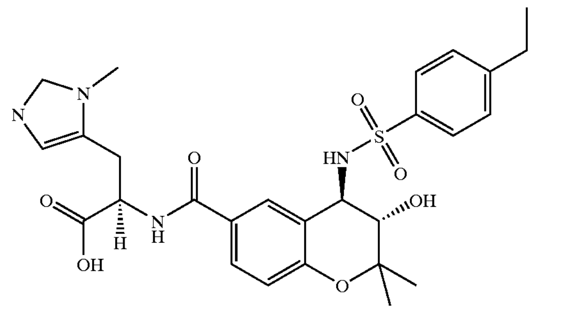 | 557 (M + H) |
| 89 | 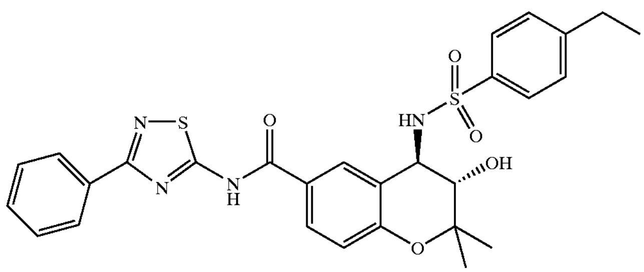 | 565 (M + H) |
| 90 | 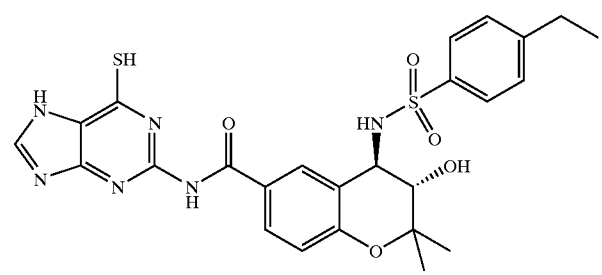 | 555 (M + H) |
| 91 | 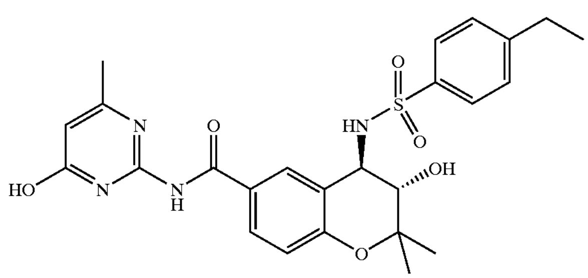 | 513 (M + H) |
| 92 | 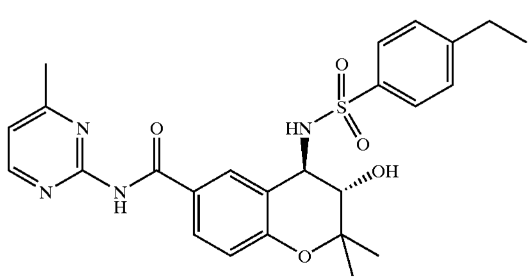 | 497 (M + H) |

-continued
| Example | structure | Mass Spec m/Z |
|---|---|---|
| 93 | 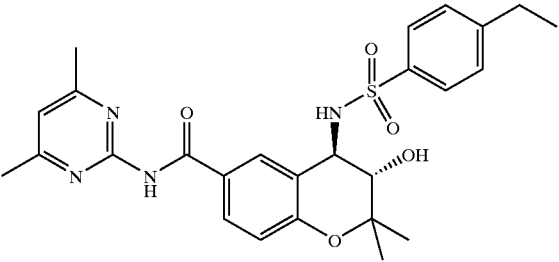 | 511 (M + H) |
| 94 | 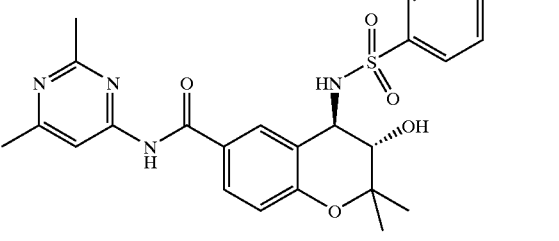 | 511 (M + H) |
| 95 | 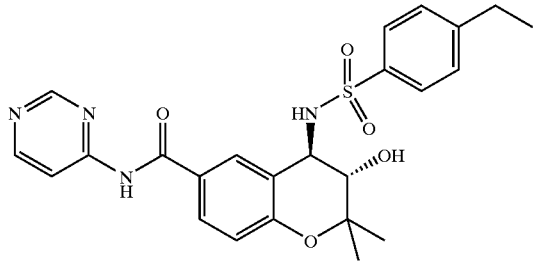 | 483 (M + H) |
| 96 | 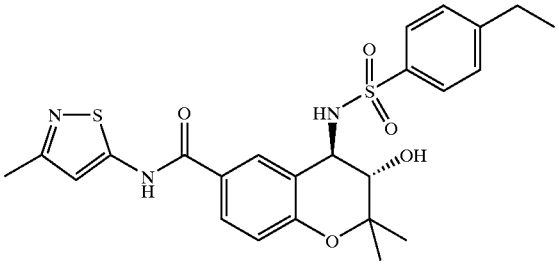 | 502 (M + H) |
| 97 | 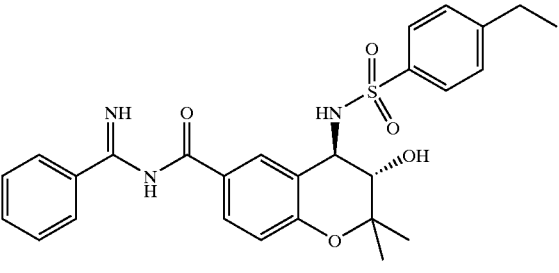 | 508 (M + H) |

| Example | structure | Mass Spec m/Z |
|---|---|---|
| 98 | 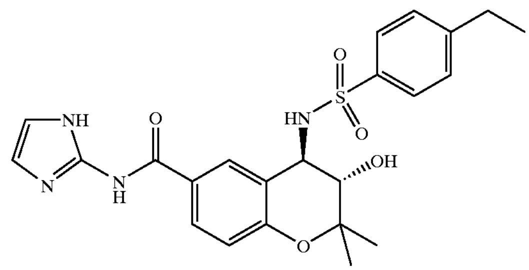 | 471 (M + H) |
| 99 | 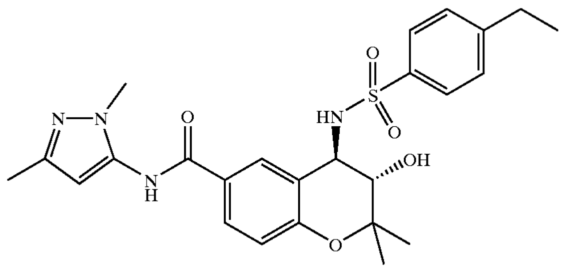 | 499 (M + H) |
| 100 | 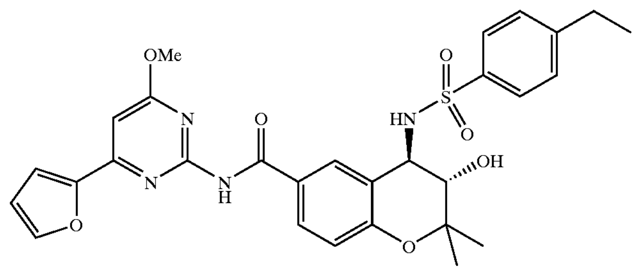 | 579 (M + H) |
| 101 | 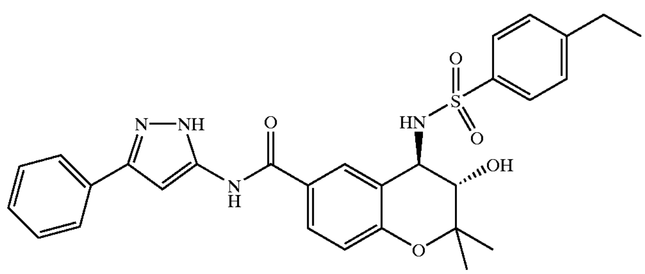 | 547 (M + H) |
| 102 | 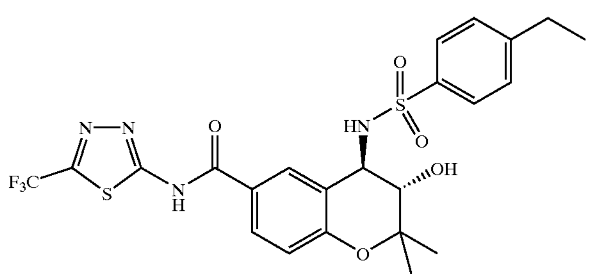 | 557 (M + H) |

-continued
| Example | structure | Mass Spec m/Z |
|---|---|---|
| 103 | 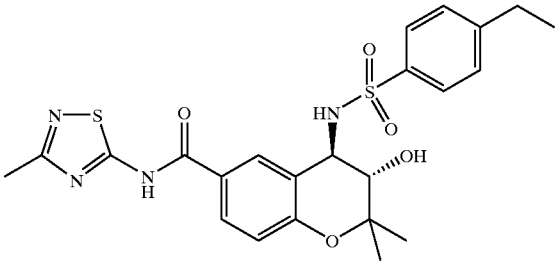 | 503 (M + H) |
| 104 | 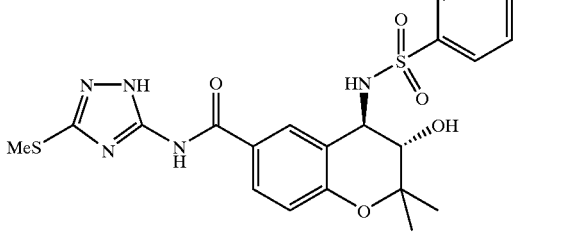 | 518 (M + H) |
| 105 | 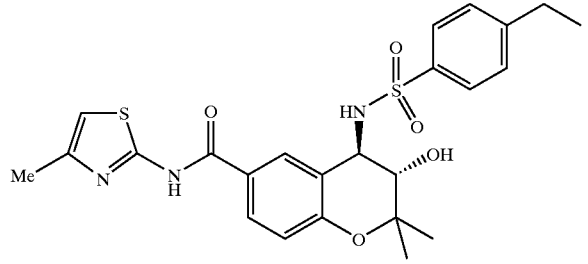 | 502 (M + H) |
| 106 | 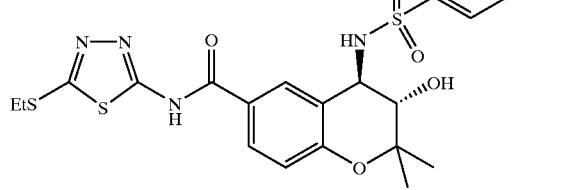 | 549 (M + H) |
| 107 | 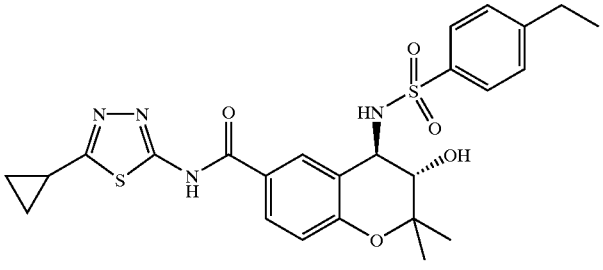 | 529 (M + H) |

EXAMPLE 108

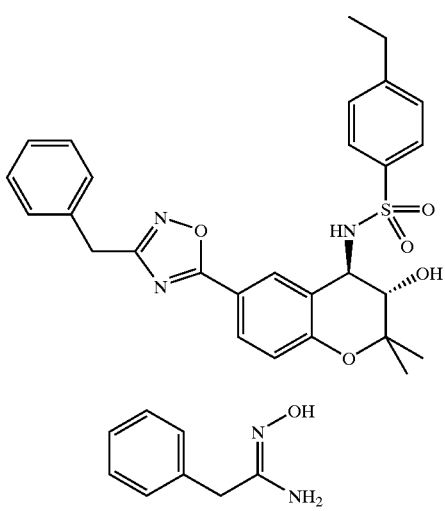

A.

B.

The title hydroxyamidine was synthesized by methods described in J. Med. Chem., 1991, 34, 140–151.

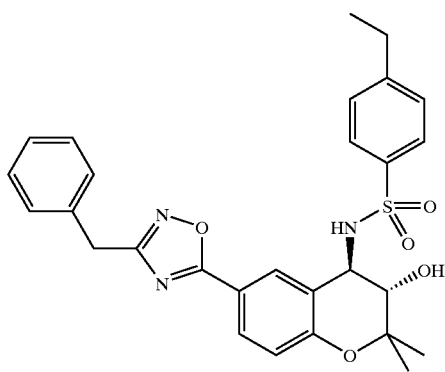

Example 1 Part C benzopyran acid (50 mg, 0.12 mmol) was suspended in 1 mL of dichloromethane. Triethylamine (26 μL, 0.19 mmol) and Part A hydroxyamidine (19 mg, 0.12 mmol) were added followed by (benzotriazol-1-yloxy)-trispyrrolidinophosphonium hexafluorophosphoate (PyBOP) (83 mg, 0.16 mmol). All the solid dissolved upon addition of PyBOP and the reaction was stirred for 15 hrs. The mixture was diluted with ethyl acetate and washed with hydrochloric acid (1.0 M, aq.), sodium bicarbonate (sat'd., aq.) and sodium chloride (sat'd., aq.). The organic phase was dried over magnesium sulfate, filtered and the solvent removed to provide 90 mg of a colorless oil. The oil was dissolved in 1 mL of tetrahydrofuran, cesium carbonate (88 mg, 0.27 mmol) was added and the mixture was heated to 50° for 15 hrs. The reaction was diluted with ethyl acetate and washed with hydrochloric acid (1.0 M, aq.), sodium bicarbonate (sat'd., aq.) and sodium. chloride (sat'd., aq.). The organic phase was dried over magnesium sulfate, filtered and the solvent removed to provide 50 mg of title product in the form of a white solid. Purification by flash chromatography on silica gel eluted with 20% acetone, hexane yielded 30 mg (47%) of a white solid. mp 186–187°; $[\alpha]D$ −137° (CHC13, c0.45) $^1$H NMR (400 MHz, CDCl$_3$); $^1$H NMR (400 MHz, acetone-d$^6$); $^{13}$C NMR (100 MHz, CDCl$_3$); Mass Spec (ESI).

EXAMPLES 109 TO 111

The following compounds were synthesized by the procedures described in Example 108.

| Example | Structure | Mass Spec m/z |
|---|---|---|
| 109 | 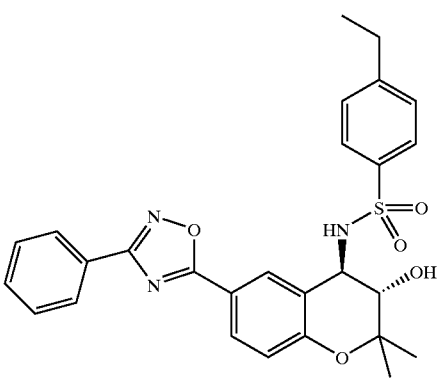 | 506 (M + H) |

-continued

| Example | Structure | Mass Spec m/z |
|---------|-----------|---------------|
| 110 | 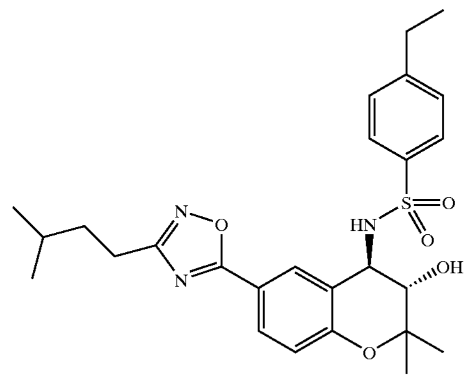 | 500 (M + H) |
| 111 | 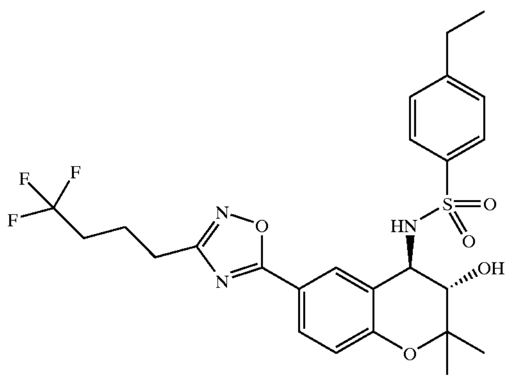 | 540 (M + H) |

EXAMPLE 112

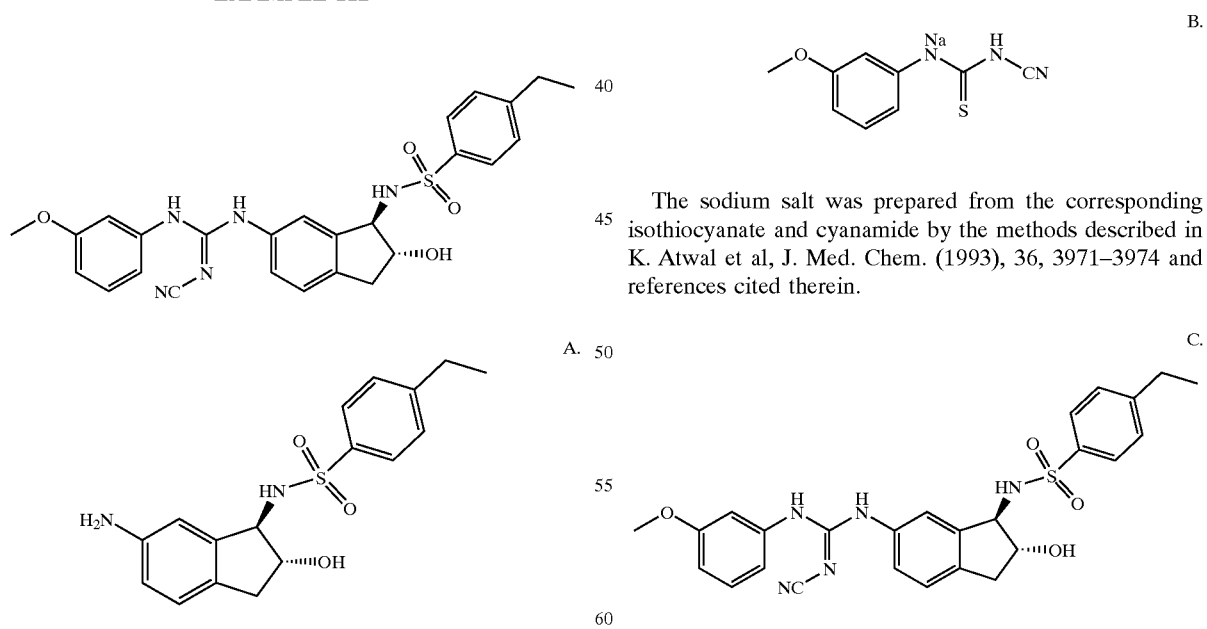

The Part A compound was prepared as described in ICAgen Inc., Lilly & Co. patent application WO9804521-A1 (Preparation 6).

The sodium salt was prepared from the corresponding isothiocyanate and cyanamide by the methods described in K. Atwal et al, J. Med. Chem. (1993), 36, 3971–3974 and references cited therein.

Part A aniline. (50 mg, 0.15 mmol) and Part B sodium salt (41 mg, 0.18 mmol) were dissolved in 4 mL of anhydrous N,N-dimethylformamide. 1-(3-Dimethylaminopropyl)-3-ethylcarbodiimide hydrochloride (35 mg, 0.18 mmol) was then added at room temperature and the reaction was stirred at room temperature under argon for 16 hr. The reaction was then partitioned between citric acid (5%, aqueous) and ethyl acetate. The aqueous phase was extracted with ethyl acetate and the organic extracts were washed with aqueous lithium chloride (10%), dried over $Na_2SO_4$, filtered and the solvent removed to provide 81 mg of crude product. The crude material was purified by flash chromatography ($SiO_2$, 13.5 g, 4% methanol, dichloromethane) and the product was concentrated in vacuo and azeotroped several times with a mixture of dichloromethane/hexane to provide 25 mg (33%) of title compound as a white solid. $^1$H NMR (400 MHz, $CD_3OD$); $^{13}$C NMR (100 MHz, $CD_3OD$). ms (ESI). HPLC: 99.1% at 3.6 min (YMC S5 ODS 4.6×50 mm C-18 column, 4 mL/ min, 10–90% methanol, water with 0.2% phosphoric acid, linear gradient over 4 min, 2 min hold, UV detection at 220 n).

EXAMPLE 113

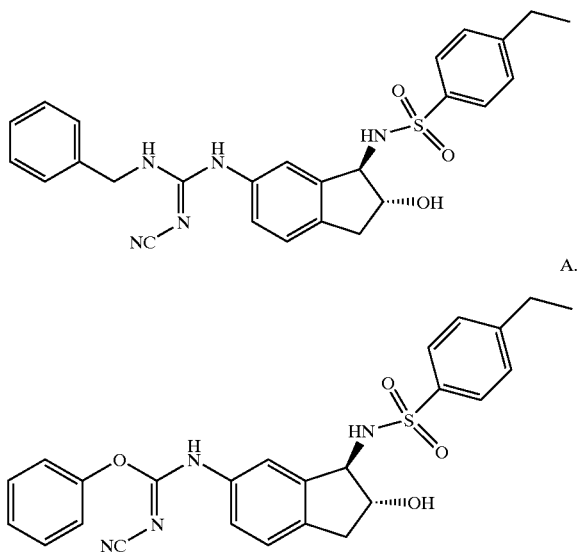

A.

Example 112 Part A amine (100 mg, 0.3 mmol) was partially dissolved in 5 mL anhydrous acetonitrile and diphenyl cyanocarbonimidate (72 mg, 0.3 mmol) was added and the reaction was heated to reflux. The reaction was refluxed for 18 hours, then was cooled to room temperature and concentrated in vacuo to a tan solid which was triturated with diisopropyl ether and dried in vacuo to provide 145 mg (assumed 100%) of the title cyanoimidate as a tan solid. $^1$H NMR (270 MHz, $CD_3OD+CDCl_3$) ; $^{13}$C NMR (68 MHz, $CD_3OD+CDCl_3$). ms (ESI).

B.

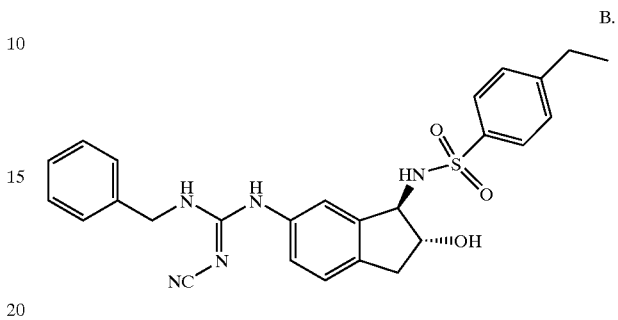

Part A cyanoimidate (30 mg, 0.063 mmol) was partially dissolved in 2 mL of isopropanol and then benzylamine (21 μL, 0.19 mmol) was added at room temperature via syringe. Dimethylsulfoxide (1 mL) was then added to the reaction mixture in order to effect a homogeneous solution. The reaction was stirred at room temperature under argon for 16 hr. The reaction was then concentrated in vacuo and the crude material was purified by flash chromatography ($SiO_2$, 5 g, 40% acetone, hexane). The product was concetrated in vacuo and azeotroped with dichloromethane, hexane to provide 15 mg (48%) of title compound in the form of a white solid as a racemic mixture.

mp 210–217° C. (dec). $^1$H NMR (400 MHz, $CD_3OD$); $^3$C NMR (100 MHz, $CD_3OD$). ms (ESI). HPLC: 100% at 3.8 min (YMC S5 ODS 4.6×50 mm C-18 column, 10–90% methanol, water with 0.2% phosphoric acid, linear gradient over 4 min, 4 mL/min, UV detection at 220 nM).

EXAMPLES 114 TO 117

The following compounds were synthesized by the procedures described in Example 113.

| Example | Structure | Mass Spec m/z |
|---------|-----------|---------------|
| 114 | 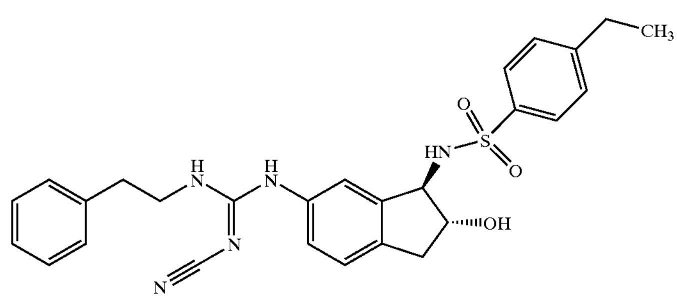 | 504 |

| Example | Structure | Mass Spec m/z |
|---|---|---|
| 115 | 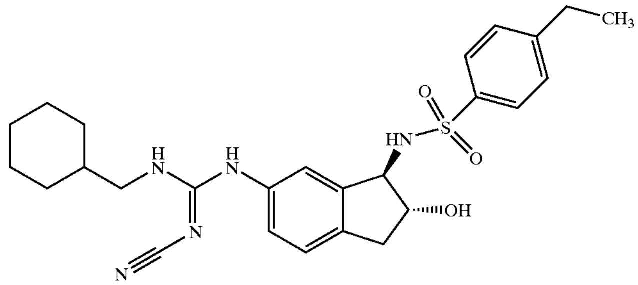 | 496 (M + H) |
| 116 | 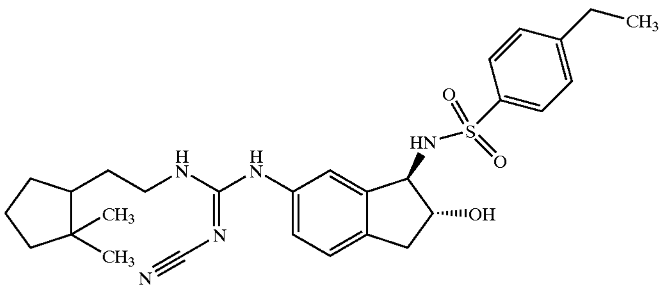 | 524 (M + H) |
| 117 | 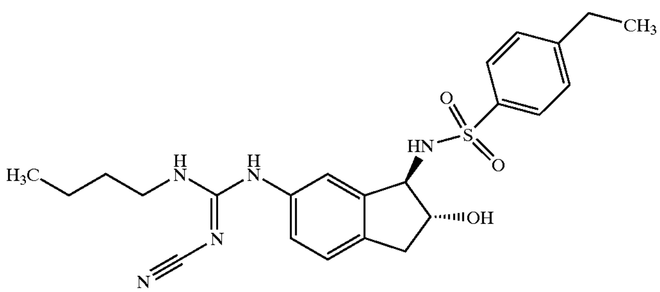 | 456 (M + H) |
EXAMPLE 118
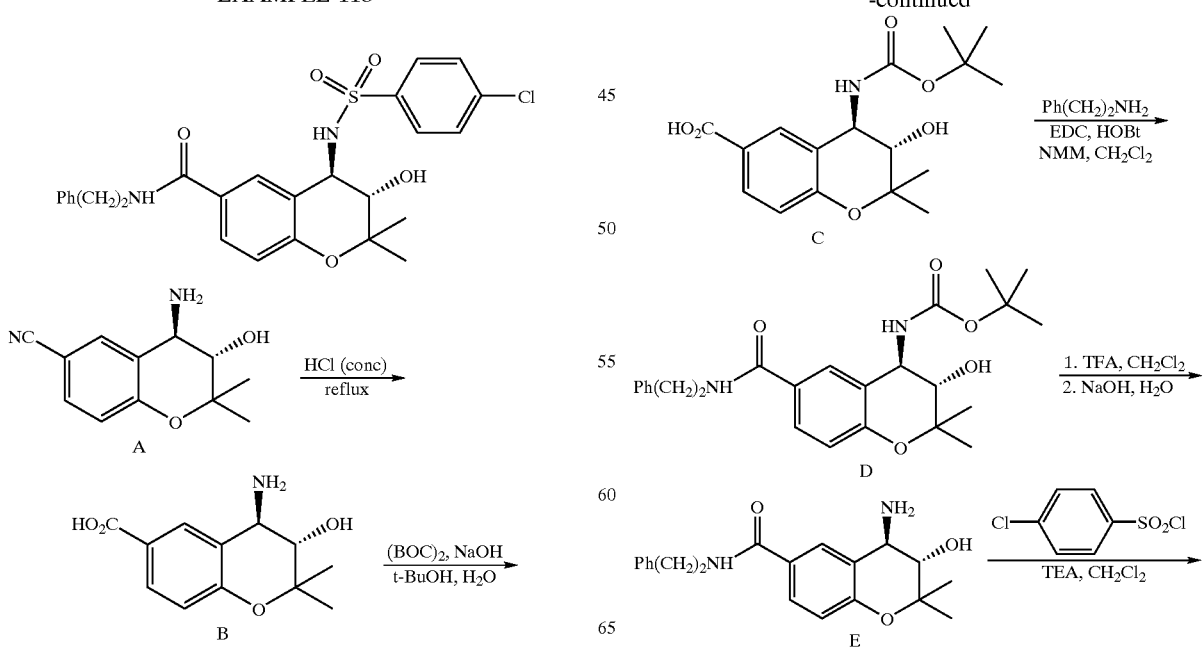

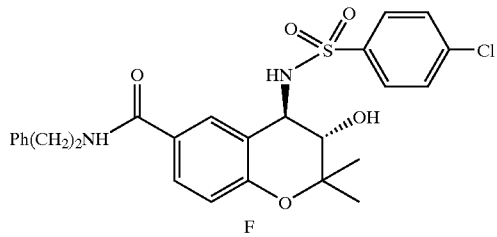

Preparation of A: trans-4-Amino-3,4-dihydro-2,2-dimethyl-6-cyano-2H-benzopyran methanesulfonate salt, see Example 1.

Preaaration of 3: A mixture of trans-4-Amino-3,4-dihydro-2,2-dimethyl-6-cyano-2H-benzopyran methanesulfonate salt (A,. 10.0 g, 26.9 mmol) and concentrated hydrochloric acid (100 mL) were refluxed for 9 h. A small aliquot of the mixture was partitioned between aqueous sodium hydroxide (1M) and ethyl acetate. TLC (10% methanol/dichloromethane) of the ethyl acetate layer indicated consumption of A. The mixture was allowed to cool to room temperature and allowed to stand overnight. The white precipitate which forms is collected by vacuum filtration. The precipitate was washed with hexanes, air dried, dried on a rotary evaporator at 70° C. and finally under vacuum to give 8.35 g (113% crude yield) of the title compound B as white solid. HPLC: 96.9% at 1.92 min. (YMC S5 ODS 4.6×50 mm Ballistic column) 10–90% methanol/water with 0.2% $H_3PO_4$ linear gradient over 4 min., 4 mL/min., UV Detection at 220 nm.

Preparation of C: Di-tert-butyl dicarbonate (6.8 mL, 34.5 mmol) was added to a room temperature solution of B (6.3 g, 23.0 mmol), aqueous sodium hydroxide (100 mL, 1M) and t-butanol (30 mL). The resulting mixture was stirred for 48 h. A small aliquot of the mixture was partitioned between aqueous hydrochloric acid (1M) and ethyl acetate. TLC (water/ammonium hydroxide/n-butanol, 1:1:8) of the ethyl acetate layer indicated the reaction was not complete. Additional aqueous sodium hydroxide (20 mL, 1M) and di-tert-butyl dicarbonate (3.8 g, 17.2 mmol) were added and the mixture was allowed to stir 6 h. TLC indicated the presence of B. More aqueous sodium hydroxide (30 mL, 1M) and di-tert-butyl dicarbonate (4.0 g, 18.3 mmol) were added and the mixture was allowed to stir overnight. The mixture was transferred to a separatory funnel and washed with hexanes (3X). The hexane extracts were combined and extracted with aqueous sodium hydroxide (1.0 M). The sodium hydroxide portions were combined and acidified to pH 3 with aqueous hydrochloric acid (1.0 M). The resulting solution was extracted with ethyl acetate. The ethyl acetate extracts were combined, washed with aqueous hydrochloric acid (1.0 M), water and brine, dried over anhydrous sodium sulfate and concentrated to provide 7.7 g (89%) of the title compound C as a yellow foam. LCMS: 96.4% at 3.235 min. (YMC S5 ODS 4.6×50 mm Ballistic column) 10–90% methanol/water with 0.1% TFA linear gradient over 4 min., 4 mL/min., UV Detection at 220 nm, M+H 338.

Preparation of D: 1-[3-(Dimethylamino)propyl]-3-ethylcarbodiimide hydrochloride (1.46 g, 7.59 mmol) was added to a room temperature solution of C (2.14 g, 6.33 mmol), 1-hydroxybenzotriazole hydrate (1.03 g, 7.59 mmol), phenethylamine (0.95 mL, 7.59 mmol) and N-methylmorpholine (2.1 mL, 19.0 mmol) in dimethylformamide (30 mL). After 6 h a small aliquot was partitioned between aqueous hydrochloric acid (1.0 M) and ethyl acetate. TLC (10% methanol/dichloromethane) indicated consumptionof C. The mixture was transferred to a separatory funnel, diluted with ethyl acetate, washed with aqueous hydrochloric acid (1.0 M), water and brine, dried over anhydrous sodium sulfate and concentrated to give a 2.98 g (100%) of the title compound D as a slightly yellow foam of sufficient purity to be used without further purification. LCMS: 98.9% at 3.82 min. (YMC S5 ODS 4.6×50 mm Ballistic column) 10–90% methanol/water with 0.1% TFA linear gradient over 4 min., 4 mL/min., UV Detection at 220 nm, M+H 441.

Preparation of a: Trifluoroacetic acid (10 mL) was added to a room temperature solution of D (2.95 g, 6.71 mmol) in dichloromethane (50 mL). After 3h a small aliquot was partitioned between aqueous sodium hydroxide (1M) and ethyl acetate. TLC (10% methanol/dichloromethane) indicated consumption of D. The reaction was concentrated in vacuo and the residue was partitioned between aqueous sodium.hydroxide (1.0 M) and ethyl acetate. The mixture was transferred to a separatory funnel, diluted with ethyl acetate, washed with aqueous sodium hydroxide (1.0 M), water and brine, dried over anhydrous sodium sulfate and concentrated onto enough silica gel such that a free flowing powder was obtained. The resulting powder was loaded onto a chromatography column prepacked with (10% tnethanol/dichloromethane). Elution with the same solvent provided 1.7 g (77%) of the title compound E as a white foam. LCMS: 98.8% at 3.04 min. (YMC S5 ODS 4.6×50 mm Ballistic column) 10–90% rmethanol/water with 0.1% TFA linear gradient over 4 min., 4 mL/min., UV Detection at 220 nm, M+H 341.

PreDaration of F: 4-Chlorobenzenesulfonyl chloride (0.014 g, 0.07 mmol) was added to a room temperature solution of E (0.012 g, 0.035 mmol) and triethylamine (0.012 mL, 0.088 mmol) in dichloromethane (0.5 mL) in a 16×100 mm test tube. The mixture was shaken gently overnight on a vortex genie. A mixed bed solid phase extraction cartridge (Worldwide Monitoring, CUMBQSP901, containing 1800 mg benzenesulfonic acid "BCX" atop 900 mg quaternary amine "QAX" with a hydroxide counter ion) was washed with methanol (20 mL) followed by dichloromethane (20 mL). The reaction mixture was diluted with dichloromethane (0.5 mL) and loaded onto the cartridge. The cartridge was eluted with dichloromethane ( 8 mL) collecting 2 fractions, followed by methanol (15 mL) collecting 3 fractions. The fraction containing the title compound was concentrated to provide 0.0122 g (68%). HPLC: 100% at 3.12 min. (YMC S5 ODS 4.6×50 mm Ballistic column) 40–90% mEthanol/water with 0.2% $H_3PO_4$ linear gradient over 4 min., 4 mL/min., UV Detection at 220 nm. Alternately purification could be performed by directly loading the reaction mixture onto a preparative TLC plate (20×20 cm, 1000 micron) and eluting with 5% methanol/dichloromethane to provide the title compound as a white powder. LCMS: 89% at 4.03 min. (YMC S5 ODS 4.6×50 mm Ballistic column) 10–90% mEthanol/water with 0.1% TFA linear gradient over 4 min., 4 mL/min., UV Detection at 220 nm, M+H 515.

The following compounds were synthesized by the procedures described in Example 118.

| Example | Structure | mass spec m/z |
|---|---|---|
| 119 | 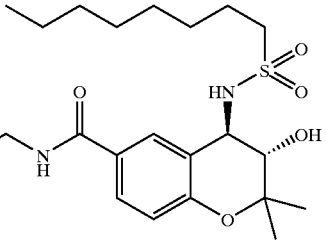 | 517 (M + H) |
| 120 | 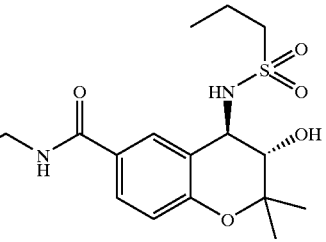 | 447 (M + H) |
| 121 | 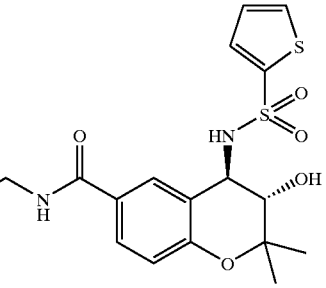 | 487 (M + H) |
| 122 | 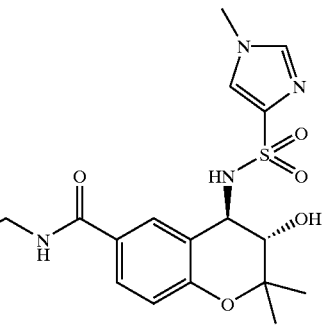 | 485 (M + H) |
| 123 | 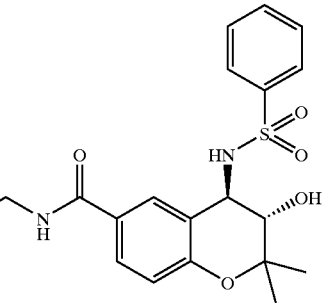 | 481 (M + H) |

| Example | Structure | mass spec m/z |
|---|---|---|
| 124 | (structure) | 531 (M + H) |
| 125 | (structure) | 531 (M + H) |
| 126 | (structure) | 583 (M + H) |
| 127 | (structure) | 549 (M + H) |

-continued
| Example | Structure | mass spec m/z |
|---|---|---|
| 128 | 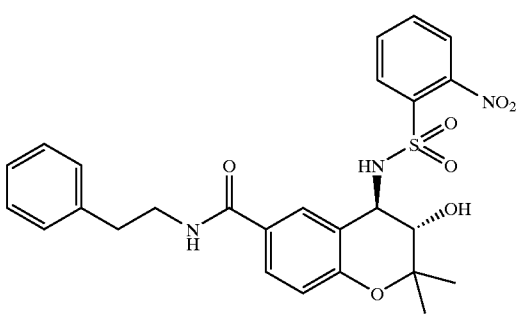 | 526 (M + H) |
| 129 | 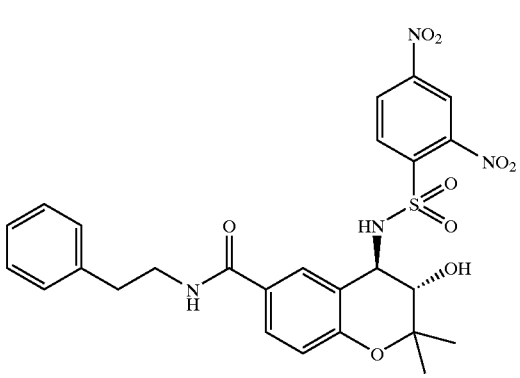 | 571 (M + H) |
| 130 | 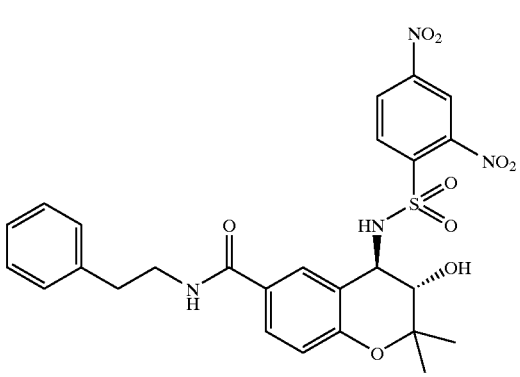 | 526 (M + H) |
| 131 | 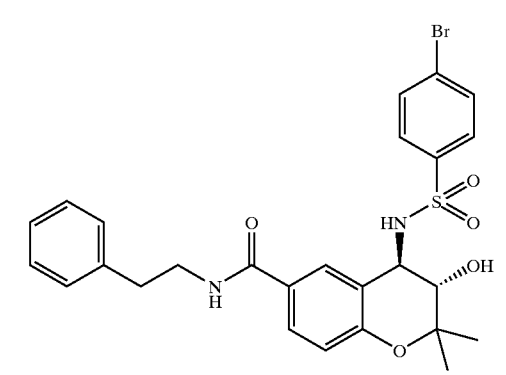 | 559 (M + H) |

-continued

| Example | Structure | mass spec m/z |
|---|---|---|
| 132 | 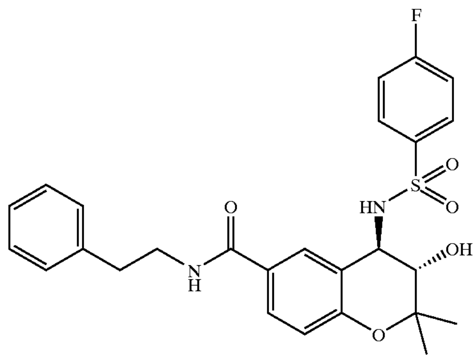 | 499 (M + H) |
| 133 | 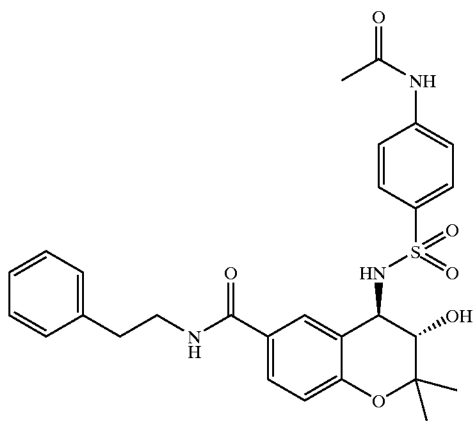 | 538 (M + H) |
| 134 | 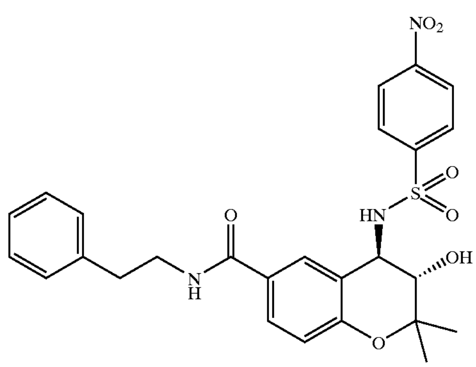 | 526 (M + H) |
| 135 | 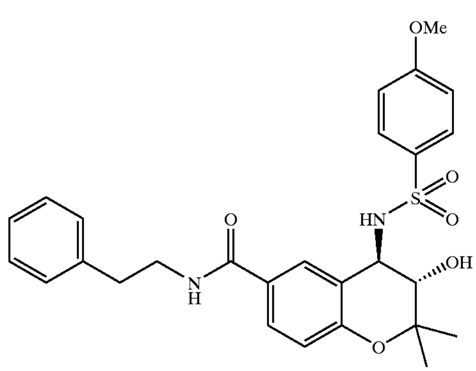 | 511 (M + H) |

-continued

| Example | Structure | mass spec m/z |
|---------|-----------|---------------|
| 136 | 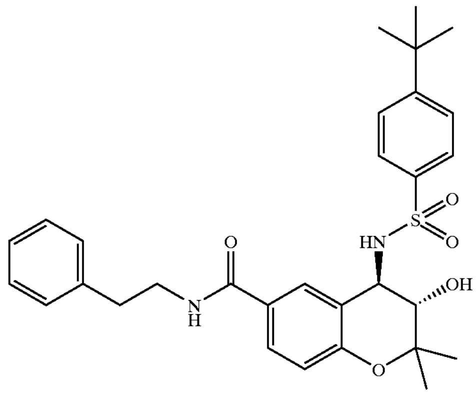 | 537 (M + H) |
| 137 | 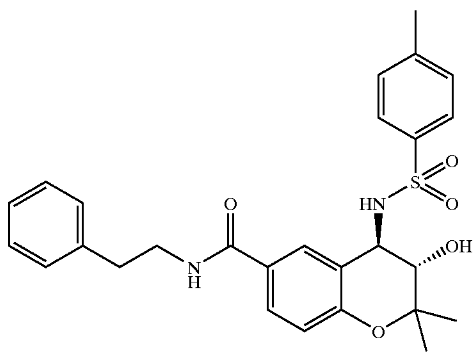 | 495 (M + H) |
| 138 | 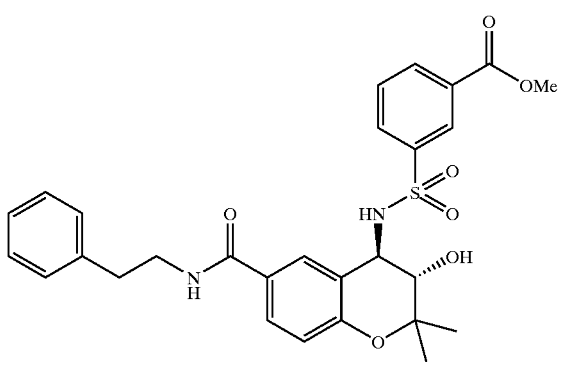 | 539 (M + H) |
| 139 | 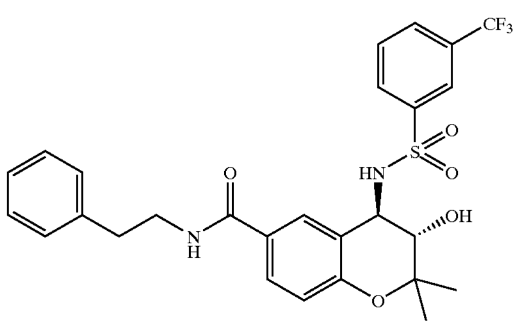 | 549 (M + H) |

-continued
| Example | Structure | mass spec m/z |
|---|---|---|
| 140 | 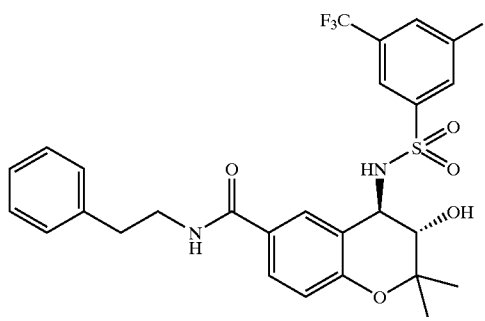 | 617 (M + H) |
| 141 | 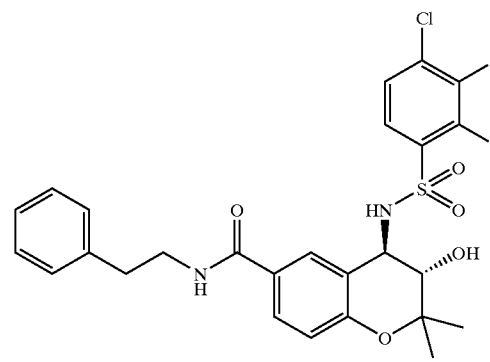 | 583 (M + H) |
| 142 | 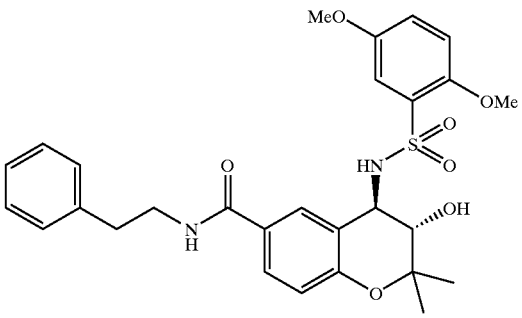 | 541 (M + H) |
| 143 | 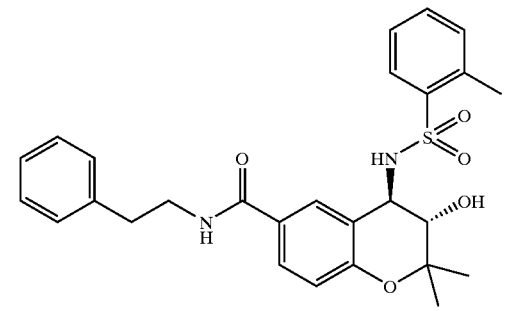 | 495 (M + H) |

-continued
| Example | Structure | mass spec m/z |
|---|---|---|
| 144 | 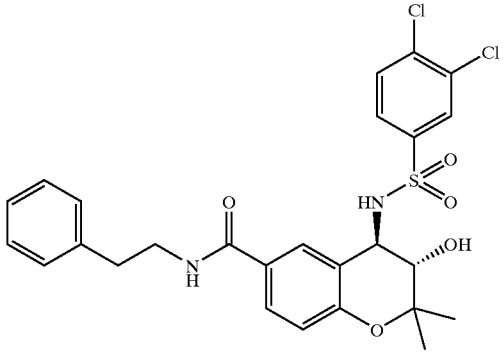 | 549 (M + H) |
| 145 | 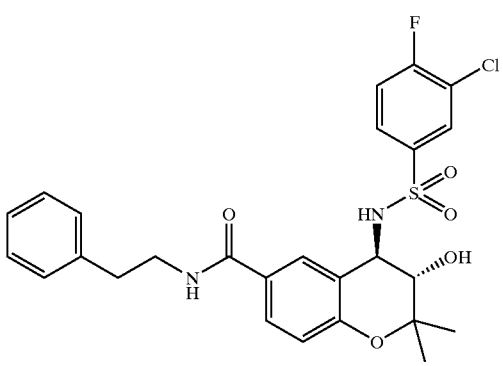 | 533 (M + H) |
| 146 | 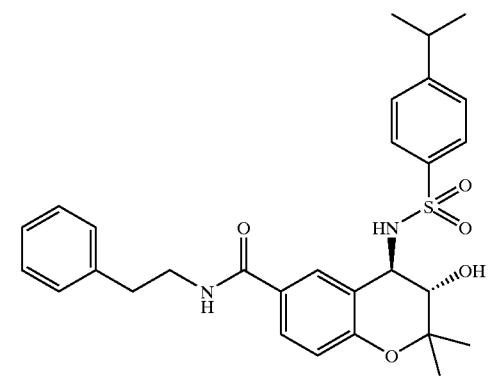 | 523 (M + H) |
| 147 | 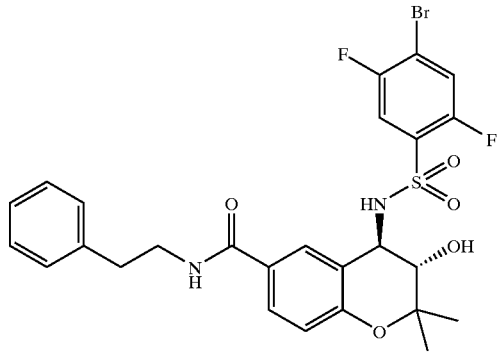 | 595 (M + H) |

-continued

| Example | Structure | mass spec m/z |
|---------|-----------|---------------|
| 148 | 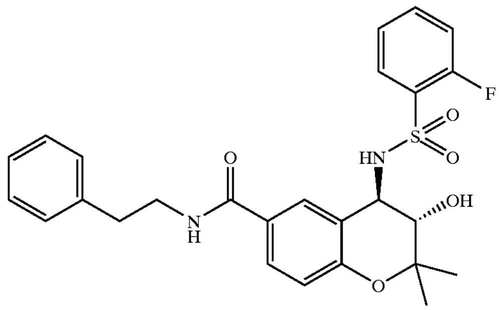 | 499 (M + H) |
| 149 | 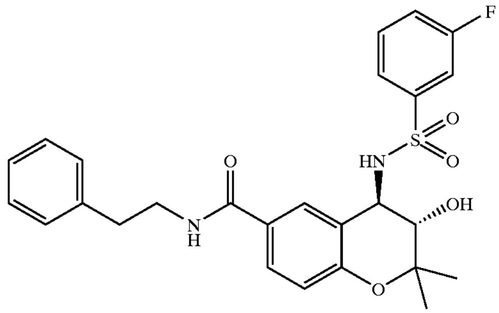 | 499 (M + H) |
| 150 | 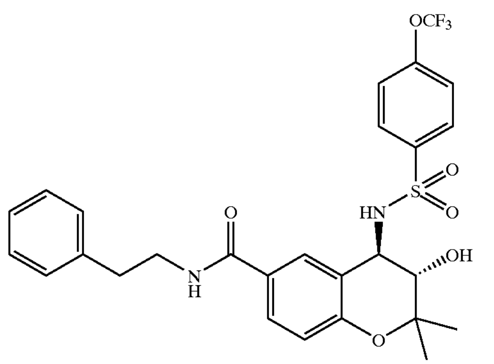 | 565 (M + H) |
| 151 | 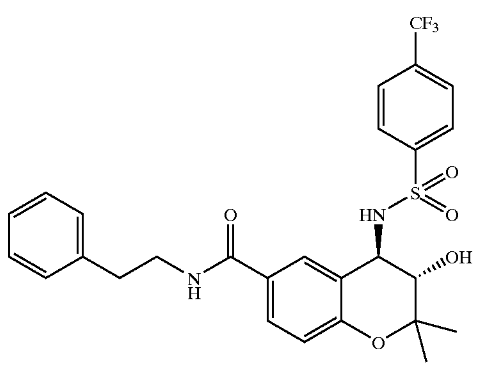 | 549 (M + H) |

-continued

| Example | Structure | mass spec m/z |
|---|---|---|
| 152 | 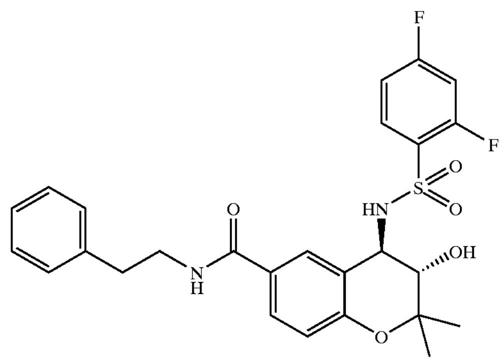 | 517 (M + H) |
| 153 | 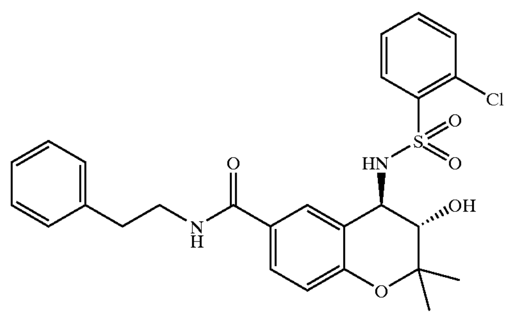 | 515 (M + H) |
| 154 | 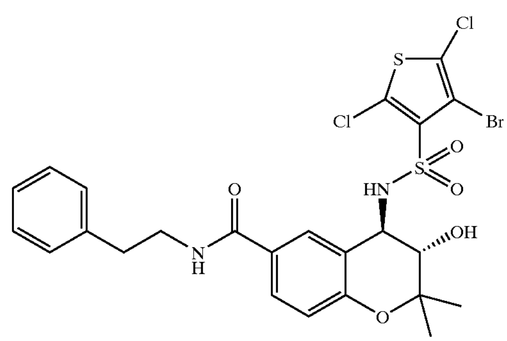 | 633 (M + H) |
| 155 | 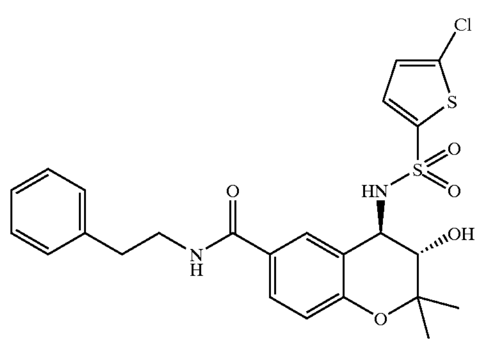 | 521 (M + H) |

-continued

| Example | Structure | mass spec m/z |
|---|---|---|
| 156 | 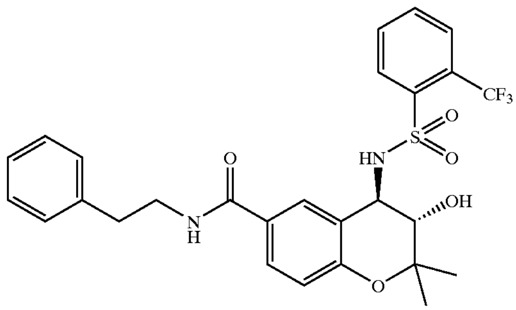 | 549 (M + H) |
| 157 | 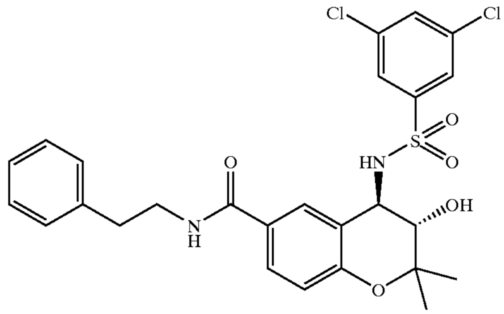 | 549 (M + H) |
| 158 | 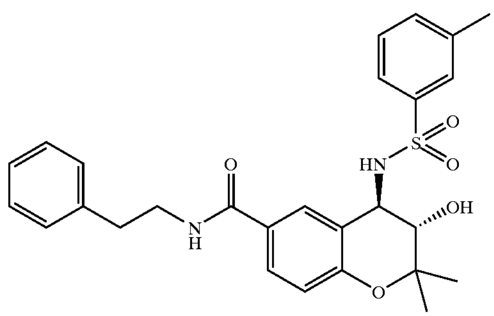 | 495 (M + H) |
| 159 | 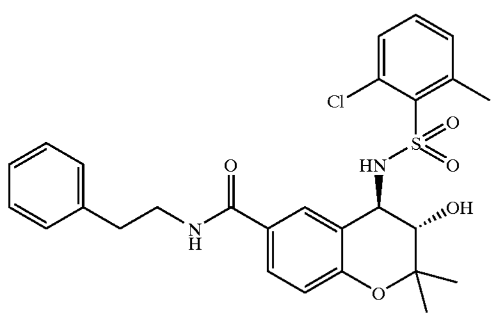 | 529 (M + H) |

-continued

| Example | Structure | mass spec m/z |
|---|---|---|
| 160 | 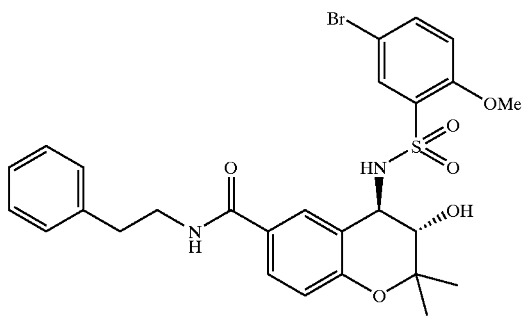 | 589 (M + H) |
| 161 | 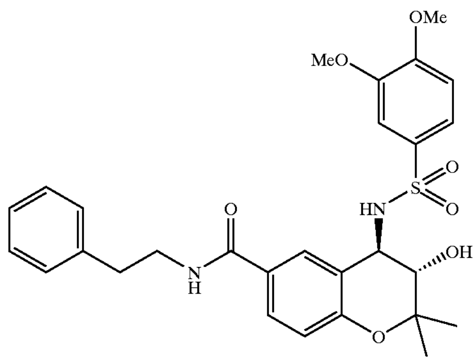 | 541 (M + H) |
| 162 | 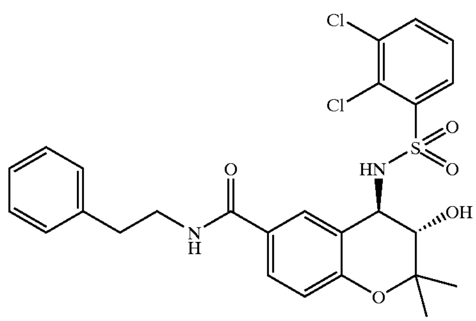 | 549 (M + H) |
| 163 | 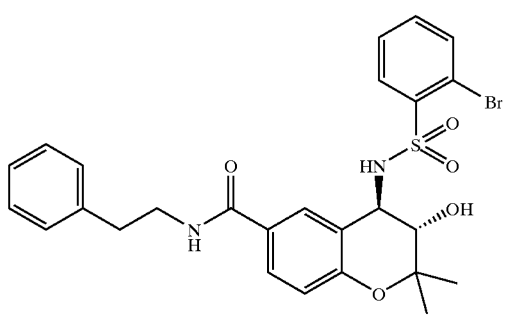 | 559 (M + H) |

-continued

| Example | Structure | mass spec m/z |
|---|---|---|
| 164 | 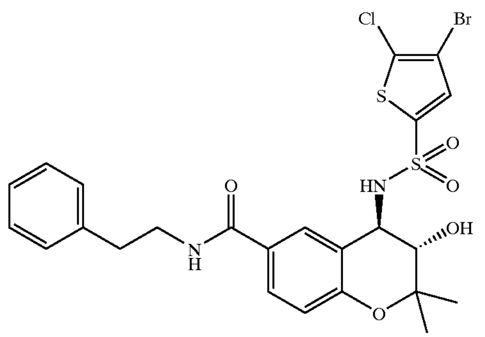 | 599 (M + H) |
| 165 | 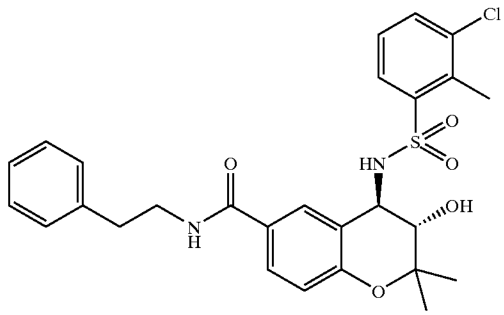 | 529 (M + H) |
| 166 | 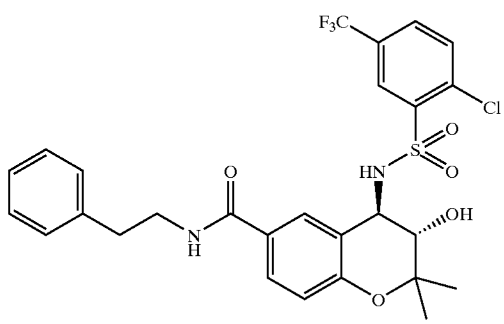 | 583 (M + H) |
| 167 | 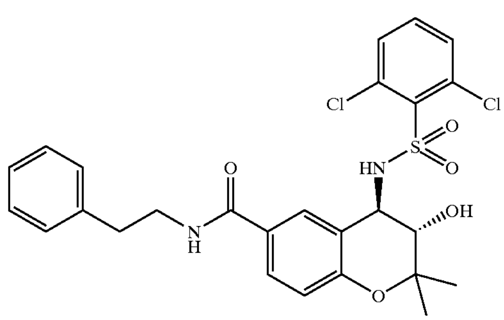 | 549 (M + H) |

-continued
| Example | Structure | mass spec m/z |
|---|---|---|
| 168 | 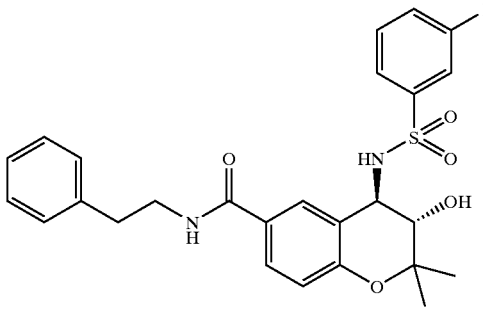 | 559 (M + H) |
| 169 | 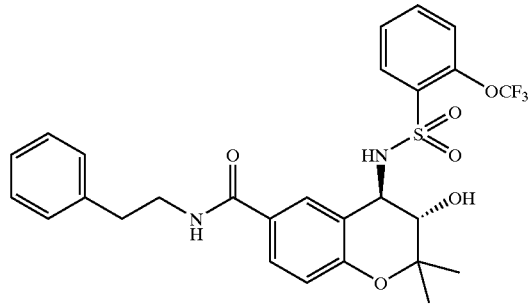 | 565 (M + H) |
| 170 | 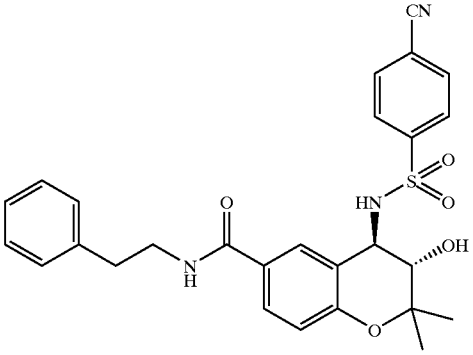 | 506 (M + H) |
| 171 | 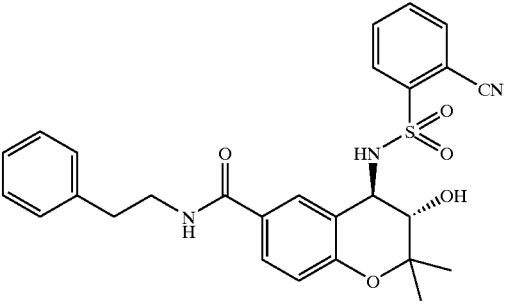 | 506 (M + H) |

-continued
| Example | Structure | mass spec m/z |
|---|---|---|
| 172 | 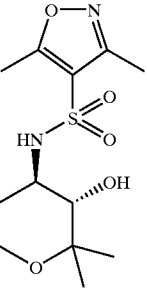 | 500 (M + H) |
| 173 | 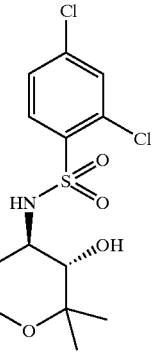 | 549 (M + H) |
| 174 | 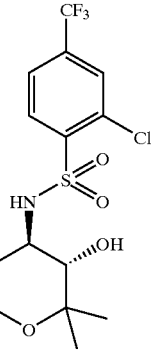 | 583 (M + H) |
| 175 | 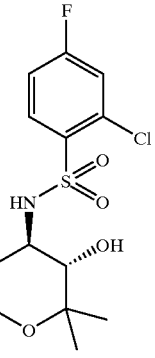 | 533 (M + H) |

-continued
| Example | Structure | mass spec m/z |
|---|---|---|
| 176 | 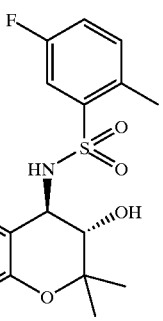 | 513 (M + H) |
| 177 | 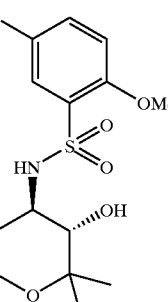 | 545 (M + H) |
| 178 | 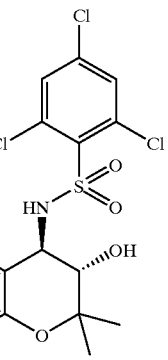 | 583 (M + H) |
| 179 | 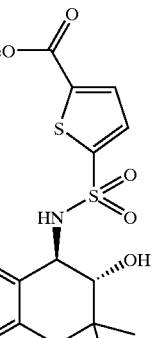 | 545 (M + H) |

-continued

| Example | Structure | mass spec m/z |
|---|---|---|
| 180 | 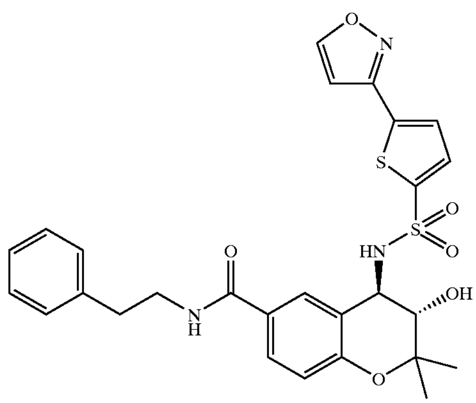 | 554 (M + H) |
| 181 | 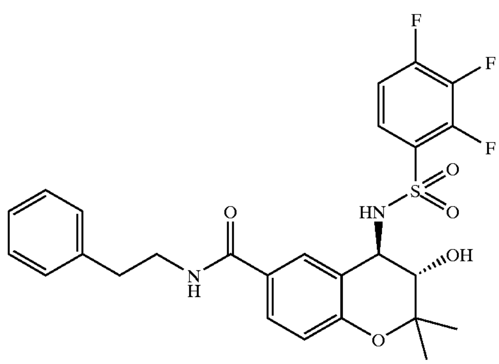 | 535 (M + H) |
| 182 | 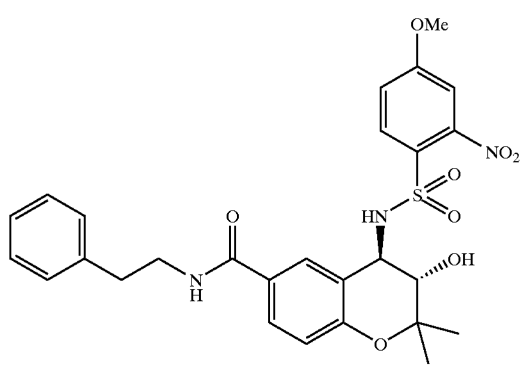 | 556 (M + H) |
| 183 | 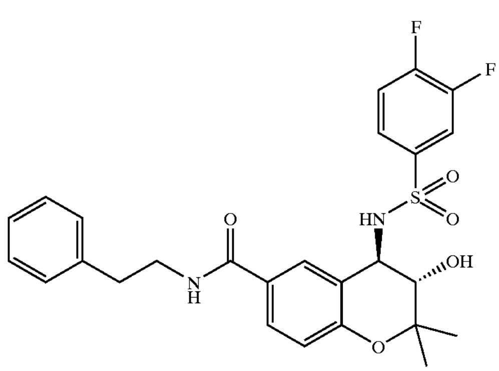 | 517 (M + H) |

-continued

| Example | Structure | mass spec m/z |
|---------|-----------|---------------|
| 184 | 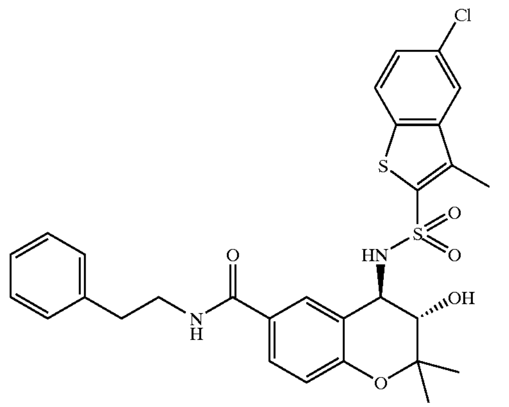 | 585 (M + H) |
| 185 | 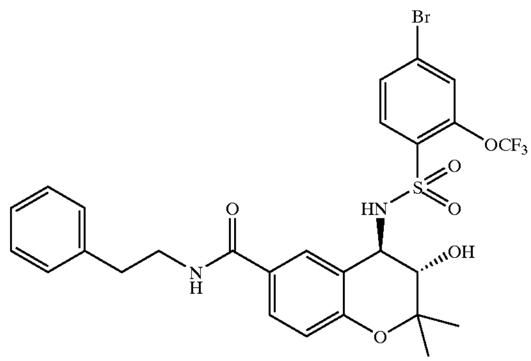 | 643 (M + H) |
| 186 | 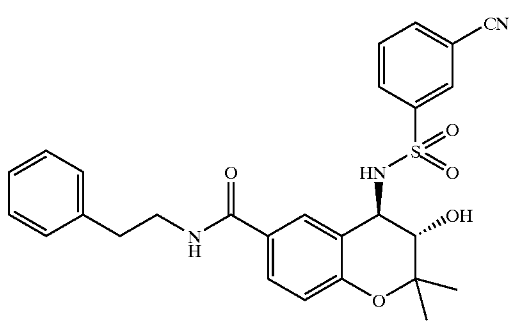 | 506 (M + H) |
| 187 | 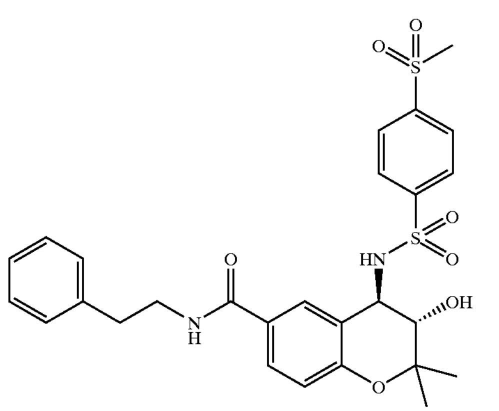 | 559 (M + H) |

-continued
| Example | Structure | mass spec m/z |
|---------|-----------|---------------|
| 188 | 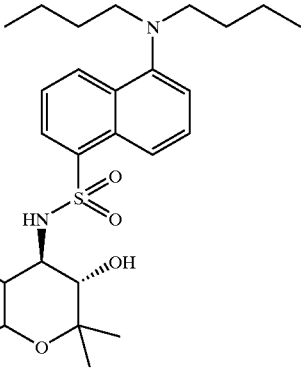 | 658 (M + H) |
| 189 | 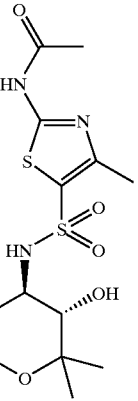 | 559 (M + H) |
| 190 | 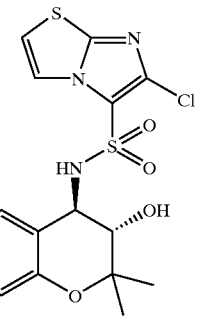 | 561 (M + H) |
| 191 | 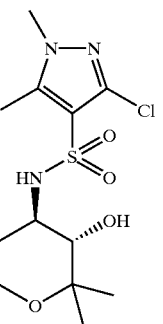 | 533 (M + H) |

-continued

| Example | Structure | mass spec m/z |
|---|---|---|
| 192 | 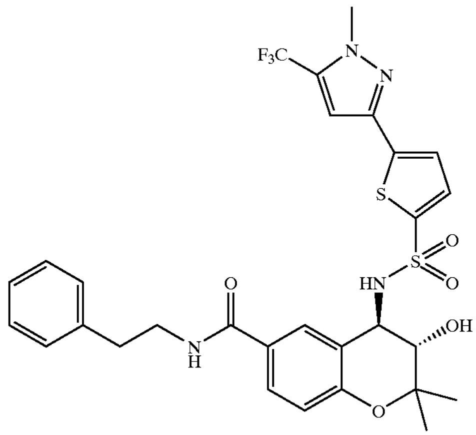 | 635 (M + H) |
| 193 | 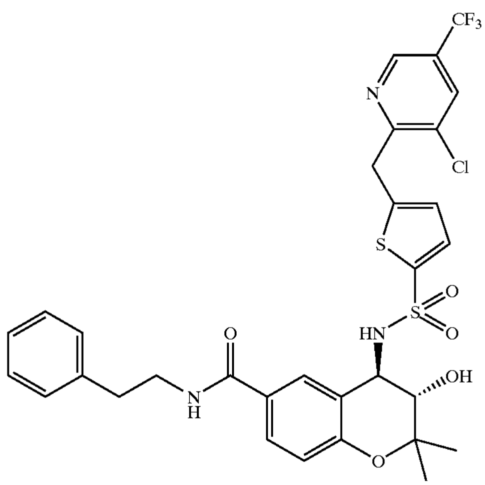 | 680 (M + H) |
| 194 | 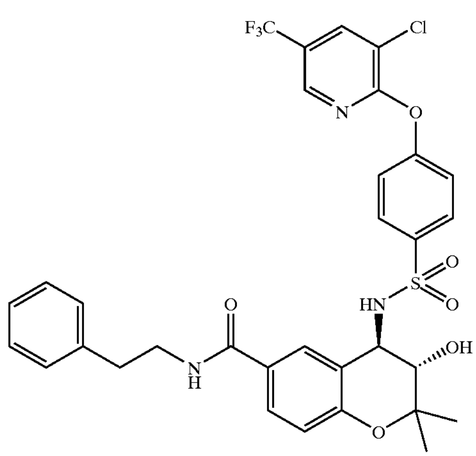 | 676 (M + H) |

-continued

| Example | Structure | mass spec m/z |
|---|---|---|
| 195 | 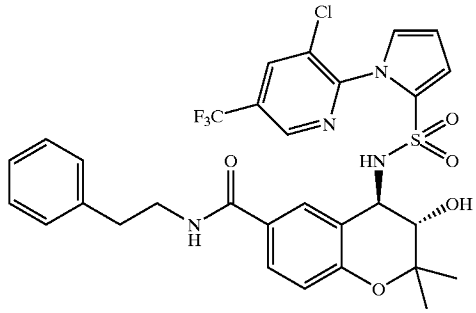 | 649 (M + H) |
| 196 | 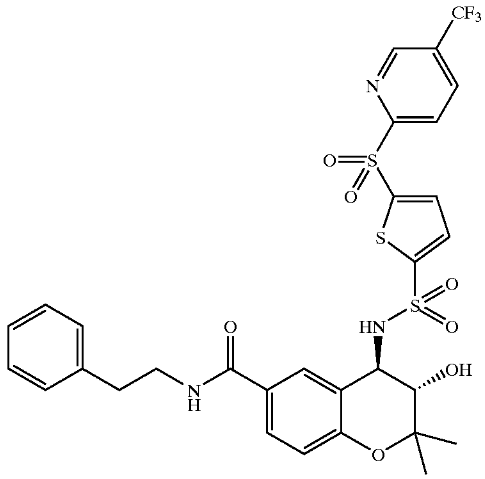 | 696 (M + H) |

EXAMPLE 197

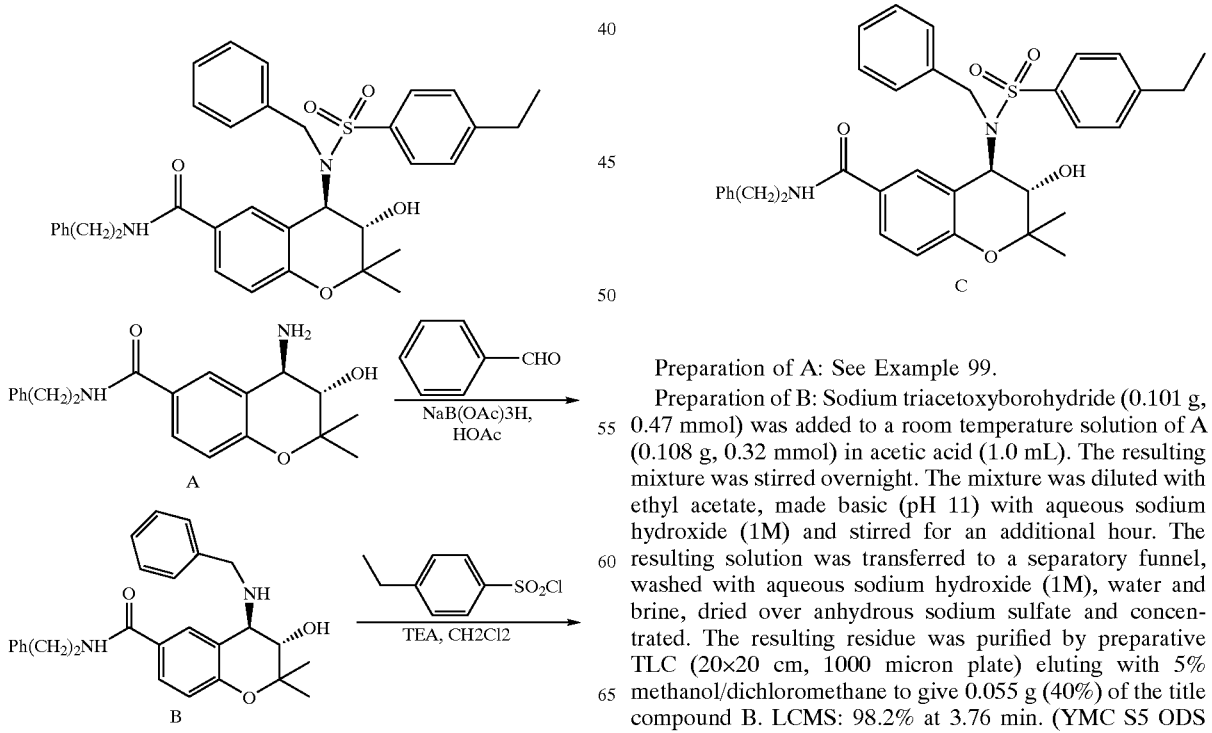

Preparation of A: See Example 99.

Preparation of B: Sodium triacetoxyborohydride (0.101 g, 0.47 mmol) was added to a room temperature solution of A (0.108 g, 0.32 mmol) in acetic acid (1.0 mL). The resulting mixture was stirred overnight. The mixture was diluted with ethyl acetate, made basic (pH 11) with aqueous sodium hydroxide (1M) and stirred for an additional hour. The resulting solution was transferred to a separatory funnel, washed with aqueous sodium hydroxide (1M), water and brine, dried over anhydrous sodium sulfate and concentrated. The resulting residue was purified by preparative TLC (20×20 cm, 1000 micron plate) eluting with 5% methanol/dichloromethane to give 0.055 g (40%) of the title compound B. LCMS: 98.2% at 3.76 min. (YMC S5 ODS 4.6×50 mm Ballistic column) 10–90% mEthanol/water with 0.1% TFA linear gradient over 4 min., 4 mL/min., UV Detection at 220 rum. M+H: 431.

Preparation of C: 4-Ethylbenzenesulfonyl chloride (0.38g, 0.19 mmol) was added to a room temperature solution of B (0.53 g, 0.12 mmol) and triethylamine (0.034 mL, 0.25 mmol) in dichloromethane (1 mL) and the mixture was stirred overnight. TLC (5% methanol/dichloromethane) indicated the reaction had not gone to completion. Additional triethylamine (0.04 mL, 0.28 mmol) and 4-ethylbenzenesulfonyl chloride (0.04g, 0.16 mmol) were added. TLC after 5 h indicated most of B was consumed. The mixture was loaded directly onto a preparative TLC plate (20×20 cm, 1000 micron) and eluted with 50% ethyl acetate/hexanes to give 0.608 g (82%) of the title compound C. LCMS: 99.5% at 4.34 min. (YMC S5 ODS 4.6×50 mm Ballistic column) 10–90% mEthanol/water with 0.1% TFA linear gradient over 4 min., 4 mL/min., UV Detection at 220 nm. M+H: 599.

The following compounds were synthesized by the procedures described in Example 178.

| Example | Structure | mass spec m/z |
|---|---|---|
| 198 | 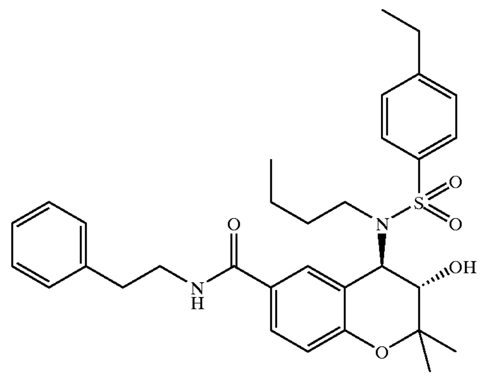 | 465 (M + H) |
| 199 | 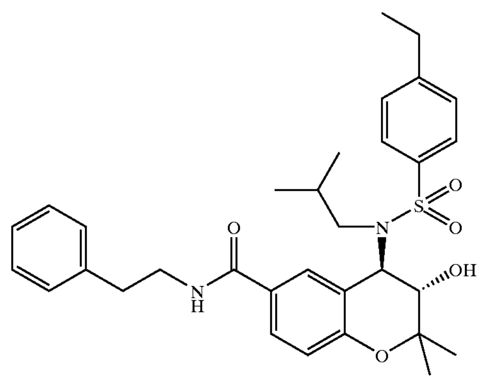 | 565 (M + H) |
| 200 | 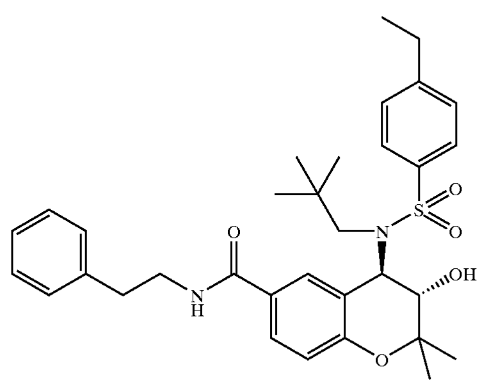 | 579 (M + H) |

-continued
| Example | Structure | mass spec m/z |
|---|---|---|
| 201 | 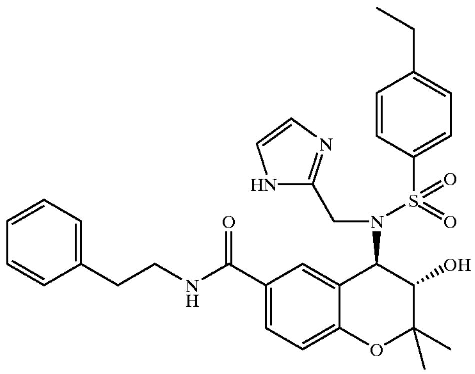 | 589 (M + H) |
| 202 | 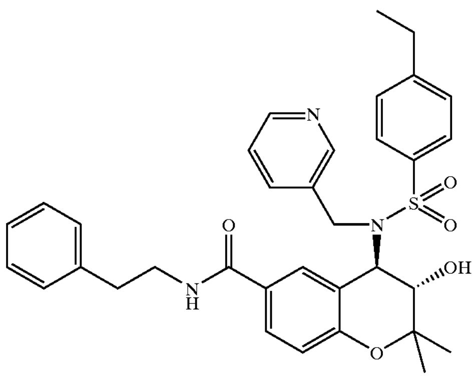 | 600 (M + H) |
| 203 | 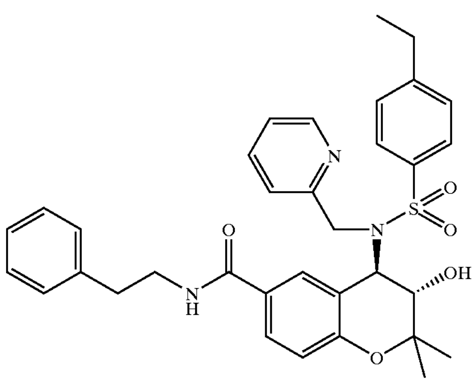 | 600 (M + H) |
EXAMPLE 204
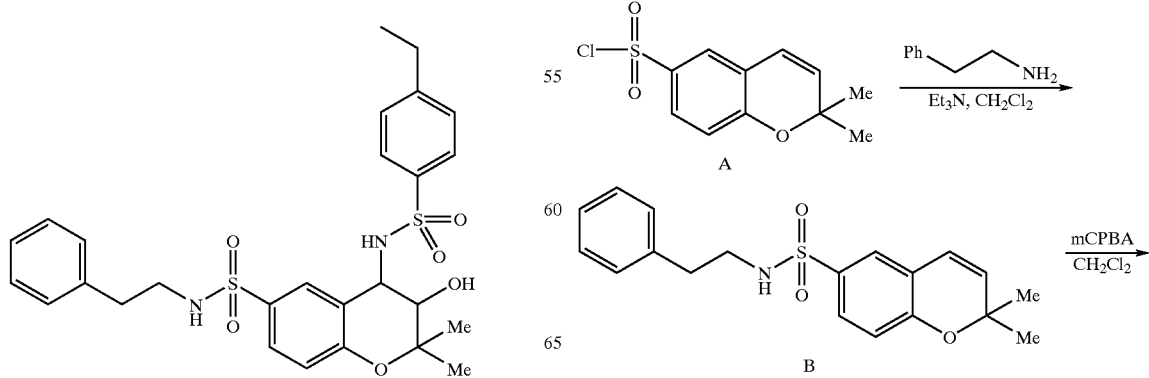
-continued

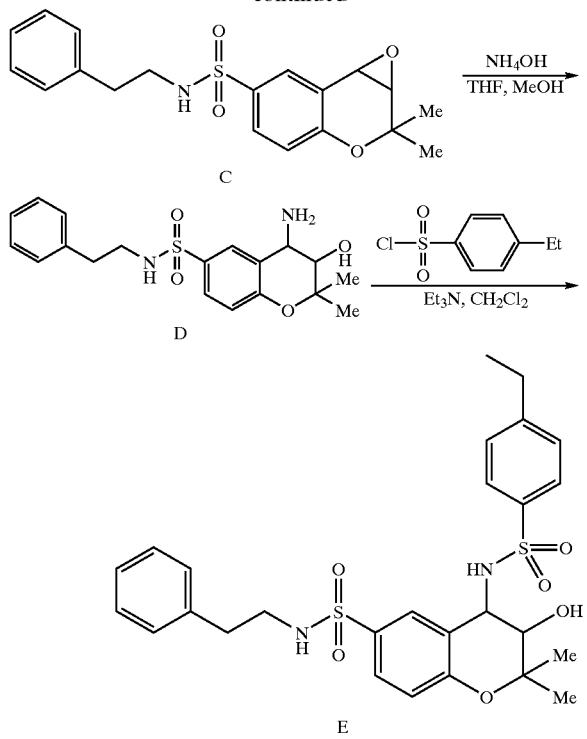

Preparation of A: The sulfonyl chloride may be prepared by procedures described in Ding, C. Z. *Syn. Comm.* 1996, 26, 4267–4273 and references cited therein.

Preparation of B: To a solution of the sulfonyl chloride A (3.9 mmol) in dichloromethane (12 mL) was added triethyl amine (7.8 mmol) followed by phenethylamine (5.8 mmol) and the mixture stirred at room temperature overnight after which TLC analysis showed no presence of A. The reaction mixture was quenched by addition of 2N aqueous hydrochloric acid and the aqueous layer extracted with dichloromethane. The organic layers were washed successively with saturated aqueous sodium bicarbonate, brine and dried over magnesium sulfate. Evaporation of the solvent followed by purification of the residue by column chromatography gave pure sulfonamide B (87%).

Preparation of C: To a solution of the sulfonamide B (2.7 mmol) in dichloromethane (20 mL) was added m-chloroperbenzoic acid (4 mmol, 82% purity with the rest being benzoic acid) and the mixture stirred at room temperature overnight when TLC indicated completion of the reaction. The reaction was quenched with saturated aqueous sodium bicarbonate solution, the organic layers separated, washed with brine and dried over sodium sulfate. The solvent was evaporated and the residue carried over directly to next step without any purification.

Preparation of D: The crude epoxy-sulfonamide C was dissolved in a mixture of THF (10 mL), ethanol (10 mL) and ammonium hydroxide solution (28–30%, 20 mL) and the solution heated in a sealed tube to 45–60° C. until TLC indicated the complete consumption of epoxide C (5–6 hrs). The reaction was cooled where upon a part of the aminoalcohol D crystallized out. The crystallized product was filtered, washed with 10% ethyl acetate-hexane and air-dried. The washings were combined with the filtrate, the organic layers separated, dried over sodium sulfate and evaporated. Purification of the residue by silica gel column chromatography gave additional amounts of pure amino alcohol D (71%).

Preparation of E: To a solution of the aminoalcohol D (0.6 mmol) in dichloromethane (5 mL) was added triethyl amine (1.2 mmol) followed by 4-ethylbenzenesulfonyl chloride (0.9 mmol) and the mixture stirred at room temperature overnight when TLC indicated complete consumption of D. The reaction was quenched with 2N aqueous hydrochloric acid and the aqueous layer extracted with dichloromethane. The combined organic layers were washed successively with saturated aqueous sodium bicarbonate solution, brine and dried over sodium sulfate. Evaporation of the solvent followed by purification of the residue by silica gel column chromatography gave pure bis-sulfonamide E (82%). Mass Spec (M+H) 545, (2M+NH$_4$=1106.5); HPLC conditions:

Column=YMC S5 C18 4.6×50 mm, solvent=10 to 90% methanol in water with 0.2% phosphoric acid over a 4 min. gradient, UV detection at 220 nm, retention time= 4.1 min.

The following compound was synthesized by the procedures described in Example 204.

| Example | Structure | mass spec m/z |
|---|---|---|
| 205 | 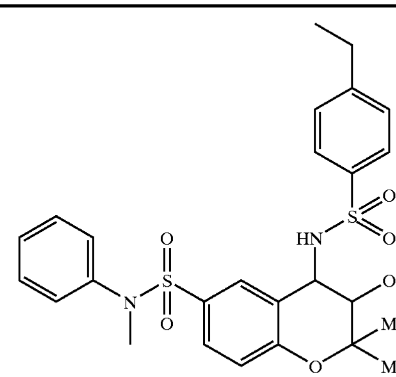 | 531 (M + H) |

EXAMPLE 206

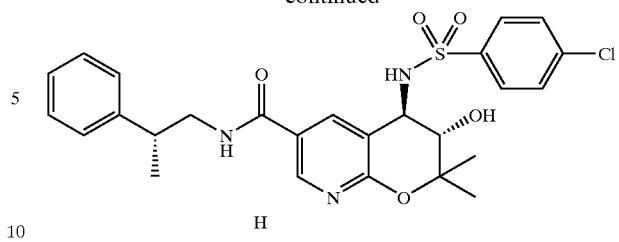

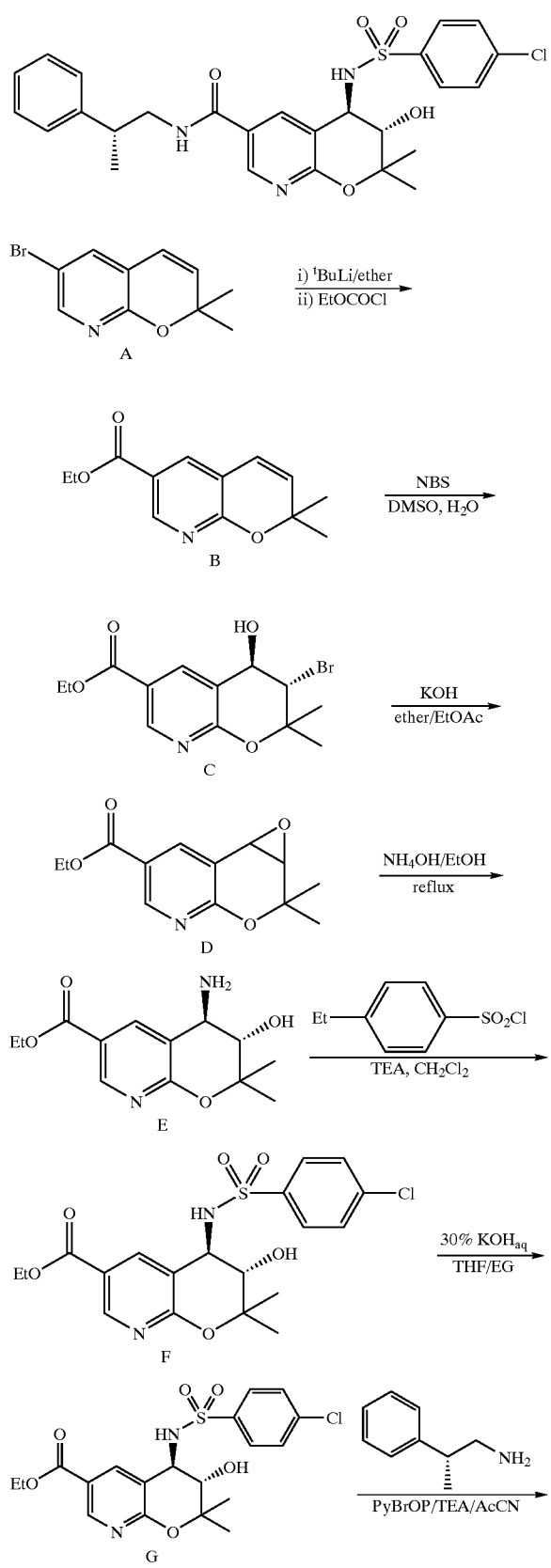

Preparation of A: 6-Bromo-2,2-dimethyl-2H-pyrano-[2,3b]-pyridine was prepared from commercially available 2-S Methoxypyyridine in 3 steps as described in Barger, T. M.; Dulworth, J. K.; Kenny, M. T.; Massad, R.;. Daniel, J. K.; Wilson, T.; Sargent, R. N.; *J. Med. Chem.*, 1986; 29, 1590 and Evans, J. M.; Stemp, G.; *Syn. Comm.*, 1988, 18, 1111.

Preparation of B: To a vigorously stirred slurry of 6-Bromo-2,2-dimethyl-2H-pyrano-[2,3b]-pyridine (A, 3.45 g, 14.4 mmol) in anhydrous ether/toluene (30/60 mL) at −100° C. under inert atmosphere was added a solution of tert-butyl lithium dropwise via syringe (9.8 mL, 16.7 mmol, 1.7 M solution in pentane). The slurry was maintained below −70° C. for 1 h then ethylchloroformate (1.6 mL, 16.8 mmol) was added dropwise and the reaction allowed to reach ambient temperature as the cooling bath warmed. Saturated aqueous sodium bicarbonate (20 mL) was added to the yellow slurry and the reaction mixture transferred to a separatory funnel. The aqueous phase was extracted with ethylacetate (2×50 mL) and the combined organic portions washed successively with saturated sodium chloride (2×50 mL) and water (50 mL), dried over sodium sulfate, decanted and concentrated under reduced pressure yielding a crude yellow oil. Purification by flash column chromatography on silica gel using hexane, ethylacetate (6:1) as eluent gave title compound B as a white solid (1.82 g, 50%). HPLC: 91% at 3.64 min. (YMC S5 ODS 4.6×50 mm Ballistic column) 10–90% methanol/water with 0.2% $H_3PO_4$ linear gradient over 4 min., 4 mL/min., UV Detection at 220 nm. HNMR: $CDCl_3$ 1.31,t,J=7.2 Hz (3H); 1.47,s(6H); 4.29,q,J=7.1Hz (2H); 5.65,d,J=9.8 Hz (1H); 6.26,d,J=9.8 Hz (1H); 7.79,d, J=2.3 (1H); 8.60,d,J=2.4 Hz (1H).

Preparation of C: At 20° C., recrystallized N-bromosuccinimide (2.78 g, 15.6 mmol) was added in 3 equal portions, 3 minutes apart, to a stirred solution of ethyl-6-carboxy-2,2-dimethyl-2H-pyrano-[2,3b]-pyridine (B, 1.82 g, 7.81 mmol) in dimethylsulfoxide/water (27/16 mL). After 3 h the reaction mixture was poured into water (200 mL) and extracted-with ethylacetate (3×50 mL). The combined organic portions were washed with saturated sodium chloride (2×50 mL), dried over sodium sulfate, decanted and concentrated under reduced pressure yielding a pale yellow solid. The crude material was purified by silica gel column chromatography to remove the small amount of 3,4-dibromo byproduct using hexane, ethylacetate (2:1 to 1:1 gradient) as eluent yielding bromohydrin C as a white solid (2.00 g, 78%). HPLC: 100% at 3.42 min. (YMC S5 ODS 4.6×50 mm Ballistic column) 10–90% methanol/water with 0.2% $H_3PO_4$ linear gradient over 4 min., 4 mL/min., UV Detection at 220 nm. HNMR: $CDCl_3$ 1.19, t, J=7.1 Hz (3H); 1.32, s (1H); 1.43, s (6H); 4.07, d, J=9.4 Hz (2H); 4.31, q, J=5.4 Hz (2H); 4.90, d, J=9.6 Hz (1H); 8.42, dd, J=2.4 and 1.1 Hz (1H); 8.77, d, J=1.8 Hz (1H).

Preparation of D: Potassium hydroxide pellets (1.48 g, 26.3 mmol) were added to a stirred solution of ethyl-6-carboxy-trans-4-hydroxy-3-bromo-3,4-dihydro-2,2-dimethyl-2H-pyrano-[2,3b]-pyridine (1.56 g, 4.74 mmol) in ether/ethylacetate (30/10 mL) at ambient temperature. After 4 h the slurry was filtered through a sintered glass funnel and the solvents removed in vacuo yielding epoxide D (1.03 g, 87%) as a white powder. HPLC: 88% at 3.11 min. (YMC S5 ODS 4.6×50 mm Ballistic column) 10–90% methanol/water with 0.1% TFA linear gradient over 4 min., 4 mL/min., UV Detection at 220 nm. HNMR: $CDCl_3$ 1.40,s (3H); 1.40, t, J=7.1 Hz (3H); 3.59, d, J=4.2 Hz (1H); 4.01, d, J=4.2 Hz (1H); 4.39, q, J=7.1 Hz (2H); 8.33, d, J=2.4 Hz (1H); 8.85, d, J=2.2 Hz (1H).

Preparation of E: Ethyl-6-carboxy-3,4-epoxide-3,4-dihydro-2,2-dimethyl-2H-pyrano-[2,3b]-pyridine (1.34 g, 5.36 mmol) was dissolved in ethanol (15 mL). Concentrated ammonium hydroxide (15 mL) was added and the solution heated to 80° C. under positive pressure of nitrogen. Two further aliquots of 5 mL ammonium hydroxide were added at 15 minute intervals and the solution maintained at 80° C. for a further 4 h. On cooling, the solvents were removed and the white solid redissolved in dichloromethane (100 mL) and washed with water (3×50 mL). The organic phase was dried over sodium sulfate, decanted and the dried in vacuo yielding a white solid product E (1.39 g, 97%) which was sufficiently pure to be used without further purification. HPLC: 92% at 1.97 min. (YMC S5 ODS 4.6×50 mm Ballistic column) 10–90% methanol/water with 0.1% TFA linear gradient over 4 min., 4 mL/min., UV Detection at 220 nm.

Preparation of F: To a solution of ethyl-6-carboxy-trans-4-amino-3-hydroxy-3,4-dihydro-2,2-dimethyl-2H-pyrano-[2,3b]-pyridine (E, 1.39 g, 5.23 mmol) in dichloromethane/triethylamine (15 mL/2 mL) was added 4-ethylbenzenesulfonyl chloride (1.28 g, 6.27 mmol) dropwise at ambient temperature. After 2 h a further 0.5 mL of TEA was added and the reaction mixture stirred for 12 h. The volume of dichloromethane was reduced under reduced pressure and the crude solution loaded directly onto a silica gel column and eluted with hexane/ethylacetate/methanol (2:2:1) yielding F as a white solid (1.18 g, 52%). HPLC: 89% at 3.98 min. (YMC S5 ODS 4.6×50 mm Ballistic column) 40–90% methanol/water with 0.2% $H_3PO_4$ linear gradient over 4 min., 4 mL/min., UV Detection at 220 nm. HNMR: $CDCl_3$ 1.27,s(3H); 1.29, t, J=7.6 Hz (3H); 1.37, t, J=7.1 Hz (3H); 1.56, s(3H); 2.76, q, J=7.6 Hz (2H); 3.72, d, J=9.5 Hz (1H); 4.31, q, J=7.1 Hz (2H); 4.33, d, J=7.4 Hz (1H); 7.40, d, J=8.1 Hz (2H); 7.86, s(1H); 7.90, d, J=8.1 Hz (2H); 8.70, s(1H).

Preparation of G: A solution of ethyl-6-carboxy-trans-N-[4-ethylphenylsulfonyl]-4-amino-3-hydroxy-3,4-dihydro-2,2-dimethyl-2H-pyrano-[2,3b]-pyridine (F, 477 mg, 1.10 mmol) in ethylene glycol/tetrahydroduran (6.6/2.2 mL) and aqueous potassium hydroxide (6.6 mL, 30% by weight) was heated to 100° C. for 12 h. The cooled solution was diluted with water (ca. 200 mL), the pH adjusted to 4–5 with 5% hydrochloric acid and extracted successively with dichloromethane (3×50 mL) and ethylacetate (2×50 mL). The combined organic portions were dried over sodium sulfate, decanted and the solvents removed. G was obtained as a pale brown powder (518 mg, 116%) sufficiently pure to be used without further purification. HPLC: 93% at 3.53 min. (YMC S5 ODS 4.6×50 mm Ballistic column) 10–90% methanol/water with 0.2% $H_3PO_4$ linear gradient over 4 min., 4 mL/min., UV Detection at 220 nm.

Preparation of H: To a solution of 6-carboxy-trans-N-[4-ethylphenylsulfonyl]-4-amino-3-hydroxy-3,4-dihydro-2,2-dimethyl-2H-pyrano-[2,3b]-pyridine (G, 25 mg, 0.062 mmol) in acetonitrile (2 mL) containing TEA (3 drops) was added bromo-tris-pyrrolidinophosphonium hexafluorophosphate (31 mg, 0.066 mmol). After 5 min., (S)-2-phenyl-1-propylamine (8 mg, 1 drop) was added and the resulting solution stirred at ambient temperature for 12 h. The crude reaction mixture was purified directly by preparative HPLC (YMC PACK S5 ODSA 20×100 mm column Reversed phase C18) 23–90% methanol/water with 0.1% TFA linear gradient over 10 min. 5 min. hold time, 20 mL/min., UV Detection at 220 nm yielding the TFA salt of H as a white amorphous solid (18.4 mg, 47%). HPLC: 97% at 4.24 min. (YMC S5 ODS 4.6×50 mm Ballistic column) 10–90% methanol/water with 0.2% $H_3PO_4$ linear gradient over 4 min., 4 mL/min., UV Detection at 220 nm. LCMS: 97% at 3.90 min. (YMC S5 ODS 4.6×50 mm Ballistic column) 10–90% methanol/water with 0.1% TFA linear gradient over 4 min., 4 mL/min., UV Detection at 220 rum, M+1 524. HNMR: CDCl 1.06, s(3H); 1.09, t, J=7.6 Hz (3H); 1.12, d, J=7.0 Hz (3H); 1.26, s(3H); 2.56, q, J=7.6 Hz (2H); 2.91, m(1H); 3.32, m(2H); 3.38, d, J=8.9 Hz (1H); 4.21, dd, J=8.7 and 0.8 Hz (1H); 7.06, m (4H); 7.21, d, J=8.3 Hz (2H); 7.67, d, J=7.9 Hz (2H); 7.91, m (1H); 8.14, s (1H).

The following compounds were synthesized by the procedures described in Example 206.

| Example | Structure | mass spec m/z |
|---|---|---|
| 207 | 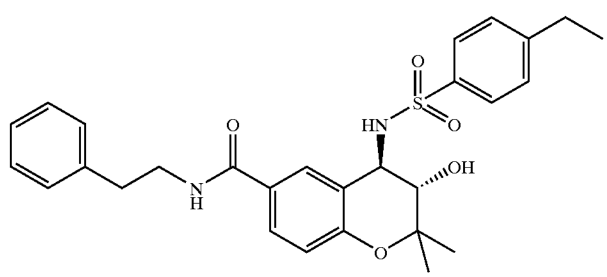 | 510 (M + H) |

-continued

| Example | Structure | mass spec m/z |
|---------|-----------|---------------|
| 208 | 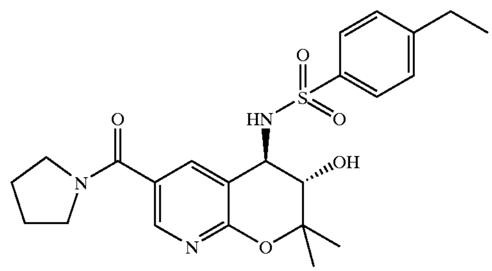 | 460 (M + H) |
| 209 | 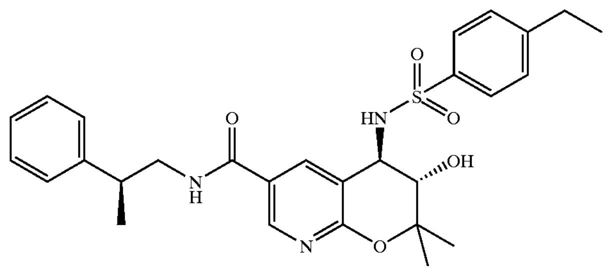 | 524 (M + H) |
| 210 | 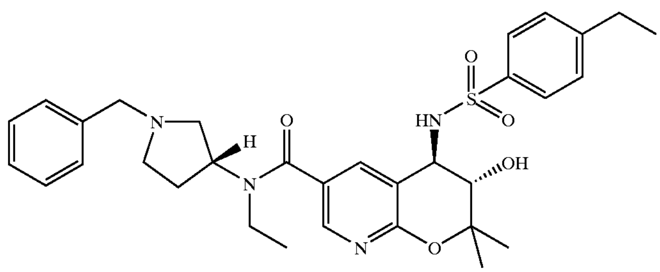 | 593 (M + H) |
| 211 | 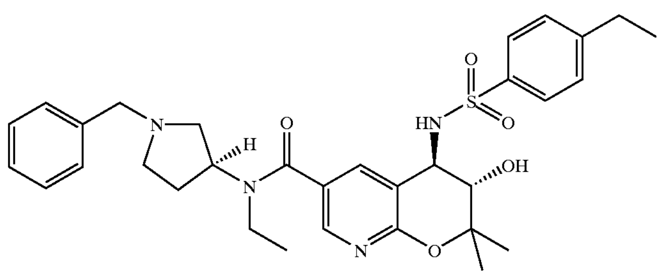 | 593 (M + H) |
| 212 | 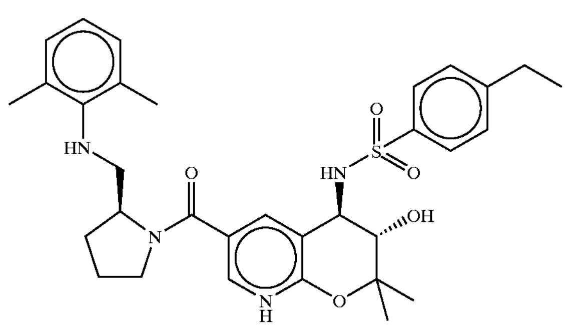 | 593 (M + H) |

-continued

| Example | Structure | mass spec m/z |
|---|---|---|
| 213 | 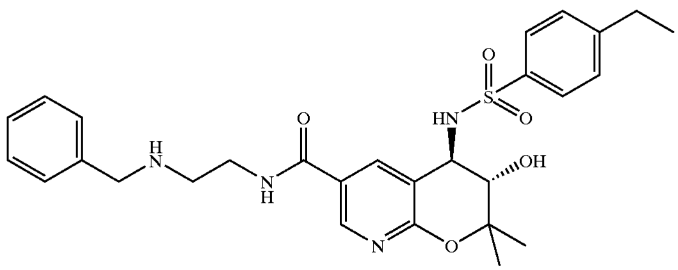 | 539 (M + H) |
| 214 | 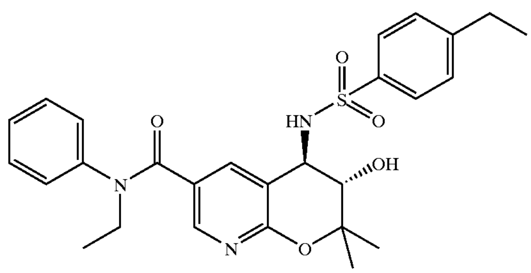 | 510 (M + H) |
| 215 | 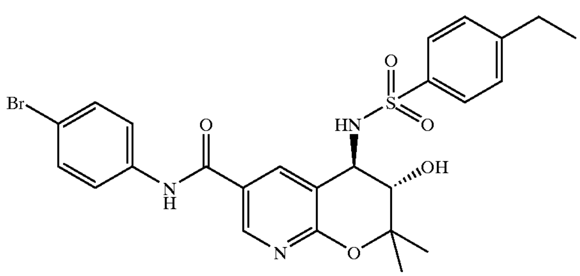 | 560 (M + H) |
| 216 | 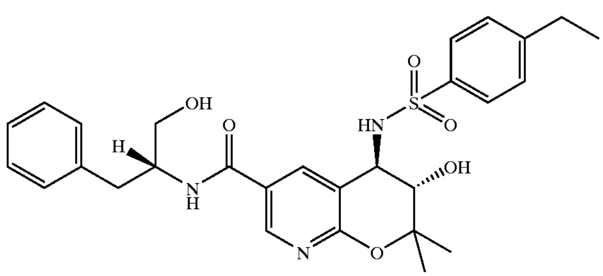 | 540 (M + H) |
| 217 | 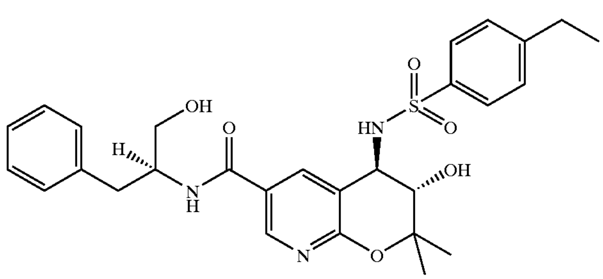 | 540 (M + H) |

-continued

| Example | Structure | mass spec m/z |
|---|---|---|
| 218 | 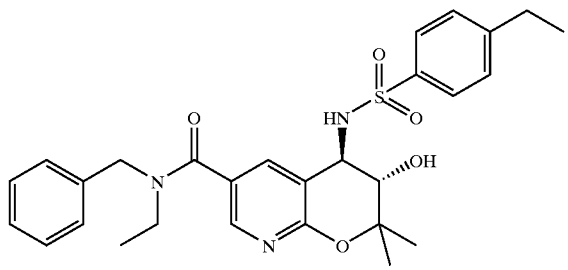 | 524 (M + H) |
| 219 | 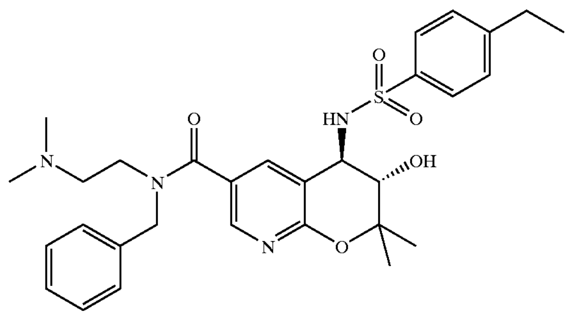 | 567 (M + H) |
| 220 | 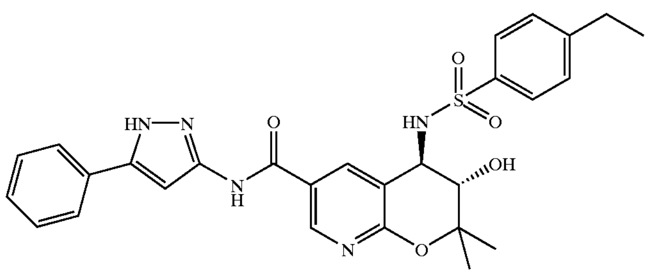 | 548 (M + H) |
| 221 | 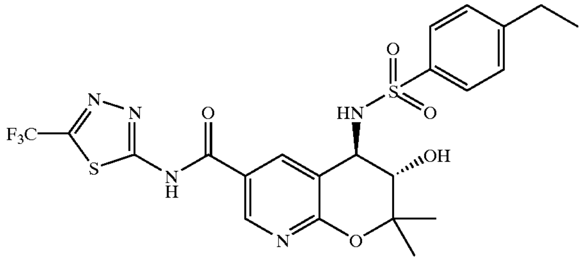 | 558 (M + 1) |
| 222 | 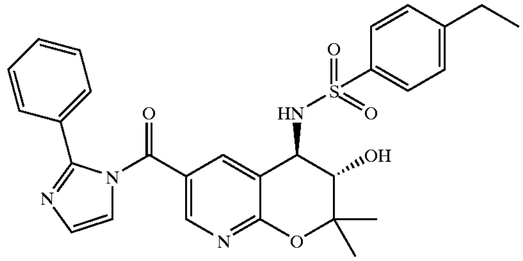 | 535 (M + 1) |

-continued

| Example | Structure | mass spec m/z |
|---|---|---|
| 223 | 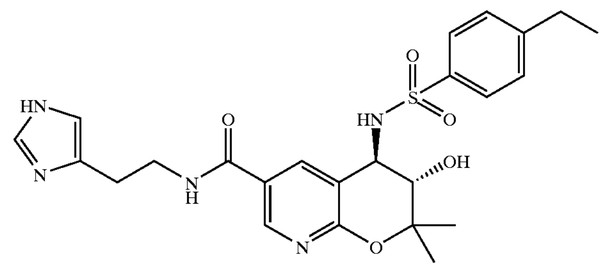 | 500 (M + 1) |
| 224 | 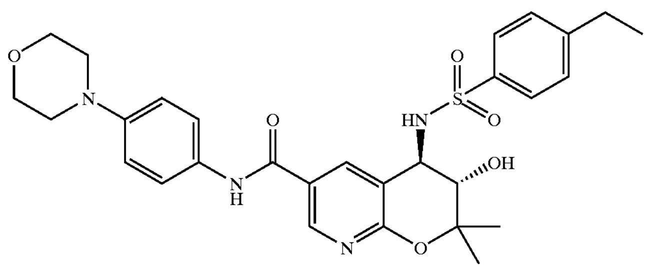 | 567 (M + 1) |
| 225 | 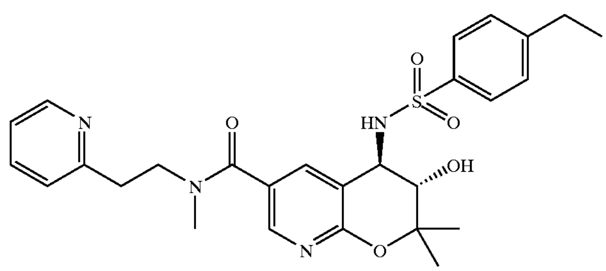 | 525 (M + 1) |
| 226 | 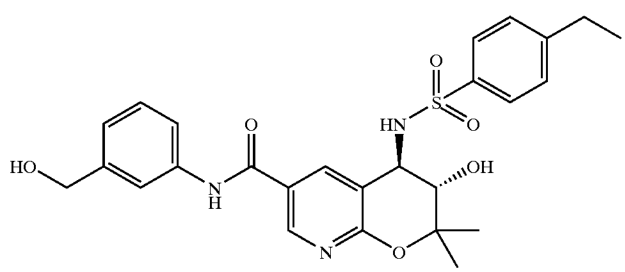 | 512 (M + 1) |
| 227 | 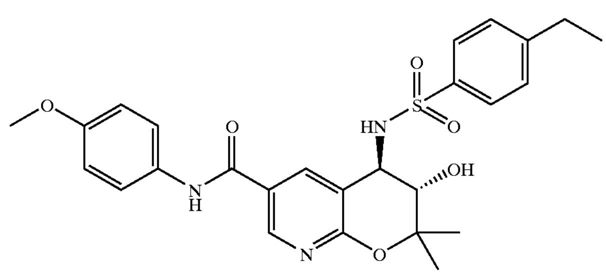 | 512 (M + 1) |

-continued

| Example | Structure | mass spec m/z |
|---|---|---|
| 228 | 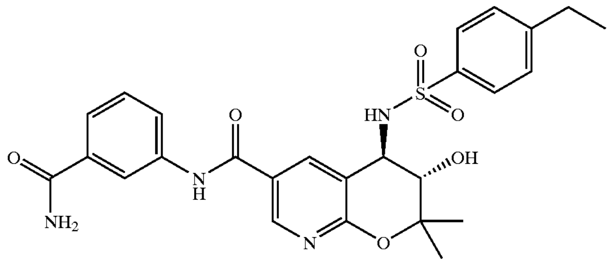 | 525 (M + 1) |
| 229 | 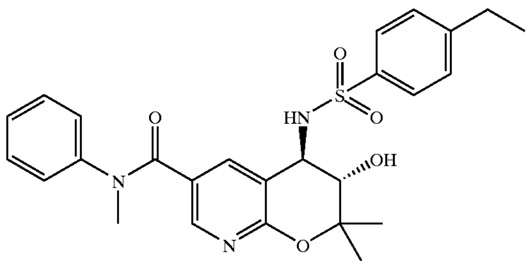 | 496 (M + 1) |
| 230 | 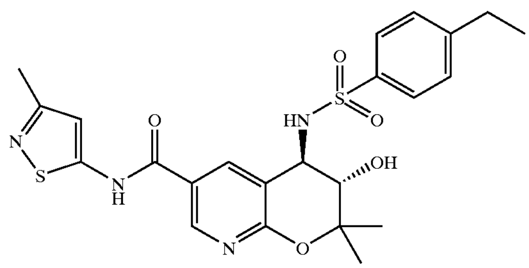 | 503 (M + 1) |
| 231 | 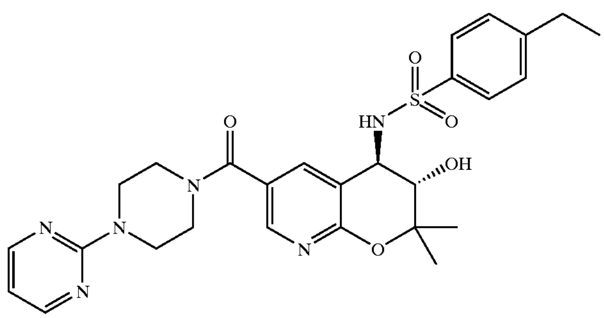 | 553 (M + 1) |
| 232 | 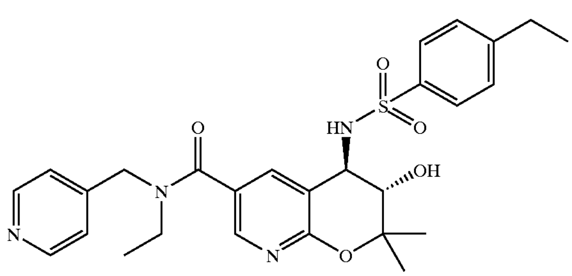 | 525 (M + 1) |

-continued

| Example | Structure | mass spec m/z |
|---|---|---|
| 233 | 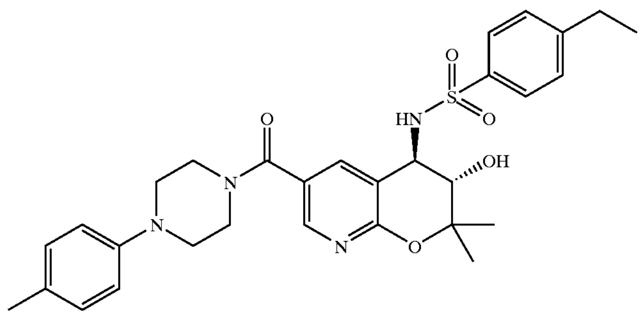 | 565 (M + 1) |
| 234 | 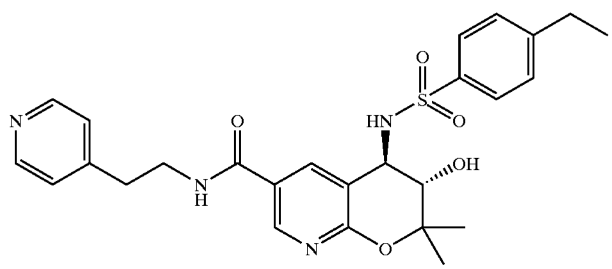 | 511 (M + 1) |
| 235 | 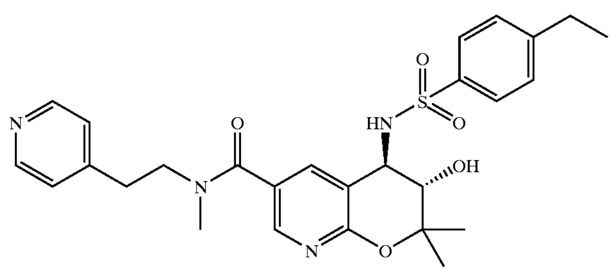 | 525 (M + 1) |
| 236 | 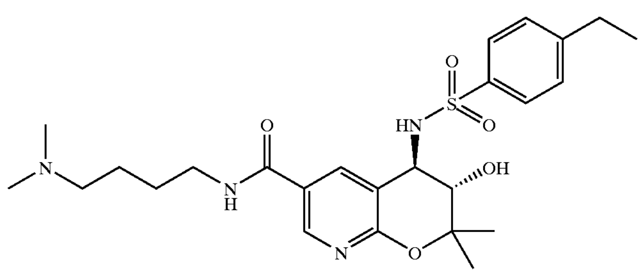 | 505 (M + 1) |
| 237 | 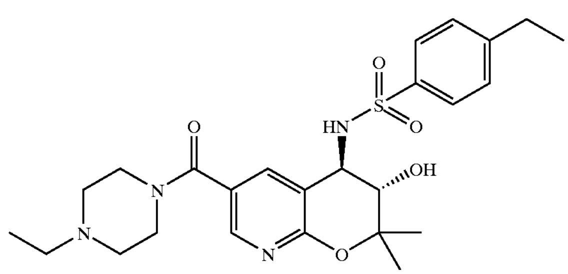 | 503 (M + 1) |

-continued

| Example | Structure | mass spec m/z |
|---|---|---|
| 238 | 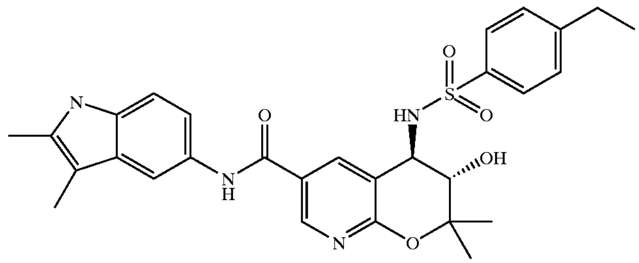 | 549 (M + 1) |
| 239 | 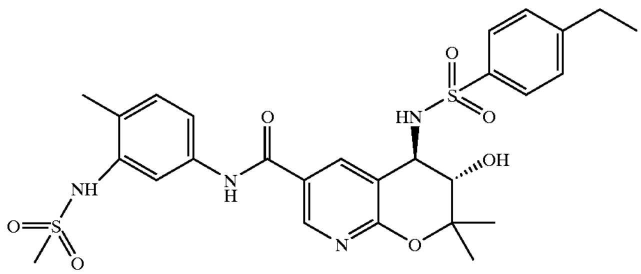 | 589 (M + 1) |
| 240 | 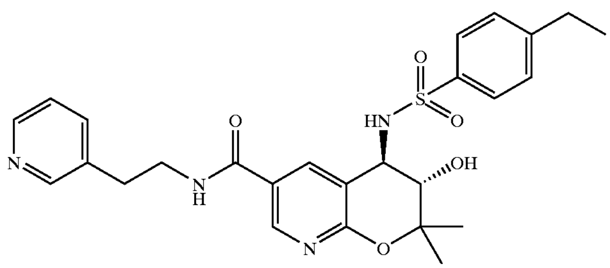 | 511 (M + 1) |
| 241 | 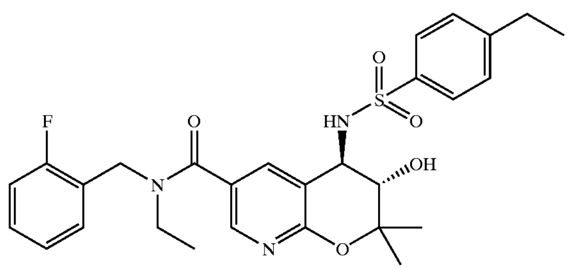 | 542 (M + 1) |
| 242 | 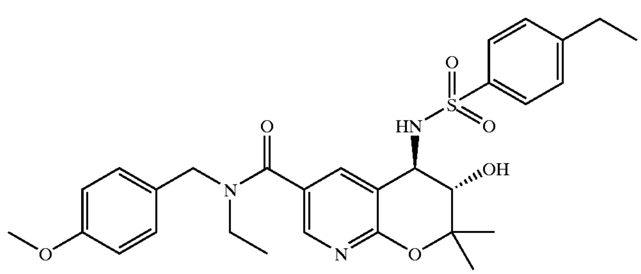 | 554 (M + 1) |

-continued
| Example | Structure | mass spec m/z |
|---|---|---|
| 243 | 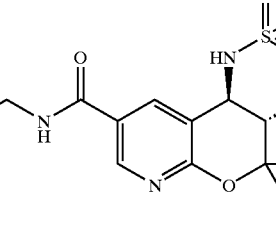 | 596 (M + 1) |
| 244 | 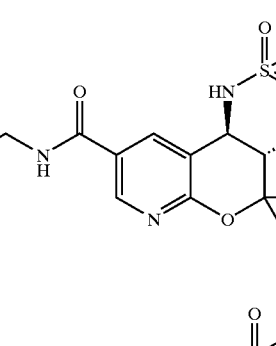 | 514 (M + 1) |
| 245 | 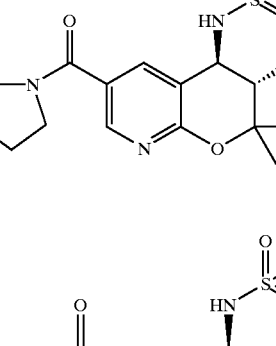 | 508 (M + 1) |
| 246 | 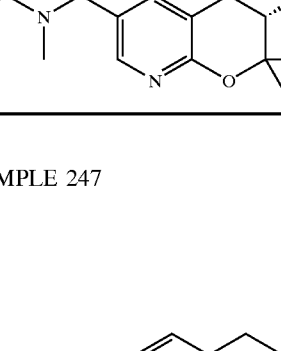 | 510 (M + 1) |
EXAMPLE 247
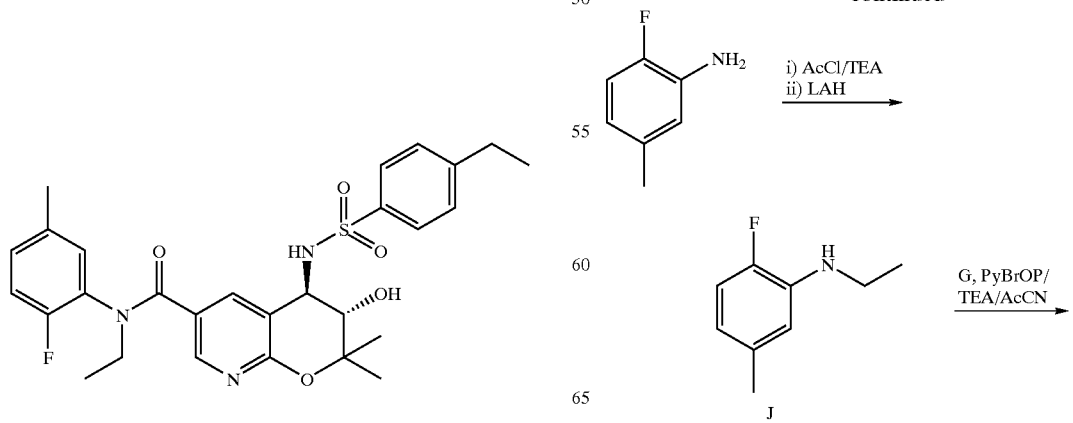

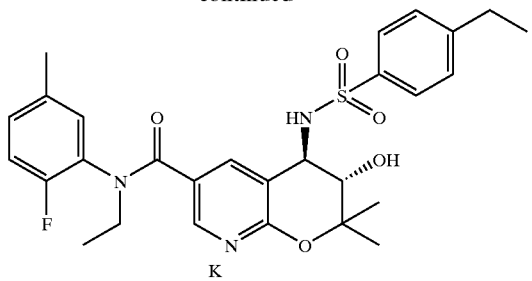

K

Preparation of J: To a stirred solution of 2-Fluoro-5-methyl aniline (187 mg, 1.50 mmol) in anhydrous dichloromethane (4 mL) containing triethylamine (150 mg, 1.48 mmol) at ambient temperature was added acetyl chloride dropwise (130 mg, 1.64 mmol, 1.10 equivalent). After 14 h the solvents were removed in vacuo yielding a white solid product (271 mg, quantative). HPLC: 96% at 2.67 min (YMC S5 ODS 4.6×50 mm Ballistic column) 10–90% MeOH/water with 0.2% $H_3PO_4$ linear gradient over 4 min, 4 mL/min, UV Detection at 220 nm. LCMS: 97% at 2.21 min (YMC S5 ODS 4.6×50 mm Ballistic column) 10–90% MeOH/water with 0.1% TFA linear gradient over 4 min, 4 mL/min, UV Detection at 220 nm, M+1 168.

The crude N-acetamide (162 mg, 0.96 mmol) was dissolved in anhydrous acetonitrile (4 mL) and a solution of Lithium Aluminum Hydride was added (1.6 mL, 1.6 mmol, 1.0 M in THF) dropwise. When evolution of hydrogen had ceased, the slurry was heated to 70° C. for 1 h, allowed to cool and then transferred to a 2.5 g C18 cartridge which had been pre-washed successively with 7.5 mL Water, 7.5 mL MeOH and 7.5 mL dichloromethane. The N-Ethylated product, J, was eluted with 7.5 mL of dichloromethane and the solvents removed to yield a pale yellow residue (50 mg, 34%). HPLC: 80% at 1.74 min (YMC S5 ODS 4.6×50 mm Ballistic column) 10–90% MeOH/water with 0.2% $H_3PO_4$ linear gradient over 4 min, 4 mL/min, UV Detection at 220 nm. LCMS: 80% at 1.62 min (YMC S5 ODS 4.6×50 mm Ballistic column) 10–90% MeOH/water with 0.1% TFA linear gradient over 4 min, 4 mL/min, UV Detection at 220 nm, M+1 154.

Preparation of K: Compound K was synthesized and purified using the procedure described for the preparation of H in Example 206. LCMS: 80% at 1.62 min (YMC S5 ODS 4.6×50 mm Ballistic column) 10–90% MeOH/water with 0.1% TFA linear gradient over 4 min, 4 mL/min, UV Detection at 220 nm, M+1 154.

The following compounds were synthesized by the procedures described in Example 247

| Example | Structure | Mass spec M/Z |
| --- | --- | --- |
| 248 | 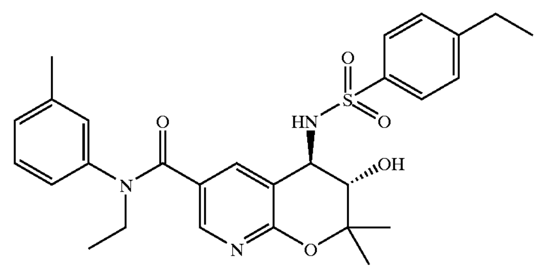 | 524 (M + 1) |
| 249 | 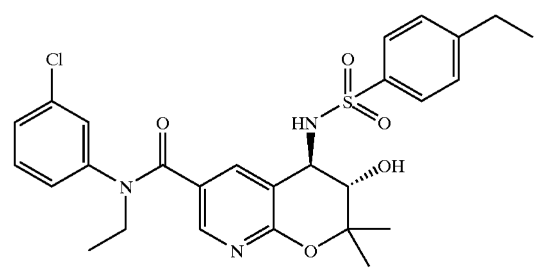 | 544 (M + 1) |
| 250 | 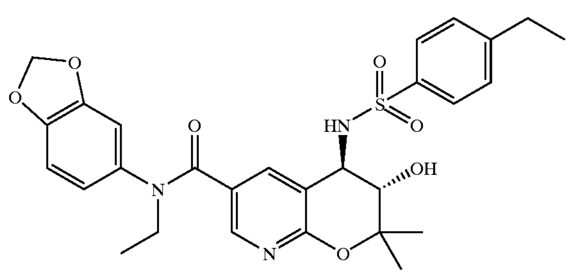 | 554 (M + 1) |

-continued

| Example | Structure | Mass spec M/Z |
|---|---|---|
| 251 | 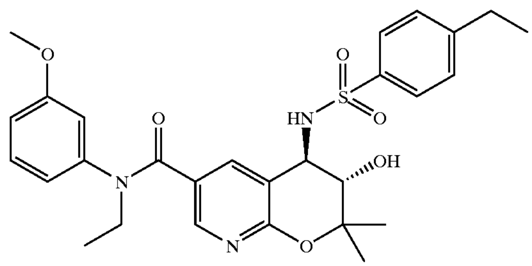 | 540 (M + 1) |
| 252 | 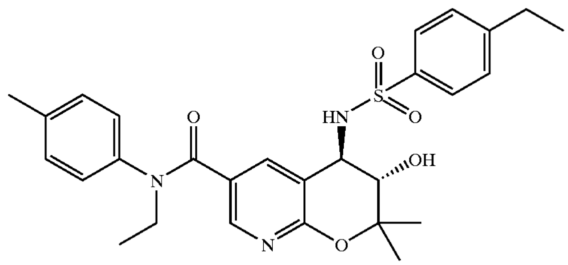 | 524 (M + 1) |
| 253 | 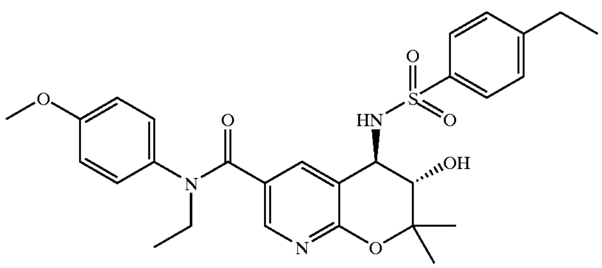 | 540 (M + 1) |
| 254 | 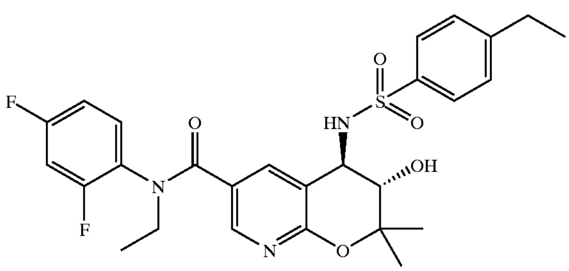 | 546 (M + 1) |
| 255 | 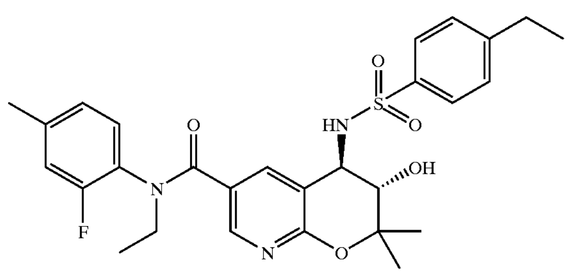 | 542 (M + 1) |

-continued

| Example | Structure | Mass spec M/Z |
|---|---|---|
| 256 | 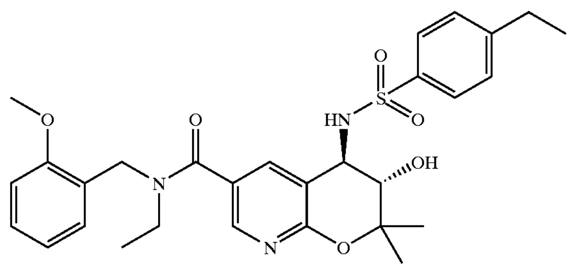 | 554 (M + 1) |
| 257 | 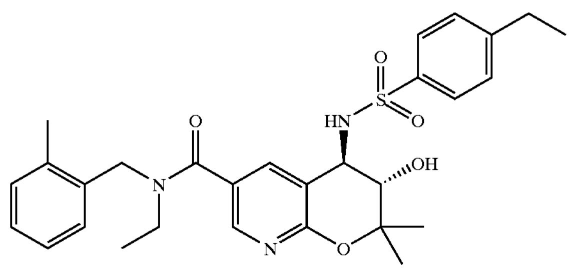 | 538 (M + 1) |
| 258 | 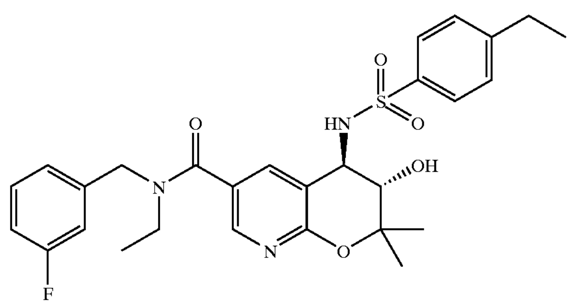 | 542 (M + 1) |
| 259 | 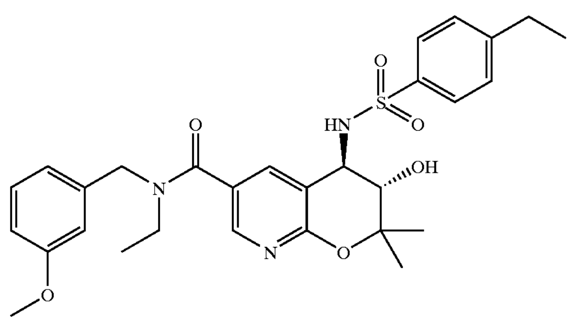 | 554 (M + 1) |
| 260 | 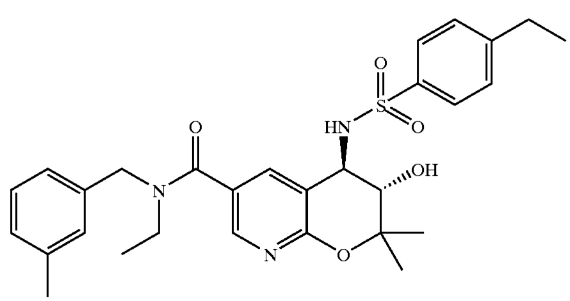 | 538 (M + 1) |

-continued
| Example | Structure | Mass spec M/Z |
|---|---|---|
| 261 | 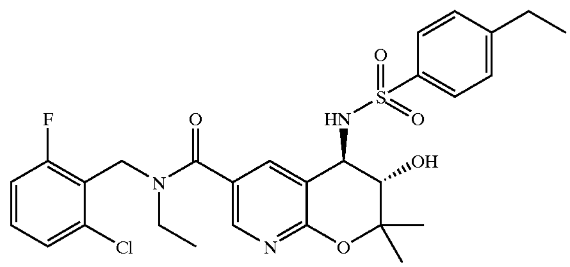 | 576 (M + 1) |
| 262 | 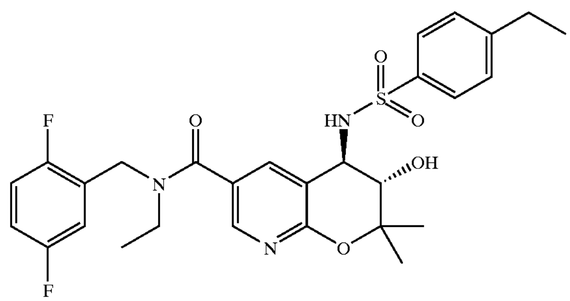 | 560 (M + 1) |
| 263 | 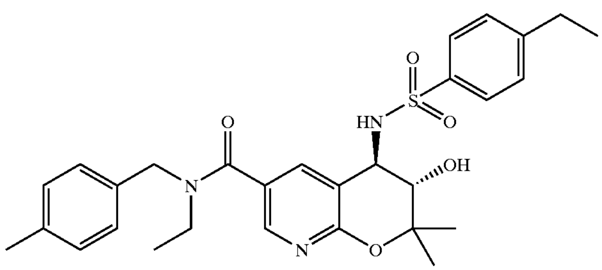 | 538 (M + 1) |
| 264 | 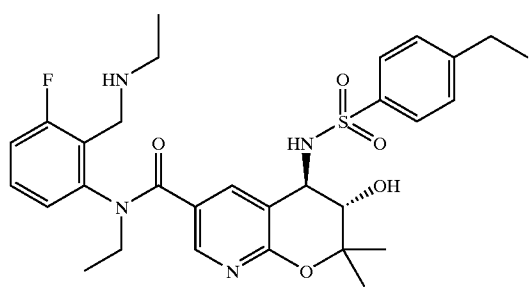 | 585 (M + 1) |
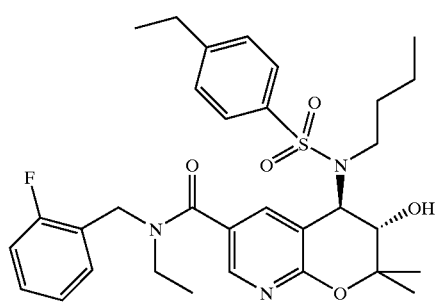

-continued
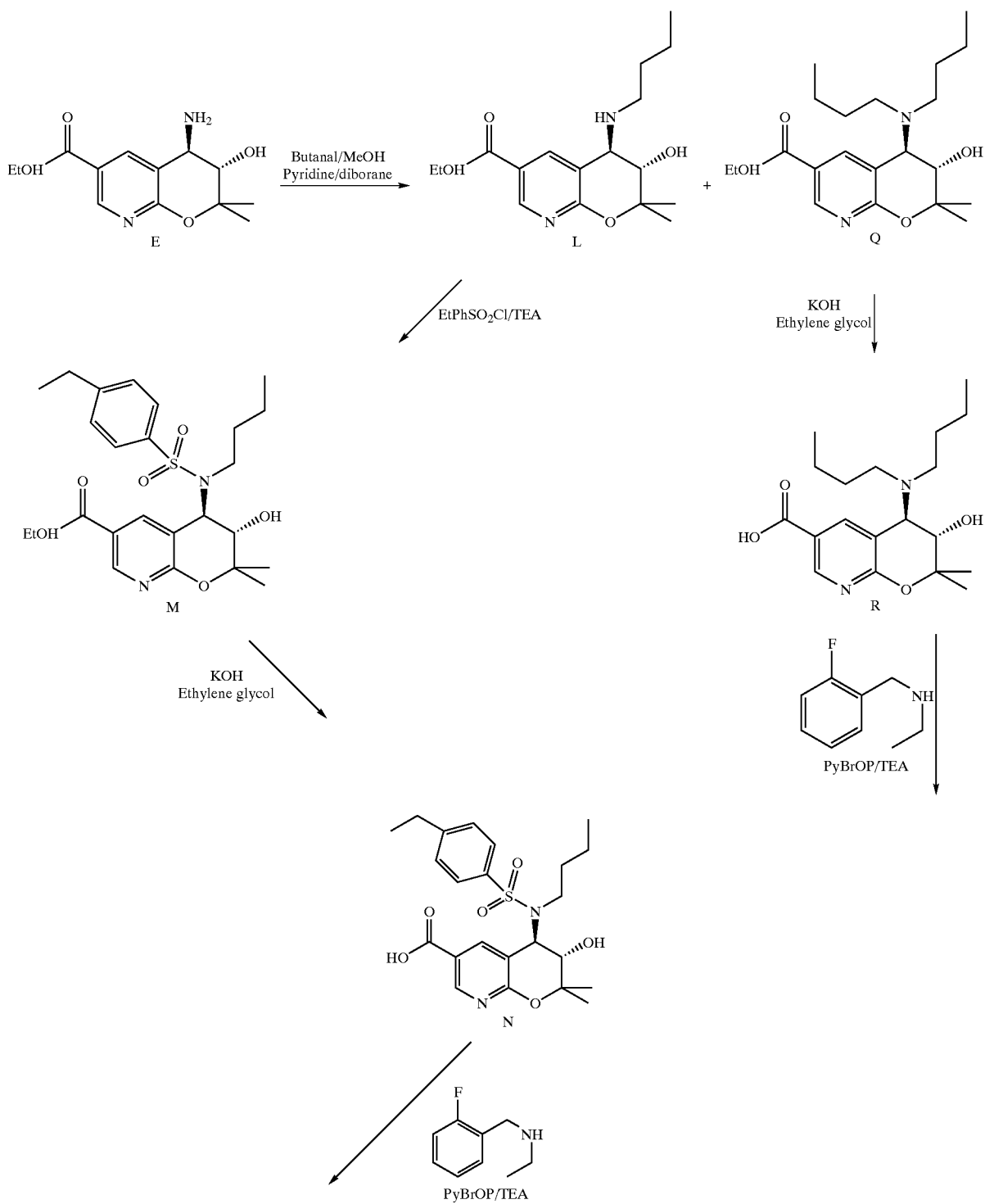

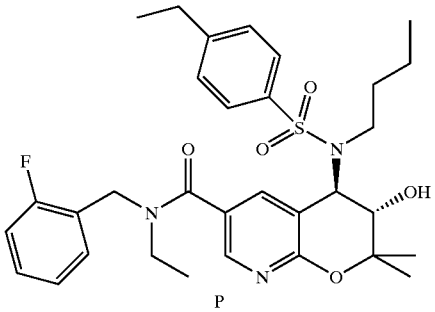

P

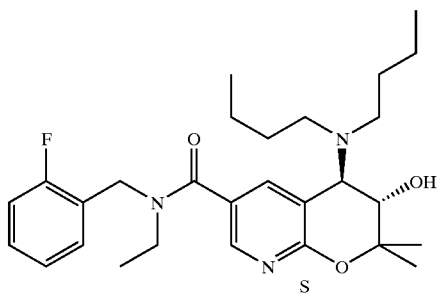

S

Preparation of L and Q: At 20° C., Pyridine diborane complex (0.032 mL, 0.317 mmol) was added dropwise with stirring to a slurry of amino-alcohol, B (100 mg, 0.38 mmol) and butanal (28 mg, 0.39 mmol) in anhydrous methanol (1.0 mL) containing powdered 4A molecular sieves (34 mg). After 14 h, 5% HCl was added (10 mL) and the resulting solution stirred for 10 min then adjusted to pH11 by addition of 5% NaOH and extracted into dichloromethane (3×20 mL). The combined extracts were dried over $Na_2SO_4$, decanted, concentrated, redissolved in 1 mL of acetone and applied directly to a preparative silica gel TLC plate, (20×20 cm, 1mm thickness, 254 nm UV indicator) eluting with 2:1 hexane:acetone. L was isolated as the more polar product ($R_f$ 0.3, 63 mg, 52%) LCMS: RT 2.53 min (YMC S5 ODS 4.6×50 mm Ballistic column) 10–90% MeOH/water with 0.1% TFA linear gradient over 4 min, 4 mL/min, UV Detection at 220 nm, M+1 323. Q was isolated a the less polar product ($R_f$ 0.4, 41 mg, 29%) LCMS: $R_T$ 2.88 min (YMC S5 ODS 4.6×50 mm Ballistic column) 10–90% MeOH/water with 0.1% TFA linear gradient over 4 min, 4 mL/min, UV Detection at 220 nm, M+1 379.

Preparation of M: To a solution of Ethyl-6-carboxy-trans-N-[n-butyl]-4-amino-3-hydroxy-2,2-dimethyl-$^2$H-pyrano-[2,3b]-pyridine (L, 63 mg, 0.20 mmol) in $CH_2Cl_2$/TEA (4 mL/5 drops) was -added $EtPhSO_2Cl$ (44 mg, 0.22 mmol) at ambient temperature. The resulting solution was stirred for 4 days, diluted with a further 40 mL of $CH_2Cl_2$ and passed through a short pad of silica (approx. 3 cm). The resulting pale yellow solid (96 mg, crude quantative) was sufficiently pure to be hydrolyzed directly. LCMS: $R_T$ 4.04 min (YMC S5 ODS 4.6×50 mm Ballistic column) 10–90% MeOH/water with 0.1% TFA linear gradient over 4 min, 4 mL/min, UV Detectron at 220 nm, M+1 491.

Preparation of N: A solution of Ethyl-6-carboxy-trans-N,N-[n-butyl-4-ethylphenylsulfonyl]-4-amino-3-hydroxy-2,2-dimethyl-2H-pyrano-[2,3b]-pyridine (M, 96 mg, 0.20 mmol) in ethylene glycol/THF (2.5/1.5 mL) and aqueous KOH (2.5 mL, 30% by weight) was heated to 110° C. for 3 h. The cooled solution was diluted with water (ca. 200 mL), the pH adjusted to 4–5 with 5% HCl and extracted successively with $CH_2Cl_2$ (3×50 mL) and EtOAc (2×50 mL). The combined organic portions were dried over $Na_2SO_4$, decanted and the solvents removed. N was obtained as a pale yellow oil (59 mg, 64%) sufficiently pure to be used without further purification. HPLC: >81% at 4.15 min (YMC S5 ODS 4.6×50 mm Ballistic column) 10–90% MeOH/water with 0.2% $H_3PO_4$ linear gradient over 4 min, 4 mL/min, UV Detection at 220 nm. LCMS: $R_T$ 3.77 min (YMC S5 ODS 4.6×50 mm Ballistic column) 10–90% MeOH/water with 0.1% TFA linear gradient over 4 min, 4 mL/min, UV Detection at 220 nm, M+1 463.

Preparation of P: P was prepared in 35% isolated yield by the coupling described previously for the preparation of H in Example N. The crude reaction mixture was purified by preparative HPLC (YMC PACK S5 ODSA 20×100 mm column Reversed phase C18). 23–90% MeOH/water with 0.1% TFA linear gradient over 10 min 5 min hold time, 20 mL/min, UV Detection at 220 nm yielding the TFA salt of P as a white amorphous solid (13.3 mg, 35%). HPLC: 100% at 4.59 min (YMC S5 ODS 4.6×50 mm Ballistic column) 10–90% MeOH/water with 0.2% $H_3PO_4$ linear gradient over 4 min, 4 mL/min, UV Detection at 220 nm. LCMS: 99.1% at 4.24 min (YMC S5 ODS 4.6×50 mm Ballistic column) 10–90% MeOH/water with 0.1% TFA linear gradient over 4 min, 4 mL/min, UV Detection at 220 nm, M+1 598. $^1$HNMR: $CDCl_3$ 0.88,m(4H); 1.20–1.24,m(9H); 1.26,s(3H); 1.46,s(3H); 2.73,d,J=7.6 Hz (2H); 4.03,brs(7H); 5.05,s(1H); 7.0,t,J=8.0 Hz (1H); 7.15,t,J=8.0 Hz (1H); 7.2–7.4,m(2H); 7.34,d,J=8.0 Hz (2H); 7.67,brd(2H); 7.9,brs(1H); 8.27,s (1H).

Preparation of R: R was prepared via KOH hydrolysis of ester Q in 68% yield as described for the preparation of N in Example N". LCMS: 82% at 2.31 min (YMC S5 ODS 4.6×50 mm Ballistic column) 10–90% MeOH/water with 0.1% TFA linear gradient over 4 min, 4 mL/min, UV Detection at 220 nm, M+1 351.

Preparation of S: S was prepared in 58% isolated yield by the coupling described previously for the preparation of H in Example N. The crude reaction mixture was purified by preparative HPLC (YMC PACK S5 ODSA 20×100 mm column Reversed phase C18) 23–90% MeOH/water with 0.1% TFA linear gradient over 10 min 5 min hold time, 20 mL/min, UV Detection at 220 nm yielding the TFA salt of S as a white amorphous solid (20.0 mg, 58%). HPLC: 96% at 3.49 min (YMC S5 ODS 4.6×50 mm Ballistic column) 10–90% MeOH/water with 0.2% $H_3PO_4$ linear gradient over 4 min, 4 mL/min, UV Detection at 220 nm. LCMS: 3.24 min (YMC S5 ODS 4.6×50 mm Ballistic column) 10–90% MeOH/water with 0.1% TFA linear gradient over 4 min, 4 mL/min, UV Detection at 220 nm, M+1 486. $^1$HNMR: MeOD 0.92,brm(10H); 1.17;t,J=7 Hz (3H);.1.25,s(3H); 1.3,brs(4H),; 1.58,s(3H); 1.8–2.0 brm(2H); 3.0–3.2,brm(2H); 3.6,m(3H); 4.23,d,J=8.8 Hz (1H); 4.9,s(2H); 7.05–7.40, m(4H); 8.20,d,J=1.6 Hz (1H); 8.30,brs(1H).

The following compounds were synthesized by the procedures described in Example 265

| Example | Structure | Mass spec M/Z |
|---|---|---|
| 266 | 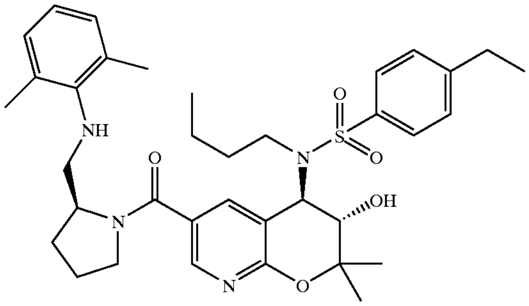 | 648 (M + 1) |
| 267 | 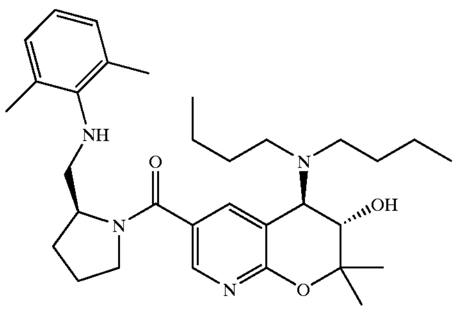 | 537 (M + 1) |
EXAMPLE 268
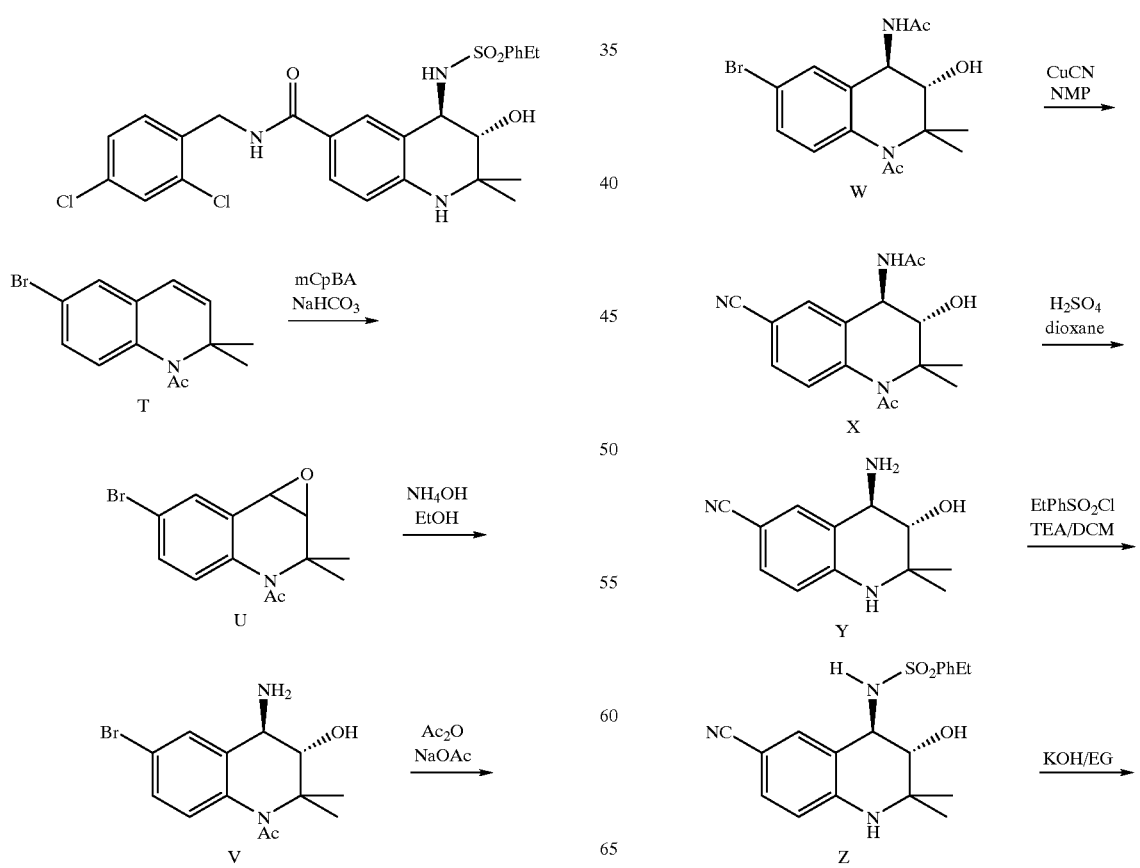

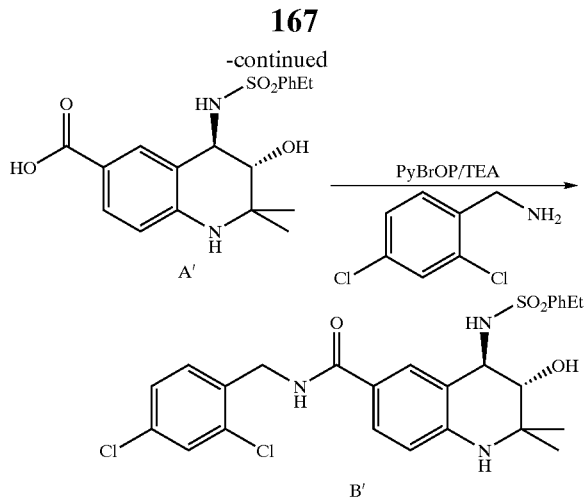

Preparation of T: N-Acetyl-6-bromo-2,2-dimethyl-1,2-dihydroquinoline was prepared from commercially available pBromoaniline in 3 steps as described. [3,4]

Preparation of U: At 0° C., mCpBA (4.08 g, assuming 50% active, 1.5 equivalents) was added in 3 portions, 3 minutes apart to a vigorously stirred biphase solution of N-Acetyl-6-bromo-2, 2-dimethyl-1,2-dihydroquinoline (2.21 g, 7.92 mmol) in dichloromethane/saturated NaHCO$_3$ 140 mL/200 mL. Stirring was maintained for 12 h as the slurry reached ambient temperature. The reaction mixture was diluted with CH$_2$Cl$_2$ (50 mL) and the aqueous portion washed further with CH$_2$Cl$_2$ (3×50 mL). The combined organic portions were washed with saturated NaCl, (30 mL) dried over Na$_2$SO$_4$, decanted and the solvents removed. U was obtained as a pale yellow oil (2.52 g, crude quantitative) sufficiently pure to be used without further purification. $^1$HNMR: CDCl$_3$ 1.18,s(3H); 1.90,s(3H); 2.10,s(3H); 3.40, d,J=4.3 Hz (1H); 3.80,d,J=4.2 Hz (1H); 6.72,d,J=8.5 Hz (1H); 7.40,dd,J=2.4 Hz and J=8.6 Hz (1H); 7.52,d,J=2.2 Hz.

Preparation of V: A solution of epoxide U (442 mg, 1.44 mmol) in ethanol/concentrated NH$_4$OH (4 mL/4 mL) was heated to reflux (75° C.). A second portion of concentrated NH$_4$OH (4 mL) was added and the resulting brown solution heated to reflux for a further 24 h. The solvents were removed under reduced pressure, the residue dissolved in methanol and purified by flash silica gel column chromatography (CH$_2$Cl$_2$ primed and eluted with 10% methanol in CH$_2$Cl$_2$). N-Acetyl-6-bromo-4-amino-3-hydroxy-2,2-dimethyl-1,2,3,4-tetra hydroquinoline, V (238 mg, 53%) was obtained as a tan powder. HPLC: 83% at 3.00 min (YMC S5 ODS 4.6×50 mm Ballistic column) 10–90% MeOH/water with 0.2% H$_3$PO$_4$ linear gradient over 4 min, 4 mL/min, UV Detection at 220 nm. $^1$HNMR: CDCl$_3$ 1.16,s(3H); 1.29,s(3H); 2.15,s(3H); 3.56,d,J=9.6 Hz (1H); 5.01,t,J=8.7 Hz (1H); 5.86,d,J=7.2 Hz (1H); 6.39,d,J=8.5 Hz (1H); 7.14,dd,J=2.0 Hz and J=8.2 Hz (1H); 7.22,d,J=1.8 Hz.

Preparation of W: Anhydrous NaOAc (162 mg, 1.98 mmol) was added to a stirred solution of amino alcohol V (168 mg, 0.538 mmol) in Acetic Anhydride (2 mL) at ambient temperature. The pale brown solution was heated to 90° C. for 3 h, allowed to cool and poured into water (50 mL). The aqueous phase was extracted with EtOAc (30 mL, 2×20 mL) and the combined organic portions washed successively with saturated NaHCO$_3$ (2×20 mL) and water (20 mL) dried over Na$_2$SO$_4$, decanted and concentrated. The brown oil was azeotroped with ether to yield a crude quantative amount of W as a tan solid. HPLC: >80% at 3.43 min (YMC S5 ODS 4.6×50 mm Ballistic column) 10–90% MeOH/water with 0.2% H$_3$PO$_4$ linear gradient over 4 min, 4 mL/min, UV Detection at 220 nm.

Preparation of X: In a thick walled glass reaction vessel with a teflon screw cap, a solution of N-Acetyl-6-bromo-4-acetamido-3-hydroxy-2,2-dimethyl-1,2,3,4-tetra hydroquinoline, W (190 mg, 0.538 mmol) in N-Methylpyrrolidinone (2 mL) was added to CuCN (96 mg, 1.1 mmol). The vigorously stirred slurry was heated to 190–200° C. for 4 h, allowed to cool then poured into NH$_4$OH (50 mL). After 2 h the aqueous phase was extracted with EtOAc (3×20 mL) and the combined portions washed further with NH$_4$OH (3×20 mL) and water (2×20 mL). The solution was dried over Na$_2$SO$_4$, decanted and concentrated yielding a brown oil which was flash column chromatographed directly over silica, hexane primed, hexane/EtOAc/MeOH (2:1:1) as eluent. X was obtained as a pale brown oil (94 mg, 58%). HPLC: 2.56 min (YMC S5 ODS 4.6×50 mm Ballistic column) 10–90% MeOH/water with 0.2% H$_3$PO$_4$ linear gradient over 4 min, 4 mL/min, UV Detection at 220 nm. $^1$HNMR: CDCl$_3$ 1.23,s(3H); 1.27,s(3H); 2.08,s(3H); 2.13,s(3H); 4.93;d,J=10 Hz (1H);,5.30,t,J=10 Hz (1H); 5.86, d,J=9.5 Hz (1H); 6.48,d,J=8.4 Hz (1H); 7.27,brd,J=8.0 Hz (1H); 7.27,brs.

Preparation of Y: Concentrated H$_2$SO$_4$ (0.54 mL) was added to a solution of N-Acetyl-6-cyano-4-acetamido-3-hydroxy-2,2-dimethyl-1,2,3,4-tetrahydroquinoline, (3.45 g, 11.5 mmol) in dioxane/water (35 mL/20 mL) and the solution heated to reflux at 110° C. for 16 h. The cooled solution was poured into NH$_4$OH (30 mL) and extracted with EtCAc (3×20 mL). The combined portions were dried over Na$_2$SO$_4$, decanted and concentrated yielding a tan solid, Y (1.99 g, 80%). HPLC: 2.00 min (YMC S5 ODS 4.6×50 mm Ballistic column) 10–90% MeOH/water with 0.2% H$_3$PO$_4$ linear gradient over 4 min, 4 mL/min, UV Detection at 220 nm.

Preparation of A': A' was prepared in 93% yield by KOH hydrolysis described previously for the preparation of G in Example N. HPLC: 97% at 3.47 min (YMC S5 ODS 4.6×50 mm Ballistic column) 10–90% MeOH/water with 0.2% H$_3$PO$_4$ linear gradient over 4 min, 4 mL/min, UV Detection at 220 nm. LCMS: 3.14 min (YMC S5 ODS 4.6×50 mm Ballistic column) 10–90% MeOH/water with 0.1% TFA linear gradient over 4 min, 4 mL/min, UV Detection at 220 nm, M+1 405. $^1$HNMR: DMSO 1.13,s(3H); 1.16,t,J=7.2 Hz (2H); 1.21,s(3H); 2.68, q, J=7.6 Hz (3H); 4.17, t, J=8.6 Hz (1H); 4.87, d, J=5.4 Hz (1H); 6.46, d , J=9.8 Hz (1H); 6.53, brs (1H); 7.36, d, J=8.2 Hz (2H); 7.49, dd, J=1.6 Hz and J=8.4 Hz (1H); 7.79, d, J=8.4 Hz (2H); 7.80, d, J=1.6 Hz (1H); 7.86, d, J=8.4 Hz (1H).

Preparation of B': B' was prepared in 30% isolated yield by the coupling described previously for the preparation of H in Example N. The crude reaction mixture was purified by preparative HPLC (YMC PACK S5 ODSA 20×100 mm column Reversed phase C18) 23–90% MeOH/water with 0.1% TFA linear gradient over 10 min 5 min hold time, 20 mL/min, UV Detection at 220 nm yielding B' as a white amorphous solid (28 7 mg, 30%). HPLC: 97% at 4.02 min (YMC S5 ODS 4.6×50 mm Ballistic column) 10–90% MeOH/water with 0.2% H$_3$PO$_4$ linear gradient over 4 min, 4 mL/min, UV Detection at 220 nm. LCMS: 4.02 min (YMC S5 ODS 4.6×50 mm Ballistic column) 10–90% MeOH/water with 0.1% TFA linear gradient over 4 min, 4 mL/min, UV Detection at 220 nm, M+1 562. ¹HNMR: MeOD 1.11, s(3H); 1.25, t, J=7.4 Hz (3H); 1.25, s(3H); 2.71, q, J=7.2 Hz (2H); 3.50, d, J=8.5 Hz (1H); 4.28, d, J=8.5 Hz (1H); 4.58, s(2H); 6.54, d, J=8.4 Hz (1H); 7.33, s(2H); 7.38, d, J=8.4 Hz (2H); 7.5–7.6, m(3H); 7.89, s(1H); 7.89, d, J=8.4 Hz.

REFERENCE

3. Atwal, Karnail. (Squibb, E. R., and Sons, Inc., USA). Application: US 91–776921 911015
4. Williamson, N. M; March, D. R; Ward, D. A; Tetrahedron Lett. 1995, 3 36(42) 7721–4.

The following compounds were synthesized by the procedures described in Example 268

| Example | Structure | Mass spec M/Z |
| --- | --- | --- |
| 269 | 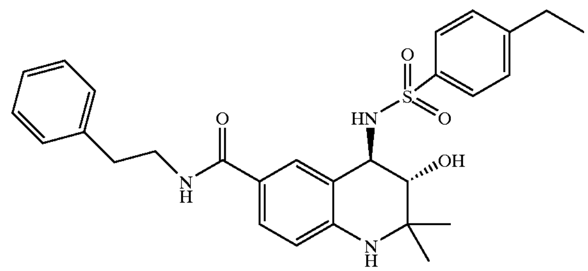 | 648 (M + 1) |
| 270 | 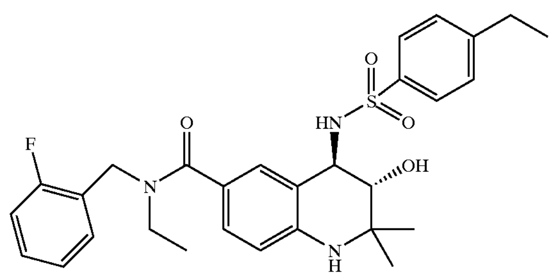 | 540 (M + 1) |
| 271 | 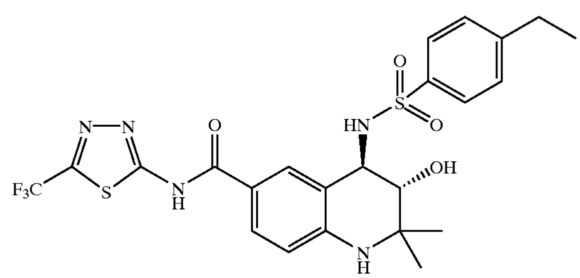 | 556 (M + 1) |
| 272 | 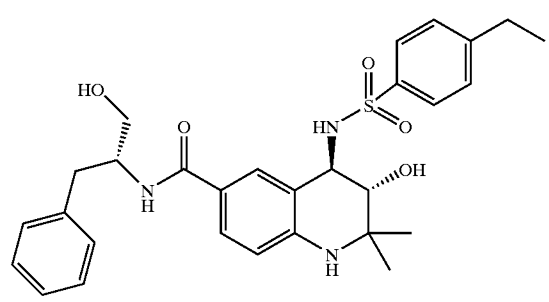 | 538 (M + 1) |

-continued

| Example | Structure | Mass spec M/Z |
|---------|-----------|---------------|
| 273 | 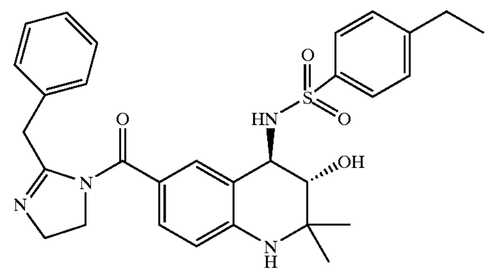 | 547 (M + 1) |
| 274 | 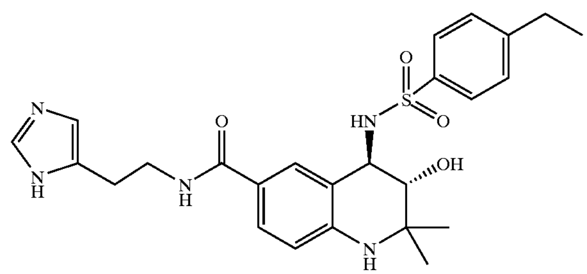 | 498 (M + 1) |
| 275 | 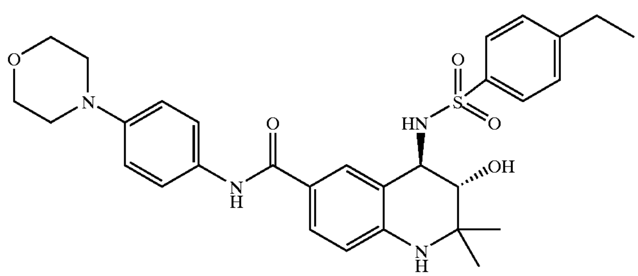 | 565 (M + 1) |
| 276 | 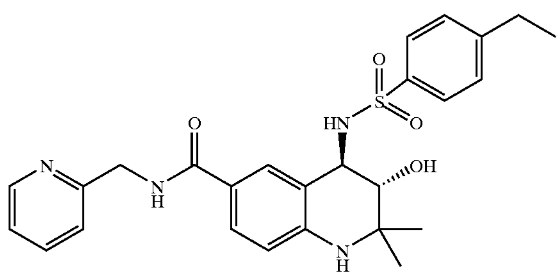 | 495 (M + 1) |
| 277 | 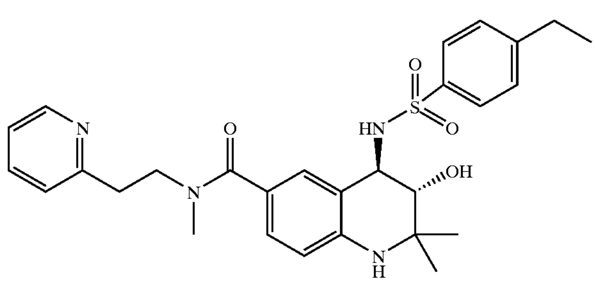 | 523 (M + 1) |

-continued

| Example | Structure | Mass spec M/Z |
|---|---|---|
| 278 | 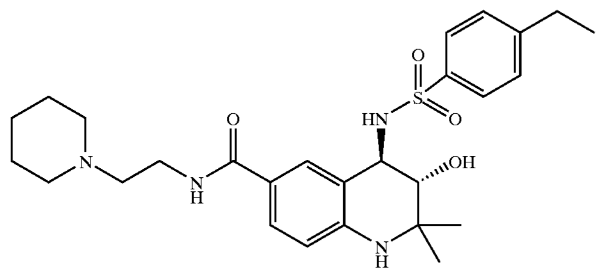 | 515 (M + 1) |
| 279 | 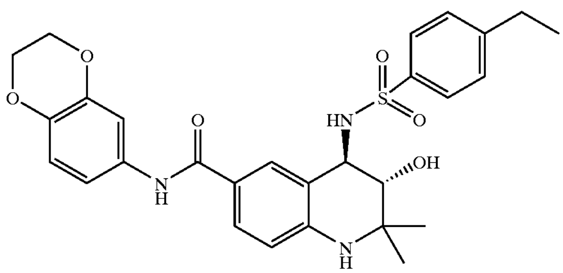 | 538 (M + 1) |
| 280 | 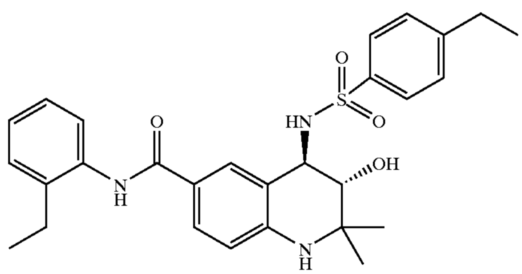 | 508 (M + 1) |
| 281 | 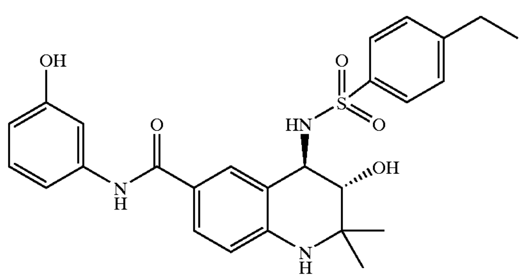 | 496 (M + 1) |
| 282 | 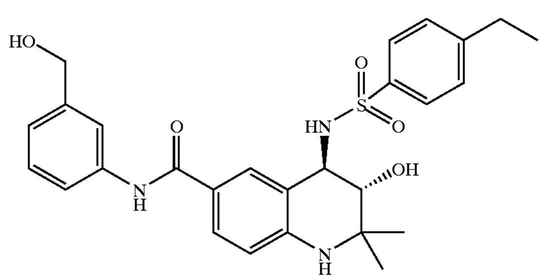 | 510 (M + 1) |

-continued

| Example | Structure | Mass spec M/Z |
|---|---|---|
| 283 | 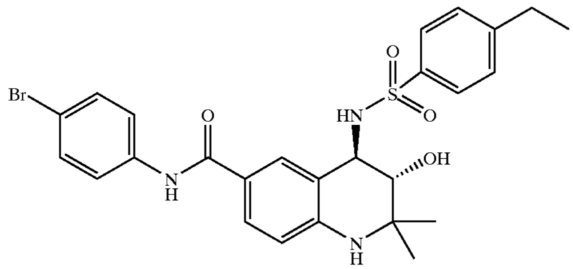 | 560 (M + 1) |
| 284 | 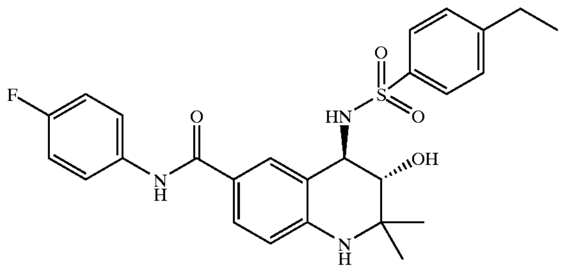 | 498 (M + 1) |
| 285 | 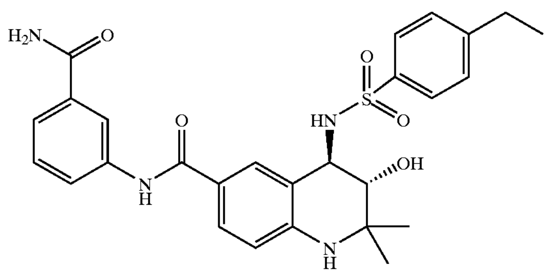 | 523 (M + 1) |
| 286 | 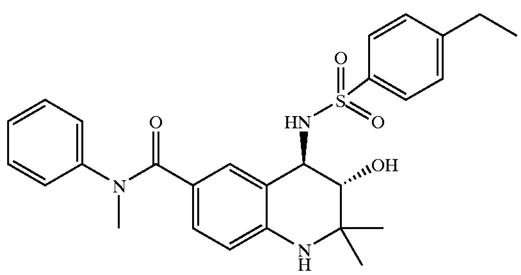 | 494 (M + 1) |
| 287 | 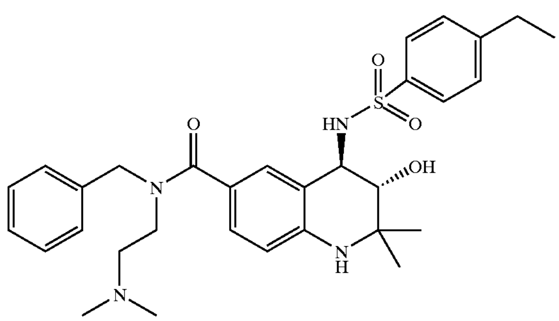 | 565 (M + 1) |

-continued

| Example | Structure | Mass spec M/Z |
|---|---|---|
| 288 | 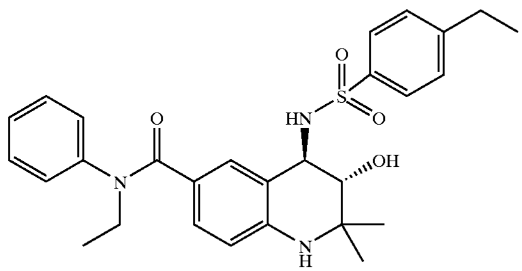 | 508 (M + 1) |
| 289 | 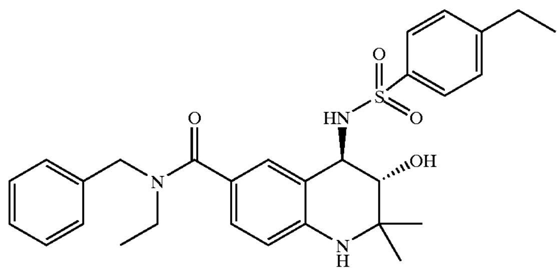 | 522 (M + 1) |
| 290 | 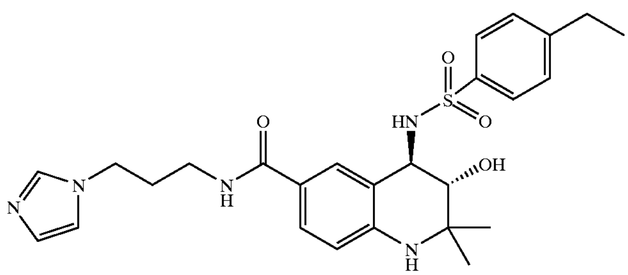 | 512 (M + 1) |
| 291 | 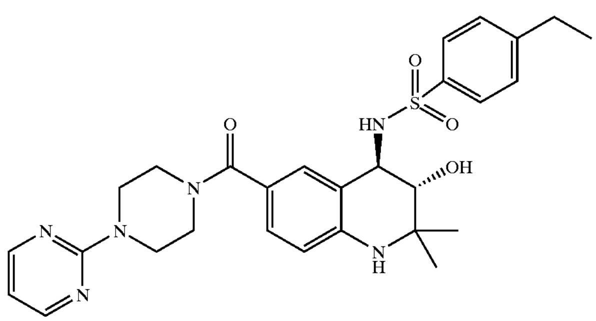 | 551 (M + 1) |
| 292 | 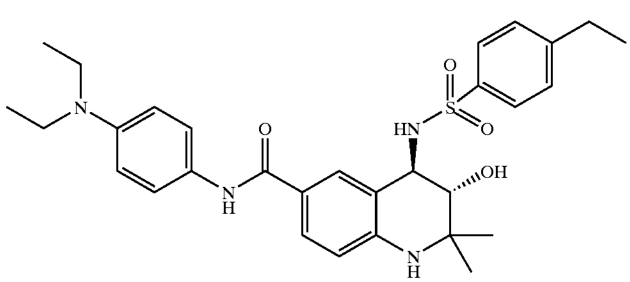 | 551 (M + 1) |

| Example | Structure | Mass spec M/Z |
|---|---|---|
| 293 | 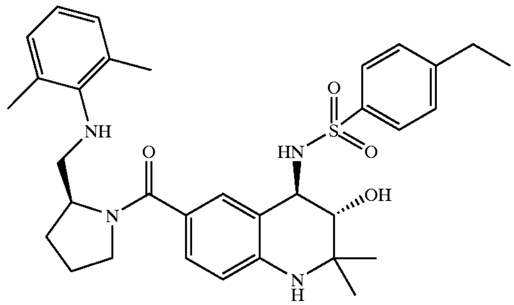 | 591 (M + 1) |
| 294 | 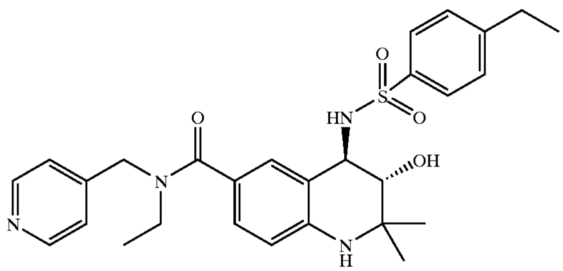 | 523 (M + 1) |
| 295 | 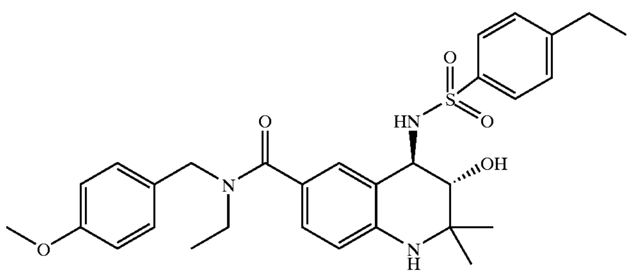 | 552 (M + 1) |
| 296 | 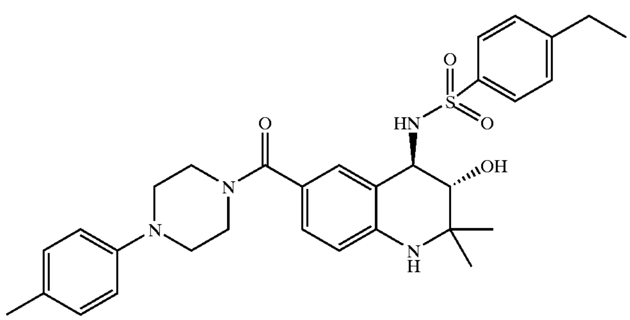 | 563 (M + 1) |
| 297 | 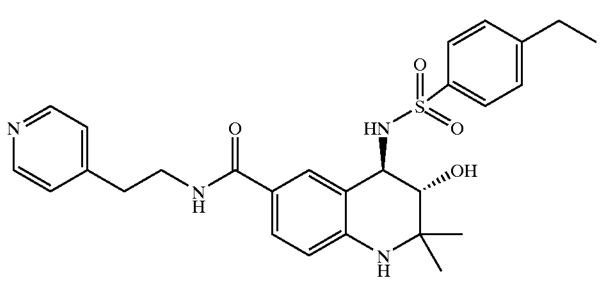 | 509 (M + 1) |

-continued

| Example | Structure | Mass spec M/Z |
|---|---|---|
| 298 | 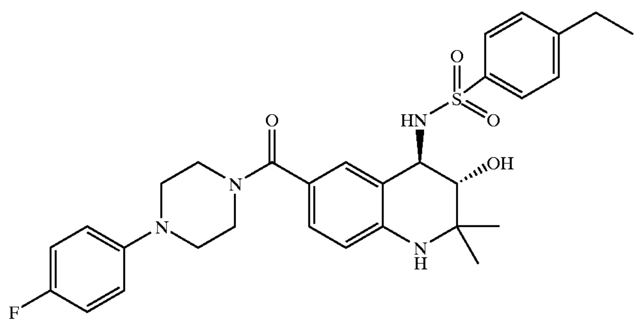 | 567 (M + 1) |
| 299 | 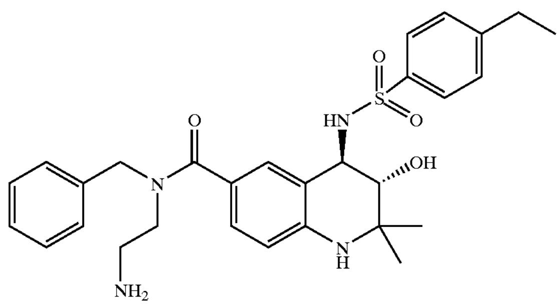 | 537 (M + 1) |
| 300 | 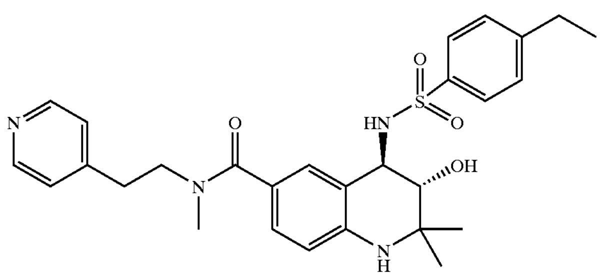 | 523 (M + 1) |
| 301 | 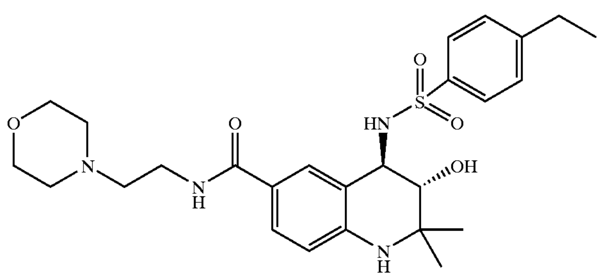 | 517 (M + 1) |
| 302 | 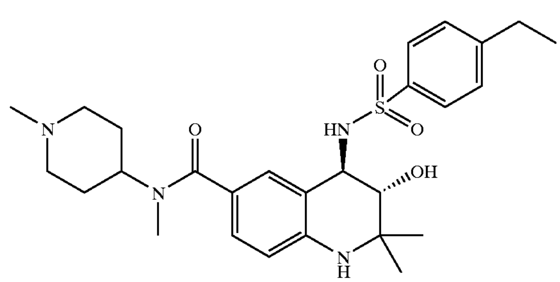 | 515 (M + 1) |

-continued

| Example | Structure | Mass spec M/Z |
|---|---|---|
| 303 | 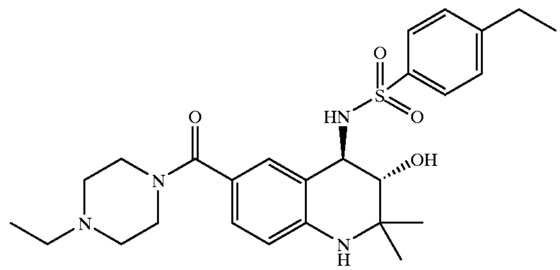 | 501 (M + 1) |
| 304 | 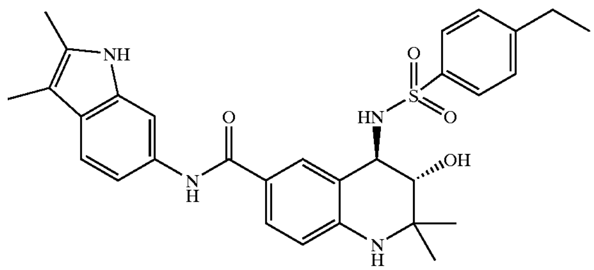 | 547 (M + 1) |
| 305 | 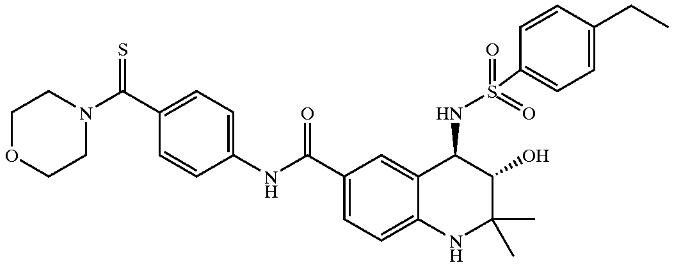 | 609 (M + 1) |
| 306 | 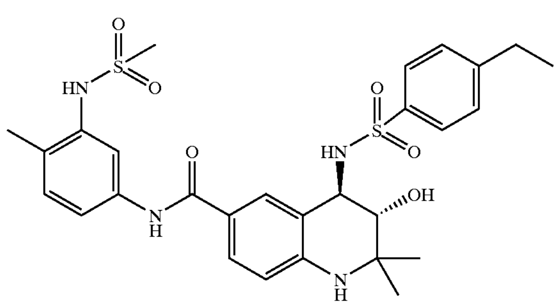 | 587 (M + 1) |
| 307 | 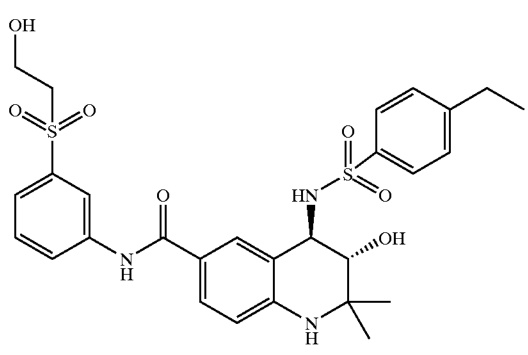 | 588 (M + 1) |

-continued

| Example | Structure | Mass spec M/Z |
|---|---|---|
| 308 | 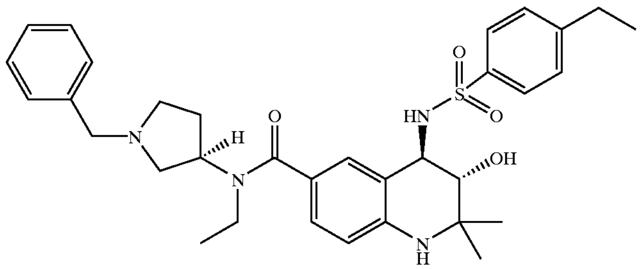 | 590 (M + 1) |
| 309 | 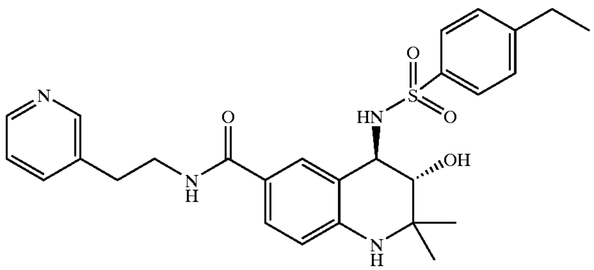 | 509 (M + 1) |
| 310 | 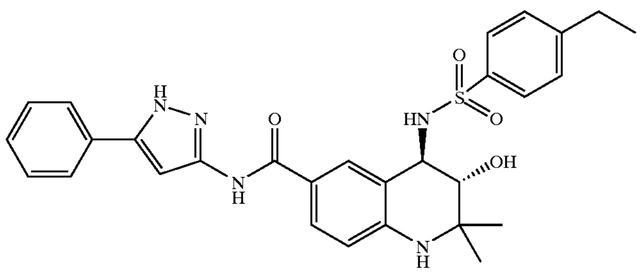 | 546 (M + 1) |
| 311 | 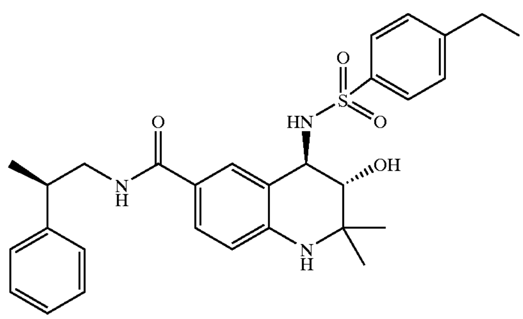 | 522 (M + 1) |
| 312 | 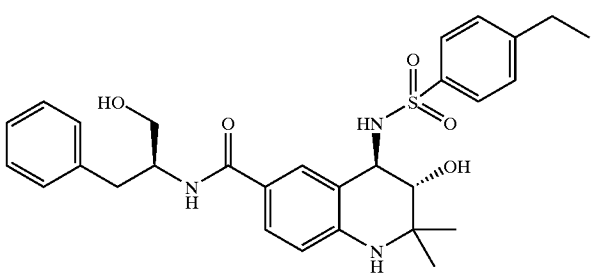 | 538 (M + 1) |

-continued

| Example | Structure | Mass spec M/Z |
|---|---|---|
| 313 | 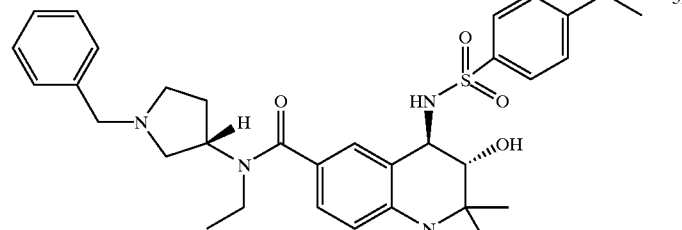 | 591 (M + 1) |
| 314 | 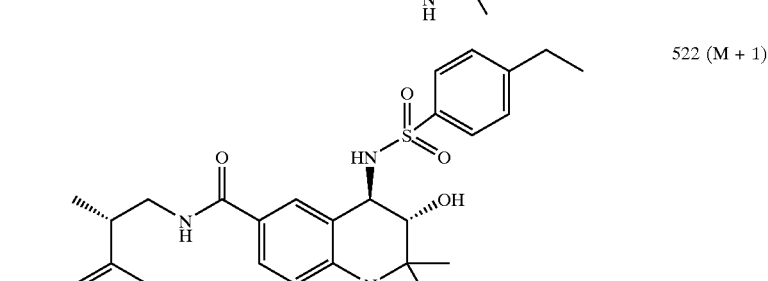 | 522 (M + 1) |

EXAMPLE 315

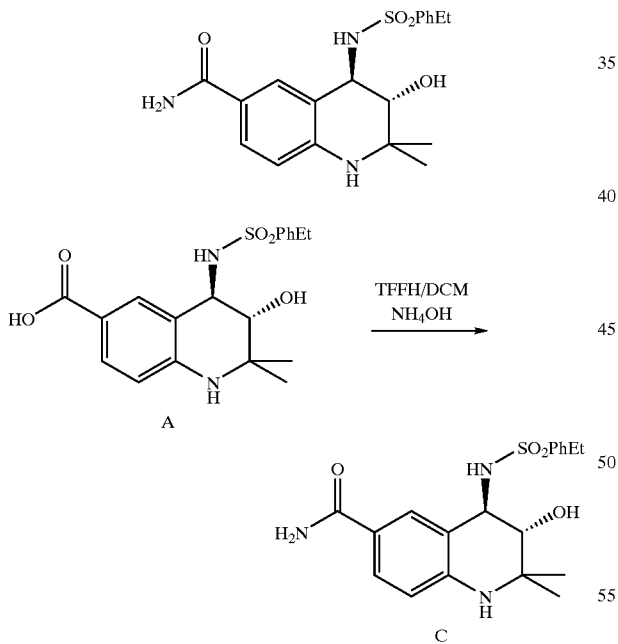

Preparation of A: Compound A was prepared as described in example 268.

Preparation of C: Tetramethylfluoroformamidinium hexafluorophosphate (21 mg, 0.08 mmol) was added to a stirred slurry of A (27 mg, 0.066 mmol) in CH$_2$Cl$_2$ (2 mL). Triethylamine (2 drops) was added and the resulting solution stirred for 1 h then a second portion of TFFH was added (21 mg, 0.08 mmol). The solution was diluted with 10 mL of CH$_2$Cl$_2$, passed through a short pad of silica and concentrated. NH$_4$OH was added to the residue and the crude solution purified by preparative HPLC (YMC PACK S5 ODSA 20×100 mm column. Reversed phase C18) 23–90% MeOH/water with 0.1% TFA linear gradient over 10 min 5 min hold time; 20 mL/in, UV Detection at 220 nm. HPLC: 95% at 2.92 min (YMC S5 ODS 4.6×50 mm Ballistic column) 10–90% MeOH/water with 0.2% H$_3$PO$_4$ linear gradient over 4 min, 4 mL/min, UV Detection at 220 nm. LCMS: 2.95 min (YMC S5 ODS 4.6×50 mm Ballistic column) 10–90% MeOH/water with 0.1% TFA linear gradient over 4 min, 4 mL/min, UV Detection at 220 nm, M+1 404.

EXAMPLE 316

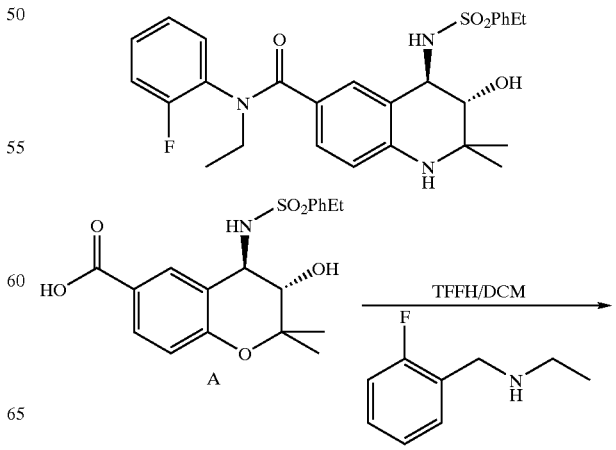

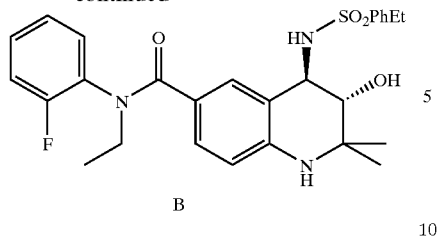

Preparation of A: Compound A was prepared as described in example 1.

Preparation of B: Tetramethylfluoroformamidinium hexafluorophosphate (24 mg, 0.09 mmol) was added to a stirred slurry of benzopyran (34 mg, 0.084 mmol) in CH$_2$Cl$_2$ (2 mL). Triethylamine (3 drops) was added and the resulting solution stirred at ambient temperature for 12 h. The solvents were removed and the crude solution purified by preparative HPLC (YMC PACK S5 ODSA 20×100 mm column Reversed phase C18) 23–90% MeOH/water with 0.1% TFA linear gradient over 10 min 5 min hold time, 20 mL/min, UV Detection at 220 nm. D' was obtained as a pale yellow oil (42 mg, 92%). HPLC: 95% at 4.36 min (YMC S5 ODS 4.6×50 mm Ballistic column) 10–90% MeOH/water with 0.2% H$_3$PO$_4$ linear gradient over 4 min, 4 mL/min, UV Detection at 220 nm. LCMS: 3.96 min (YMC S5 ODS 4.6×50 mm Ballistic column) 10–90% MeOH/water with 0.1% TFA linear gradient over 4 min, 4 mL/min, UV Detection at 220 nm, M+1 541. $^1$HNMR: MeOD 0.94,brs (3H); 1.05, s(3H); 1.10, t, J=7.0 Hz(2H); 1.24, s(3H); 2.57, q, J=6.6 Hz(2H); 3.04, q, J=8.0 Hz(2H); 3.41, d, J=8.0 Hz(1H); 4.18, d, J=8.0 Hz(1H); 4.7, brs(2H); 6.4–7.3, m(6H); 7.73, d, J=8.0 Hz.

EXAMPLE 317

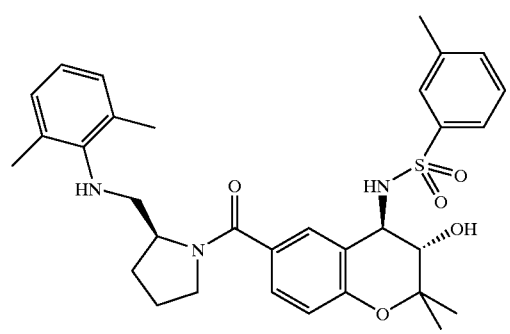

= styrene divinylbenzene copolymer

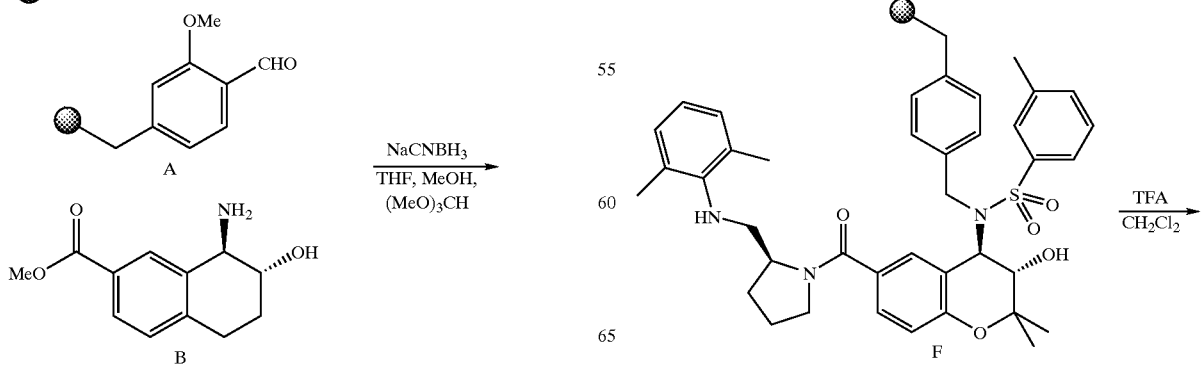

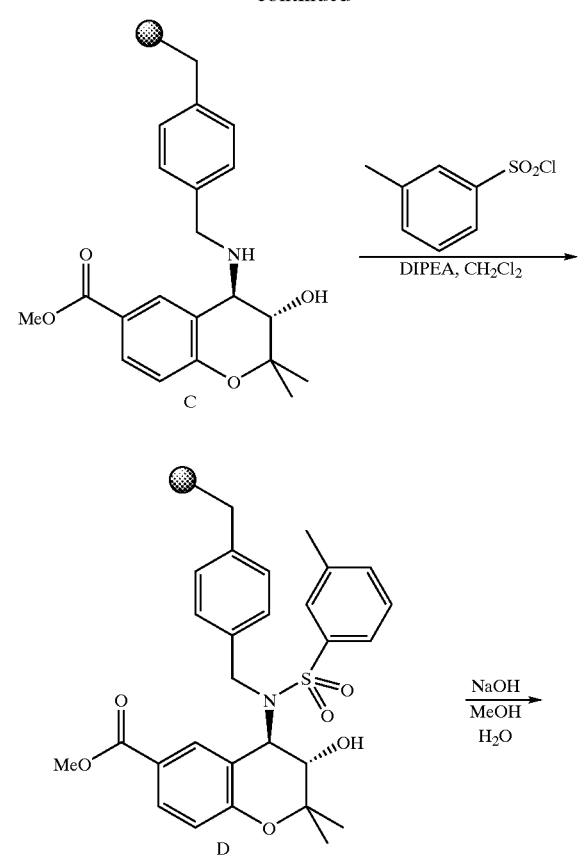

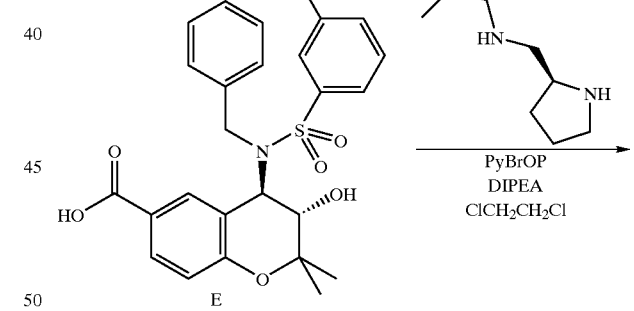

191

-continued

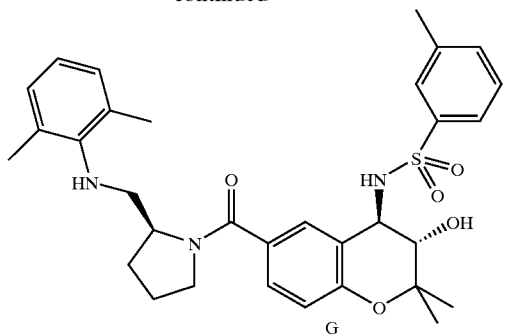

G

Preparation of A: The polystyrene resin bound aldehyde was prepared as described in Sarantakis, D.; Bicksler, J. J.; *Tetrahedron Letters* 1997, 38 (42), 7325–7328.

Preparation of B The benxopyran ester was synthesized from the the example 1 part A compound by standard methods.

Preparation of C: The resin bound aldehyde (10 g, 1 mmol/g loading, 10 mmol) was suspended in 75 mL tetrahydrofuran, 25 mL methanol and 25 mL trimethylorthoformate. Acetic acid (2 mL) was added followed by compound B (3.77 g, 15 mmol) and the reaction was shaken for 16 hrs. The mixture was then filtered and washed with THF then methanol and dried to provide 11.64 g of resin.

Preparation of D: The resin C (100 mg, 0.087 mmol) was suspended in 1 mL of dichloromethane and N, N-diisopropylethylamine (23 µL, 0.13 mmol) and 3-toluenesulfonyl chloride (0.5 mL, 0.26 M in dichloromethane, 0.13 mmol) were added. The reaction was shaken for 16 hrs. The mixture was the filtered and washed with dichloromethane then tetrahydrofuran and dried in vacuo.

Preparation of E; The resin D was suspended in 2 mL 50% methanol in tetrahydrofuran and sodium hydroxide was added (174 µL, 1.74 mmol). The reaction was heated to 40° and shaken for 24 hrs. The mixture was filtered the washed with 50% methanol in Tetrahydrofuran the with methanol and dried in vacuo.

Preparation of F: The resin E was suspended in a solution of (S)-(+)-2-(2,6-xylidinomethyl)pyrrolidine [70371-56-1] (1 mL, 0.43 M in dichloroethane, 0.43 mmol) and diisopropylethylamine (151 µL, 0.87 mmol) was added. Bromo-trispyrrolidinophosphonium hexafluorophosphate (PyBroP) (1 mL, 0.43 M in dichloroethane, 0.43 mmol) was added and the reaction was shaken for 24 hrs at 70°. The mixture was filtered the washed with dichloromethane and dried in vacuo.

Preparation of G: The resin F was suspended in 2 mL of 50% trifluoroacetic acid in dichloromethane. The reaction was shaken for 1 hr the filtered and washed with dichloromethane. The filtrate was combined and the solvent removed. The residue was dissolved in 1 mL of acetonitrile and loaded onto a strong cation exchange cartridge (Varian 3 g SAX). The cartridge was washed with 10 mL 0.05 M ammonia methanol then eluted with 10 mL of 1 M ammonia methanol. The solvent was removed from the 1 M ammonia fraction to provide 26 mg (52%) of a white solid.

The following examples were synthesized by the methods described in example 317 except that the compounds that are not basic were purified by dissolving the residue in acetonitrile and loading it onto a mixed SCX and SAX cartridge and eluting the product with acetonitrile.

| Example | Structure | Mass spec M/Z |
| --- | --- | --- |
| 318 | 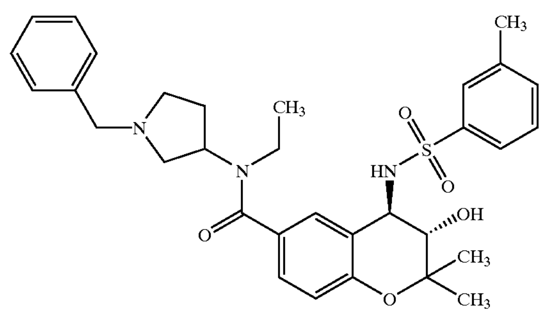 | 578 (M + H) |
| 319 | 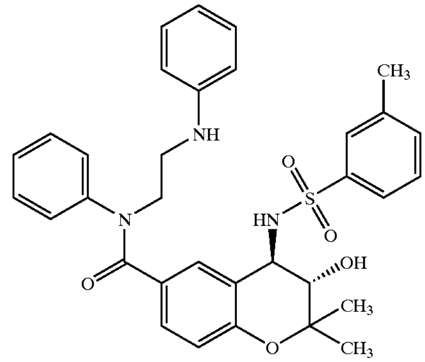 | 586 (M + H) |

-continued

| Example | Structure | Mass spec M/Z |
|---|---|---|
| 320 | 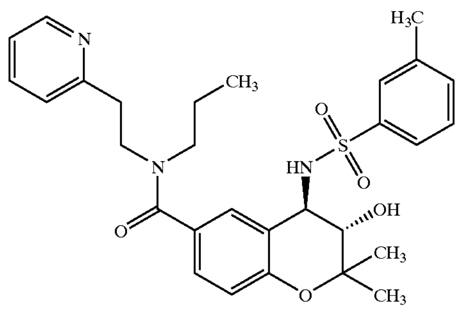 | 538 (M + H) |
| 321 | 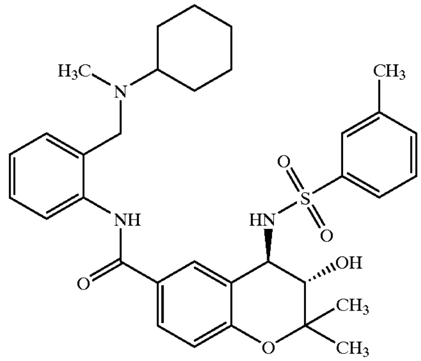 | 592 (M + H) |
| 322 | 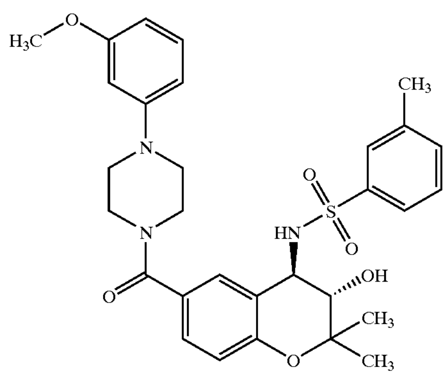 | 566 (M + H) |
| 323 | 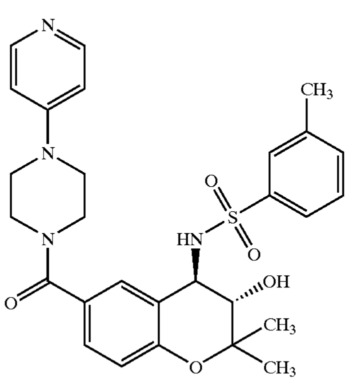 | 537 (M + H) |

-continued

| Example | Structure | Mass spec M/Z |
|---|---|---|
| 324 | 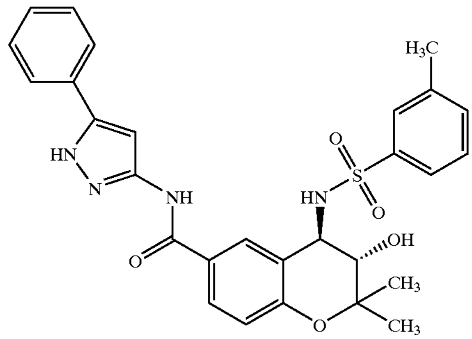 | 533 (M + H) |
| 325 | 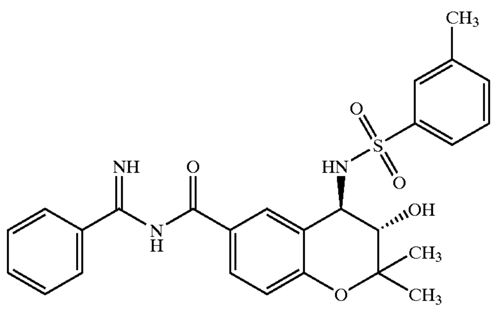 | 494 (M + H) |
| 326 | 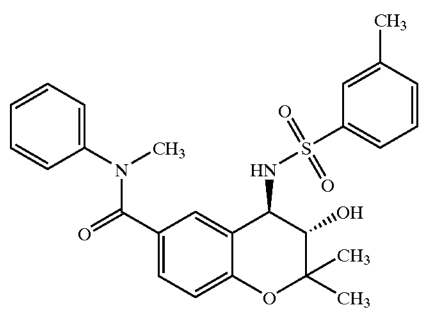 | 481 (M + H) |
| 327 | 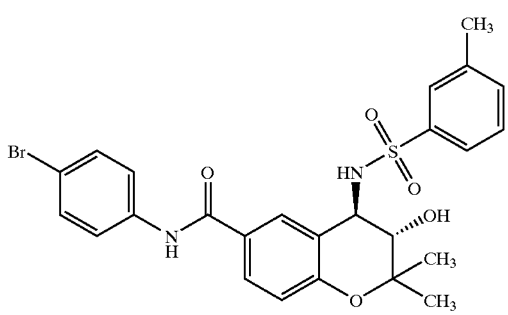 | 546 (M + H) |
| 328 | 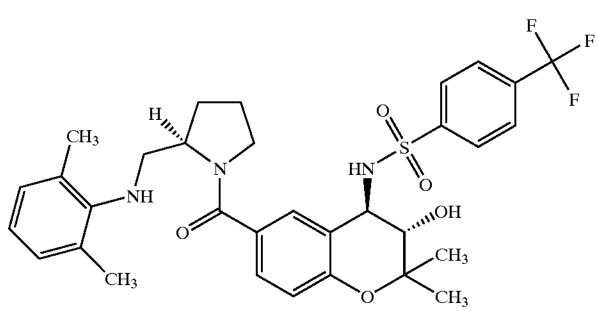 | 632 (M + H) |

-continued
| Example | Structure | Mass spec M/Z |
|---|---|---|
| 329 | 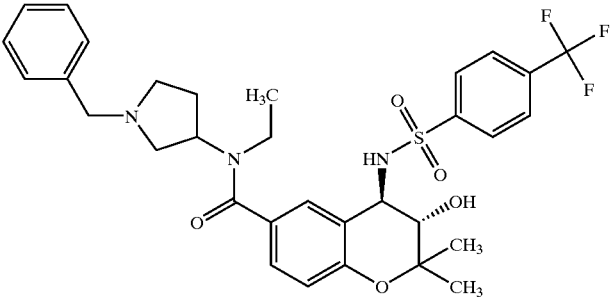 | 632 (M + H) |
| 330 | 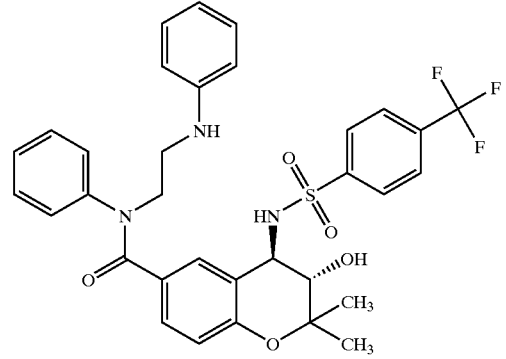 | 640 (M + H) |
| 331 | 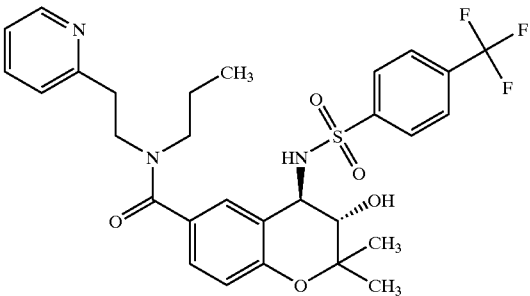 | 592 (M + H) |
| 332 | 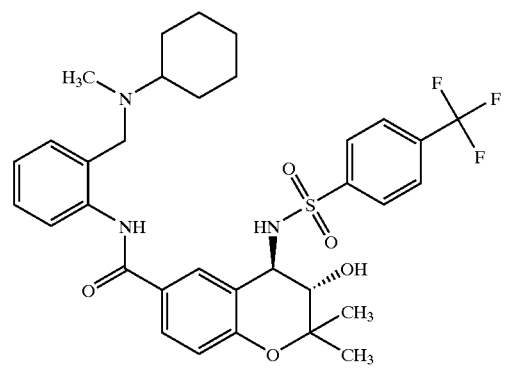 | 646 (M + H) |

| Example | Structure | Mass spec M/Z |
|---|---|---|
| 333 | 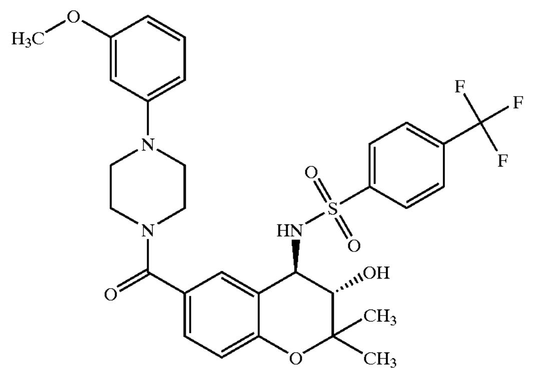 | 620 (M + H) |
| 334 | 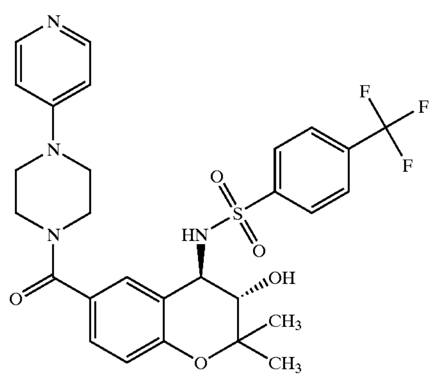 | 591 (M + H) |
| 335 | 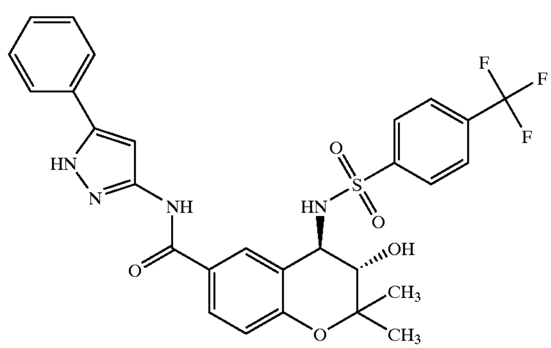 | 587 (M + H) |
| 336 | 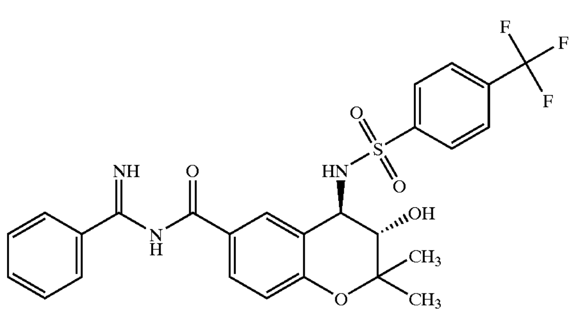 | 548 (M + H) |

-continued

| Example | Structure | Mass spec M/Z |
|---|---|---|
| 337 | 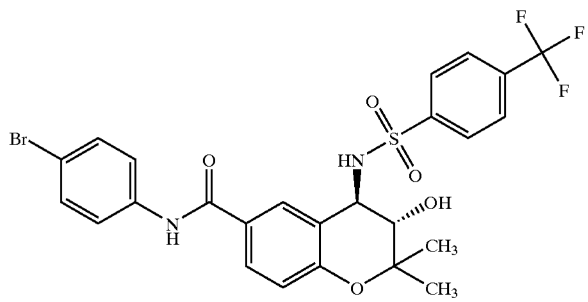 | 600 (M + H) |
| 338 | 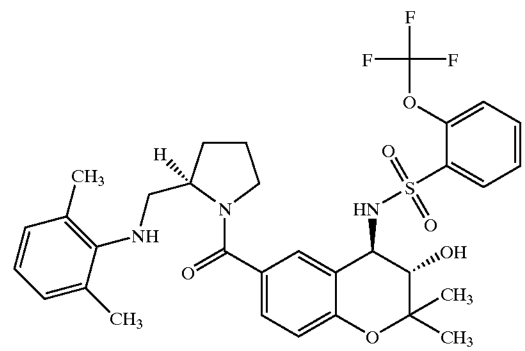 | 648 (M + H) |
| 339 | 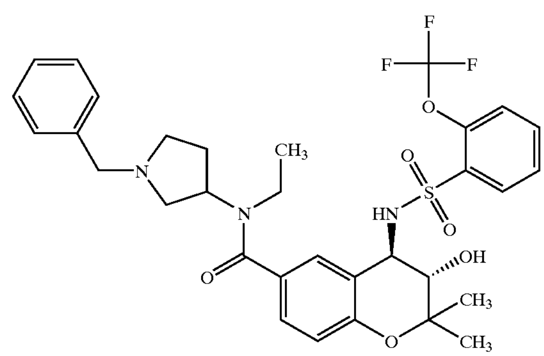 | 648 (M + H) |
| 340 | 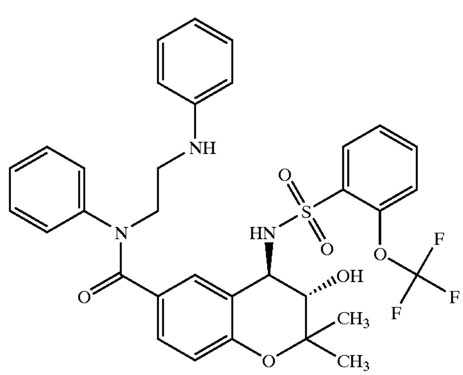 | 656 (M + H) |

-continued

| Example | Structure | Mass spec M/Z |
|---|---|---|
| 341 | 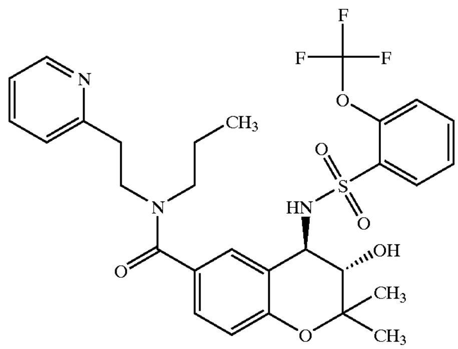 | 608 (M + H) |
| 342 | 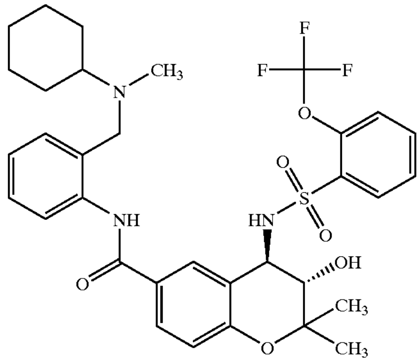 | 662 |
| 343 | 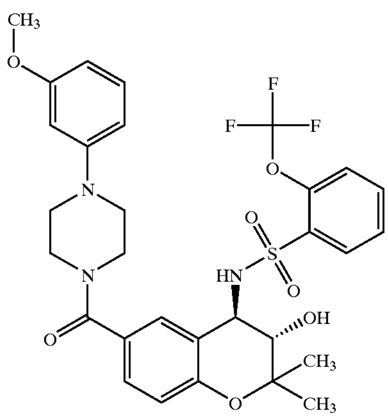 | 636 (M + H) |
| 344 | 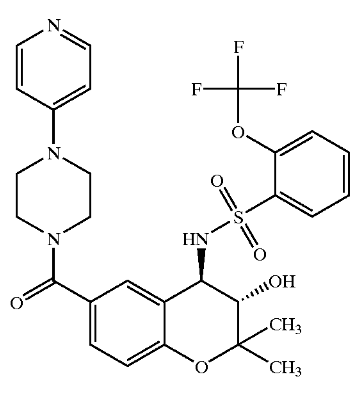 | 607 (M + H) |

-continued

| Example | Structure | Mass spec M/Z |
|---------|-----------|---------------|
| 345 | 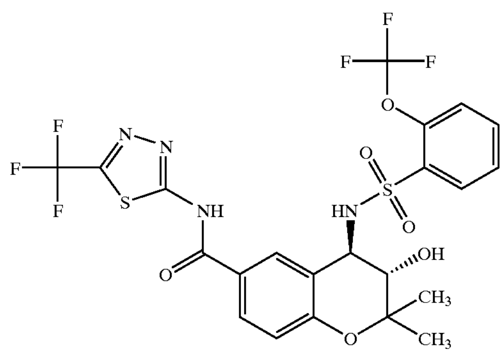 | 613 (M + H) |
| 346 | 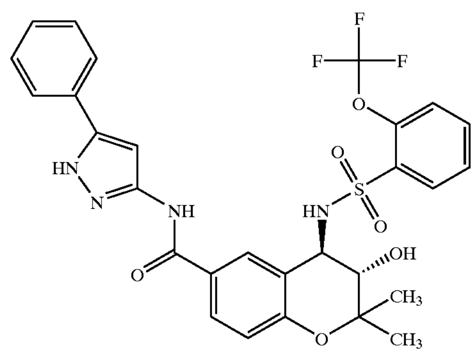 | 603 (M + H) |
| 347 | 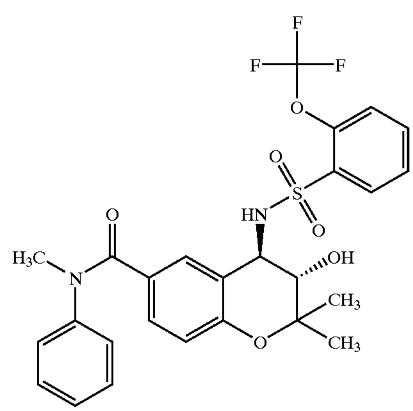 | 551 (M + H) |
| 348 | 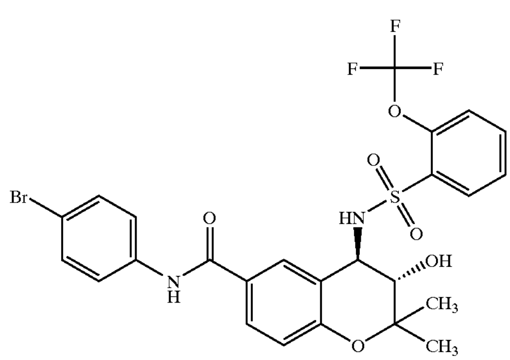 | 615 (M + H) |

-continued

| Example | Structure | Mass spec M/Z |
|---|---|---|
| 349 | 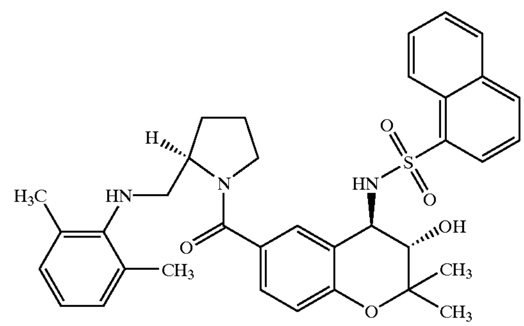 | 614 (M + H) |
| 350 | 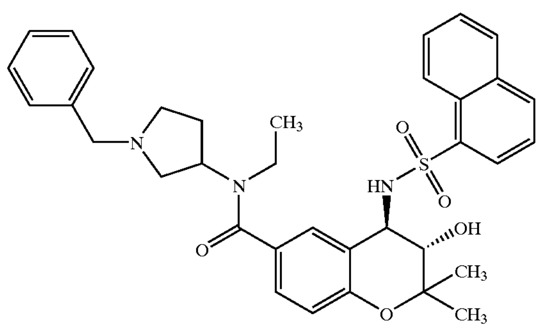 | 614 (M + H) |
| 351 | 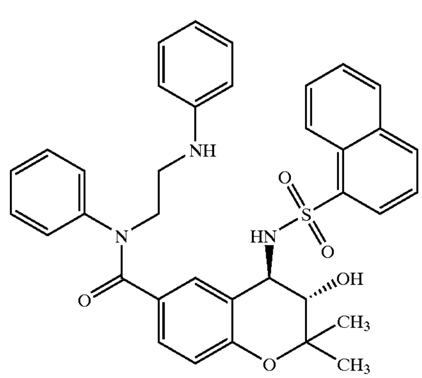 | 622 (M + H) |
| 352 | 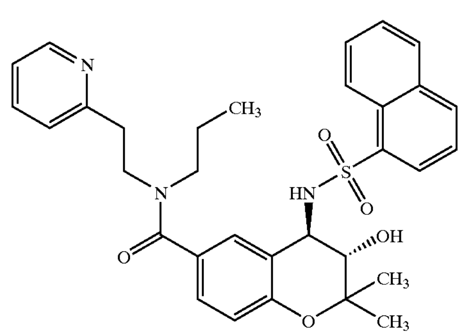 | 574 (M + H) |

-continued

| Example | Structure | Mass spec M/Z |
|---------|-----------|---------------|
| 353 | 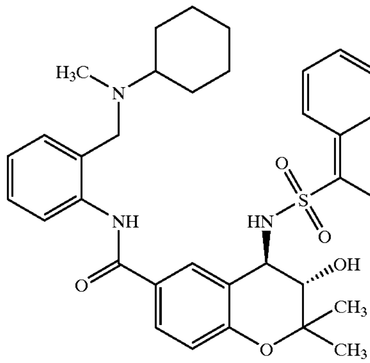 | 628 (M + H) |
| 354 | 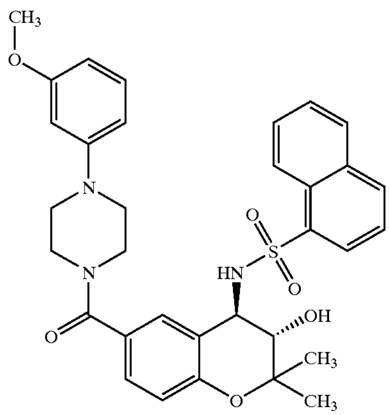 | 602 (M + H) |
| 355 | 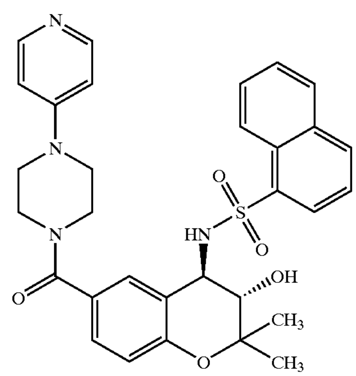 | 573 (M + H0 |
| 356 | 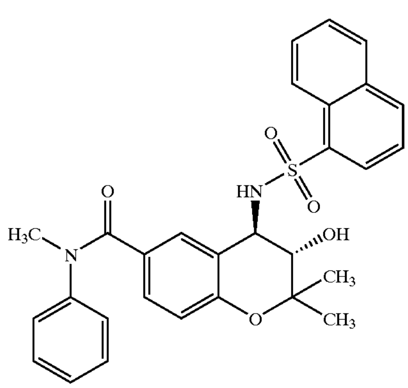 | 517 (M + H) |

| Example | Structure | Mass spec M/Z |
|---|---|---|
| 357 | 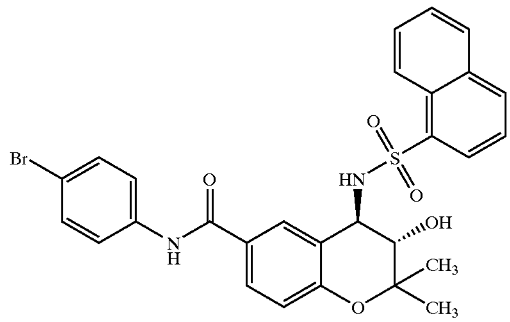 | 581 (M + H) |
| 358 | 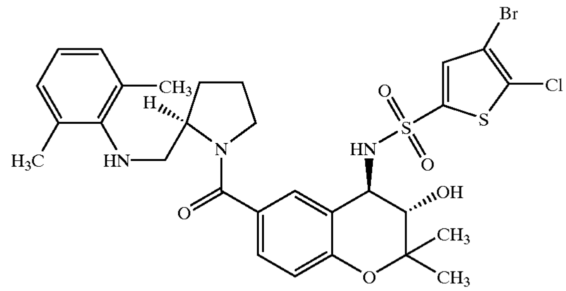 | 682 (M + H) |
| 359 | 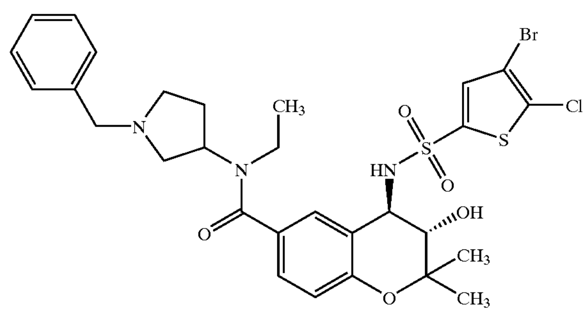 | 682 (M + H) |
| 360 | 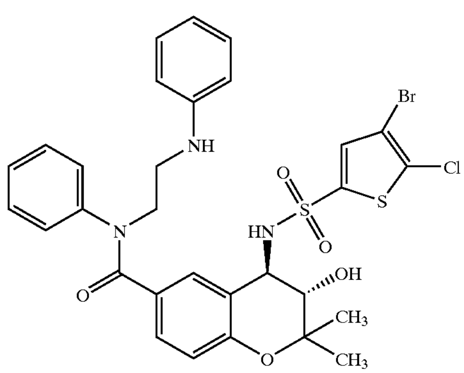 | 690 (M + H) |

-continued

| Example | Structure | Mass spec M/Z |
|---|---|---|
| 361 | 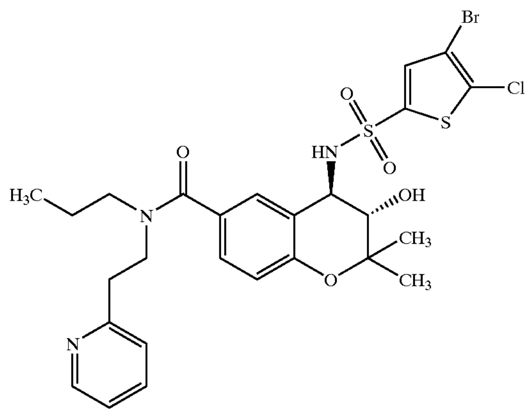 | 642 (M + H) |
| 362 | 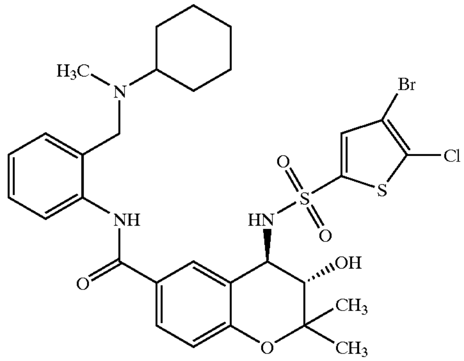 | 696 (M + H) |
| 363 | 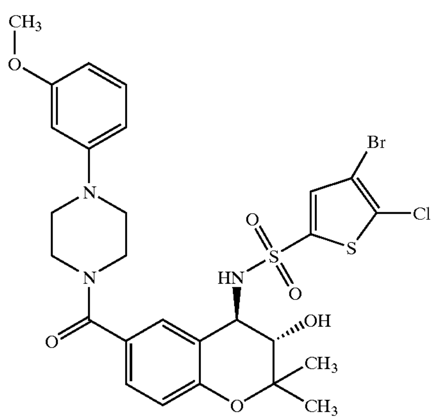 | 670 (M + H) |
| 364 | 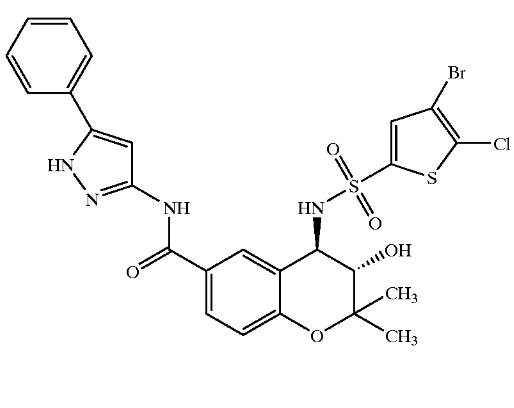 | 637 |

| Example | Structure | Mass spec M/Z |
|---|---|---|
| 365 | 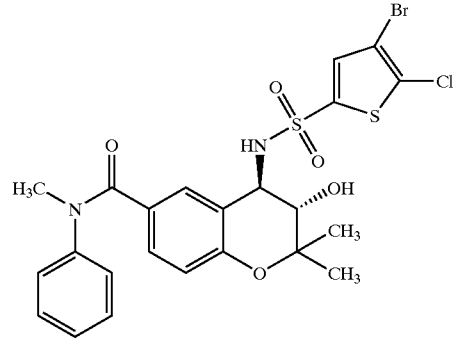 | 585 (M + H) |
| 366 | 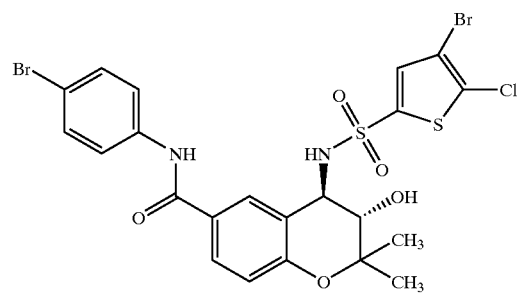 | 649 (M + H) |
| 367 | 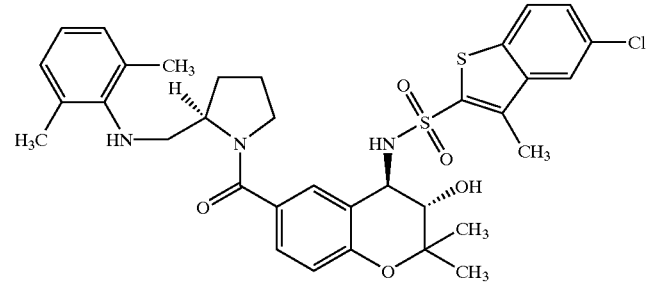 | 668 (M + H) |
| 368 | 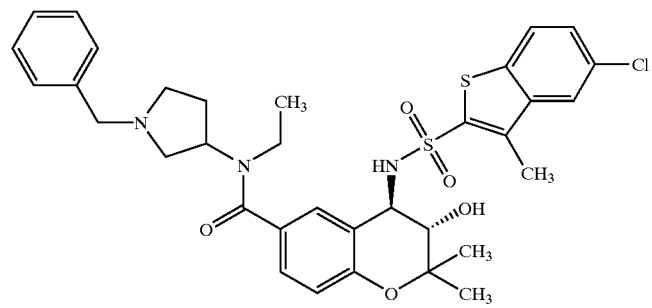 | 668 (M + H) |

-continued

| Example | Structure | Mass spec M/Z |
|---------|-----------|---------------|
| 369 | 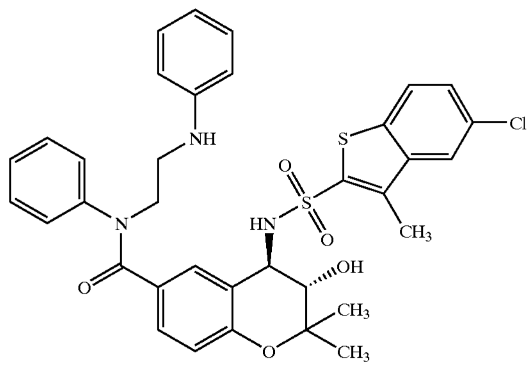 | 676 (M + H) |
| 370 | 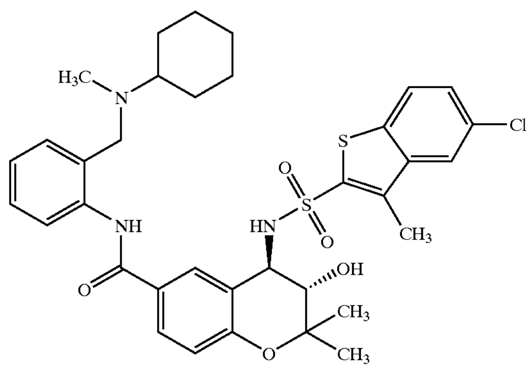 | 682 (M + H) |
| 371 | 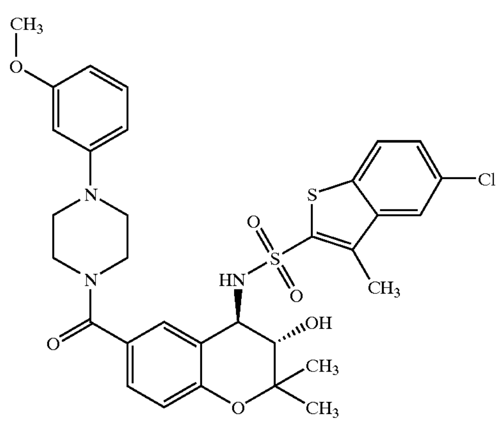 | 656 (M + H) |
| 372 | 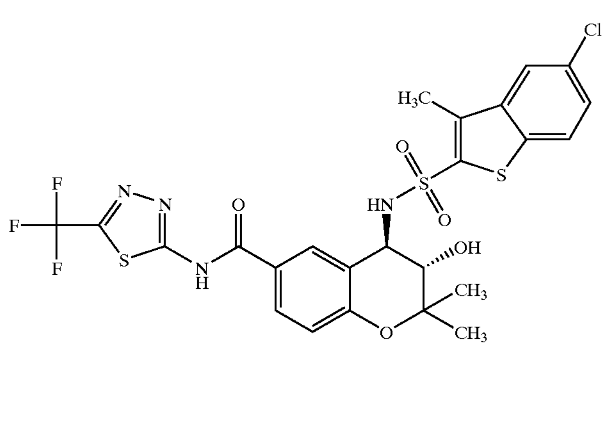 | 633 (M + H) |

-continued
| Example | Structure | Mass spec M/Z |
|---|---|---|
| 373 | 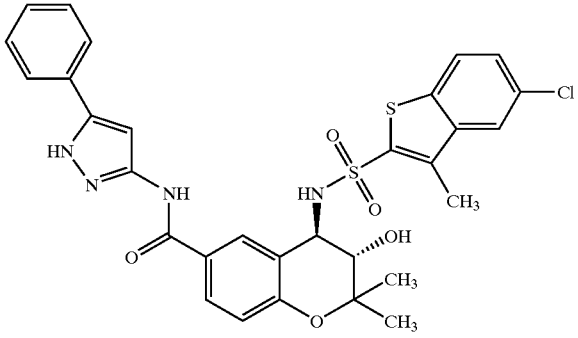 | 632 (M + H) |
| 374 | 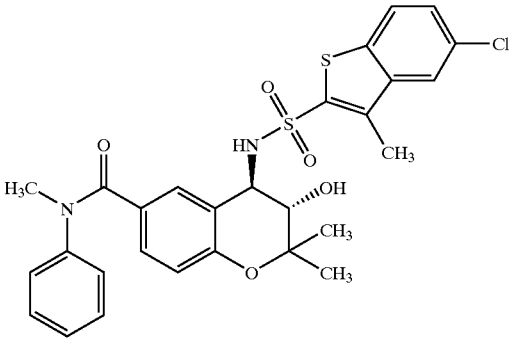 | 571 (M + H) |
| 375 | 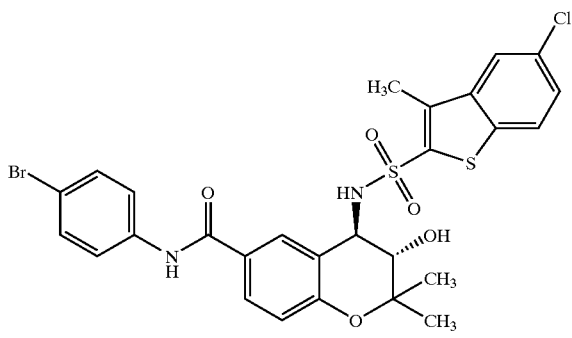 | 635 (M + H) |
| 376 | 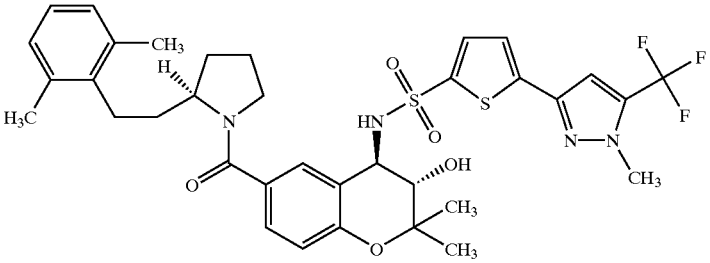 | 718 (M + H) |

-continued

| Example | Structure | Mass spec M/Z |
|---|---|---|
| 377 | 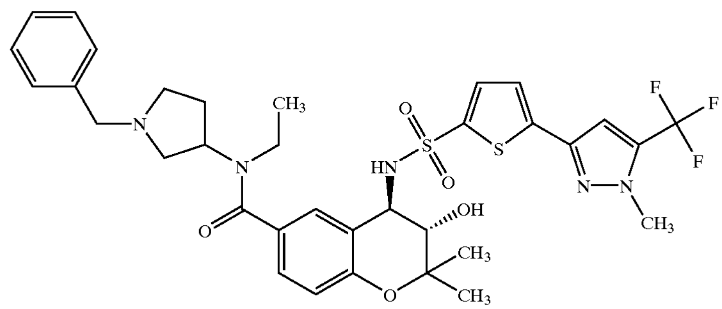 | 718 (M + H) |
| 378 | 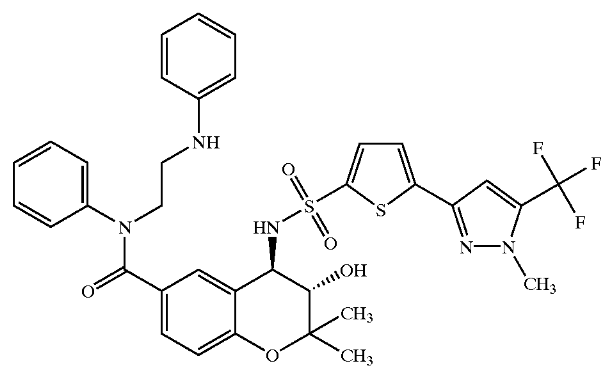 | 726 (M + H) |
| 379 | 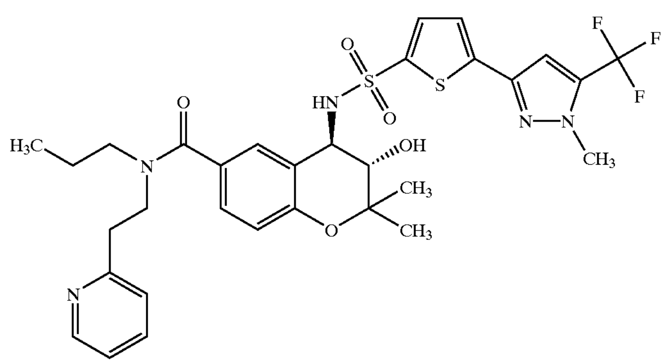 | 678 (M + H) |
| 380 | 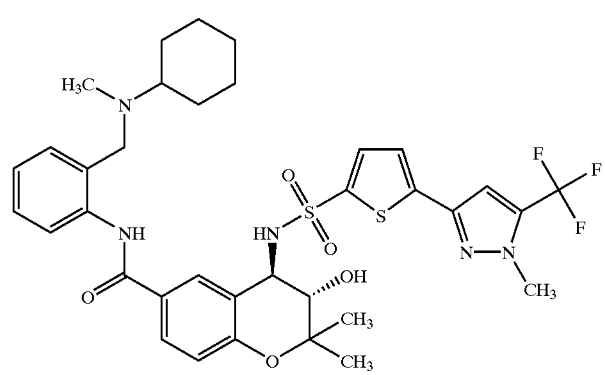 | 732 (M + H) |

-continued

| Example | Structure | Mass spec M/Z |
|---------|-----------|---------------|
| 381 | 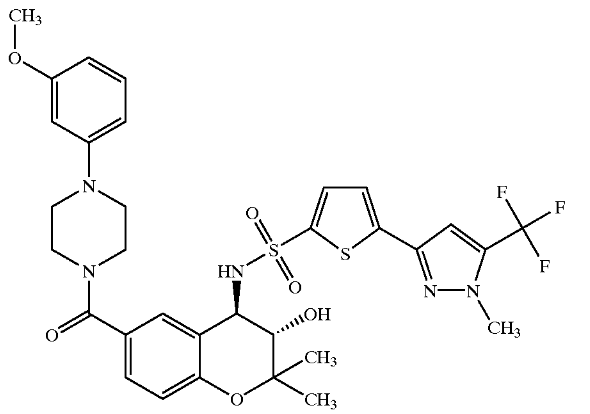 | 706 (M + H) |
| 382 | 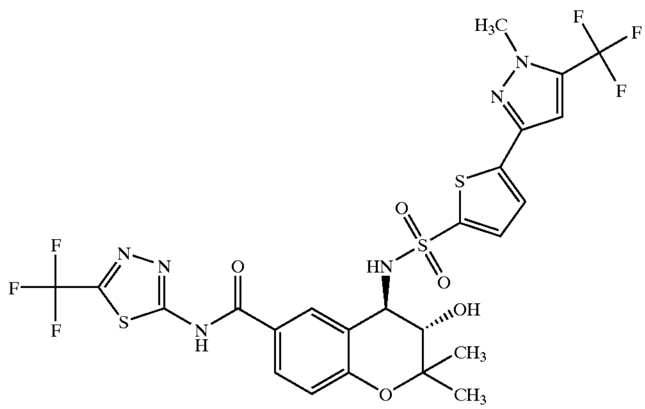 | 683 (M + H) |
| 383 | 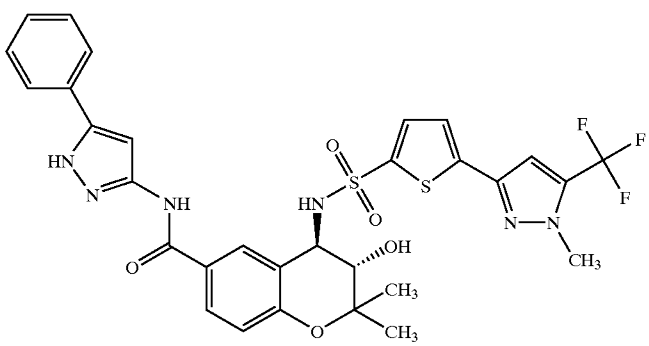 | 673 (M + H) |
| 384 | 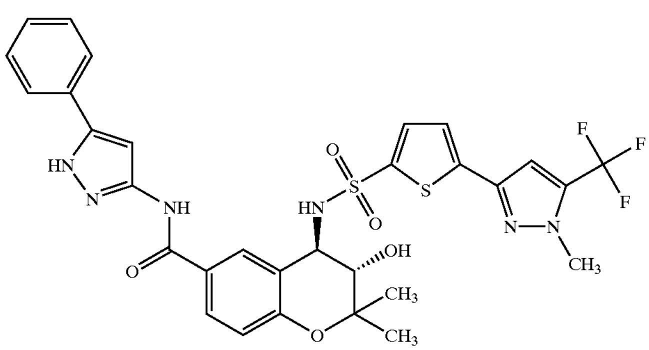 | 673 (M + H) |

-continued

| Example | Structure | Mass spec M/Z |
|---|---|---|
| 385 | 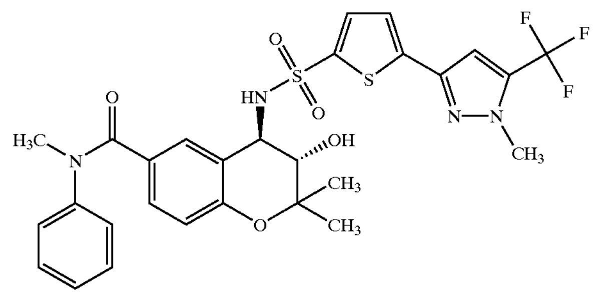 | 621 (M + H) |
| 386 | 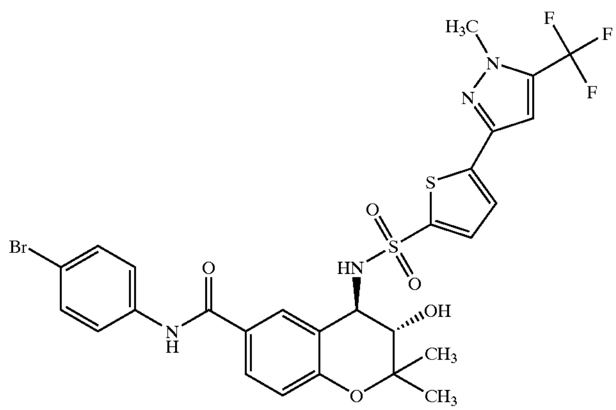 | 685 (M + H) |
| 387 | 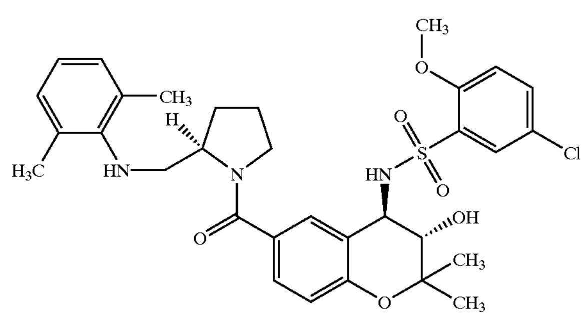 | 629 (M + H) |
| 388 | 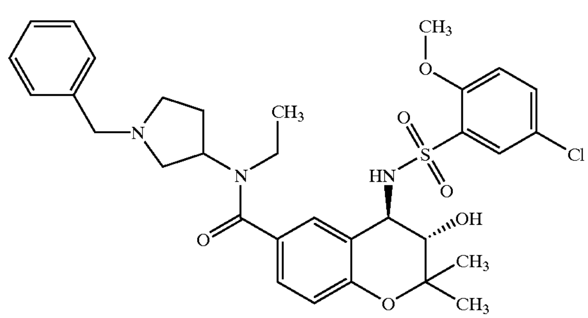 | 628 (M + H) |

| Example | Structure | Mass spec M/Z |
|---|---|---|
| 389 | 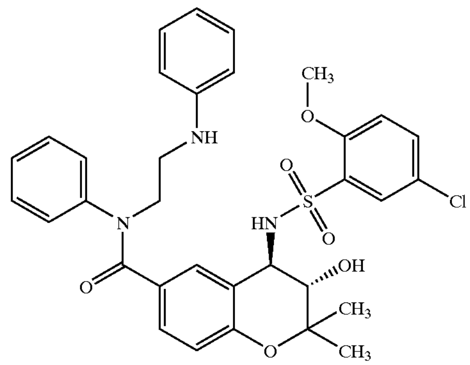 | 636 (M + H) |
| 390 | 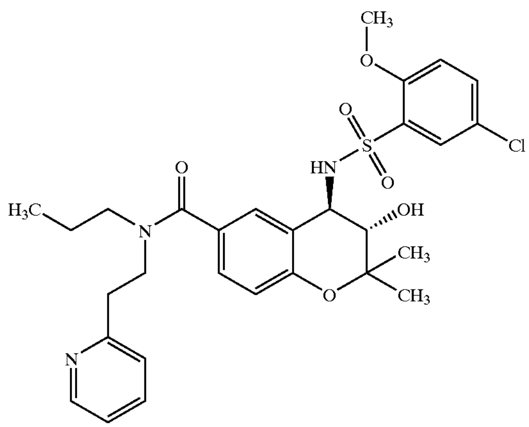 | 588 (M + H) |
| 391 | 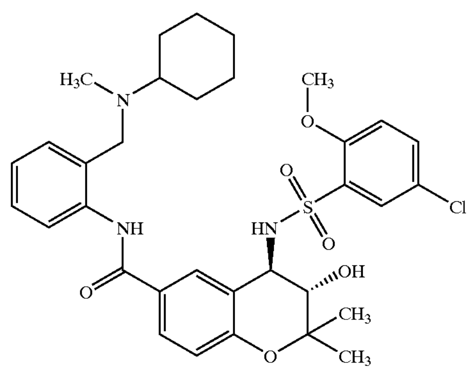 | 642 (M + H) |
| 392 | 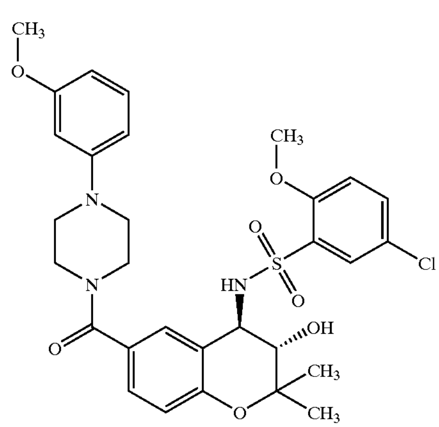 | 616 (M + H) |

-continued

| Example | Structure | Mass spec M/Z |
|---|---|---|
| 393 | 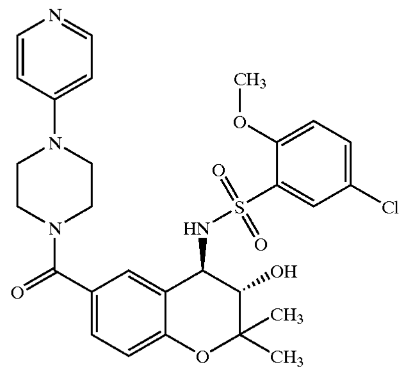 | 587 (M + H) |
| 394 | 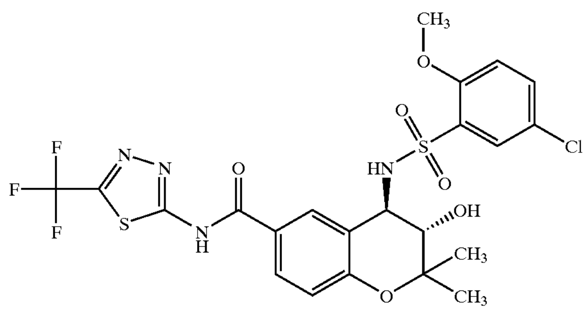 | 593 (M + H) |
| 395 | 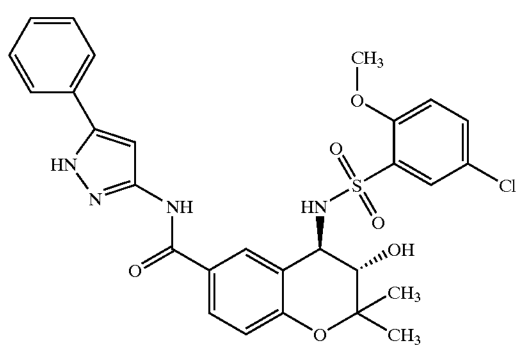 | 583 (M + H) |
| 396 | 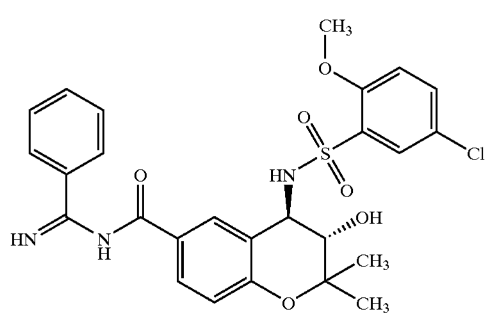 | 544 (M + H) |

| Example | Structure | Mass spec M/Z |
|---|---|---|
| 397 | 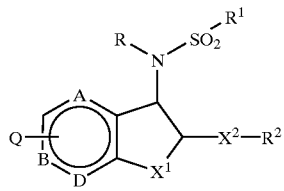 | 531 (M + H) |
| 398 | 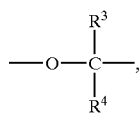 | 595 (M + H) |

What is claimed is:

1. A compound having the structure

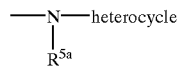

or pharmaceutically acceptable salts thereof, prodrug esters thereof, or all stereoisomers thereof, wherein A and B are CH and D is N;

$X^1$ is

wherein the heteroatom is linked to the aromatic ring; (where $R^3$ and $R^4$ are independently H, alkyl, arylalkyl or cycloalkyl, or $R^3$ and $R^4$ can be taken together with the carbon to which they are attached to form a 5 to 8 carbon containing ring);

R is H, alkyl, alkenyl, aryl, arylalkyl, heterocycloalkyl, cycloalkyl, or cycloalkylalkyl;

$R^1$ is arylalkyl, aryl, alkenyl, heteroaryl, heteroarylalkyl,

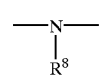

(where $R^{5a}$ is H, alkyl, alkenyl, aryl, arylalkyl, cycloalkyl or cycloalkylalkyl), or

—N(R⁶)—R⁷

(where $R^6$ and $R^7$ are independently selected from aryl, arylalkyl or cycloalkyl;

$X^2$ is a single bond,

—N(R⁸)— or —O— (where $R^8$ is H, alkyl, alkenyl, aryl, arylalkyl, cycloalkyl or cycloalkylalkyl);

$R^2$ is H, alkyl, arylalkyl,

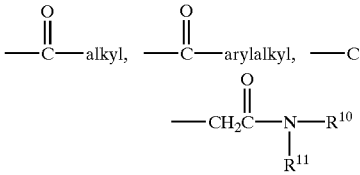

(where $R^{10}$ and $R^{11}$ are independently selected from H, alkyl, arylalkyl or cycloalkyl, or $R^{10}$ and $R^{11}$ can be taken together with the nitrogen to which they are attached to form a 5- to 8-membered ring); and

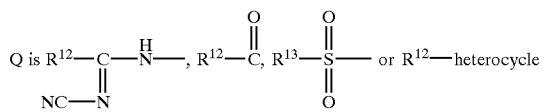

(where $R^{12}$ is alkyl, arylalkyl, aryl,

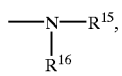

heterocycle, heterocycloalkyl,

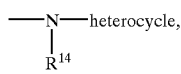

(where $R^{14}$ can be any of the $R^8$ groups), alkoxy, $CF_3$, aryloxy, arylalkoxy, cycloalkyl or cycloalkylalkyl, and where $R^{15}$ and $R^{16}$ are independently selected from H, alkyl, arylalkyl, aryl, heterocyclo, cycloalkyl, amino, aminoalkyl, or heterocycloalkyl, or $R^{15}$ and $R^{16}$ can be taken together with the nitrogen to which they are attached to form a 5- to 8-membered ring which may optionally contain an additional nitrogen atom in the ring and/or an amino group or an aminoalkyl group attached to the ring); and $R^{13}$ is

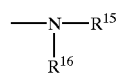

(wherein this moiety is as defined with respect to $R^{12}$).

2. The compound as defined in claim 1 having the structure

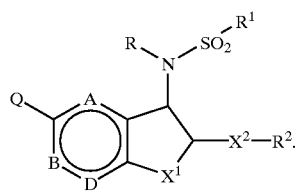

3. The compound as defined in claim 1 having the structure

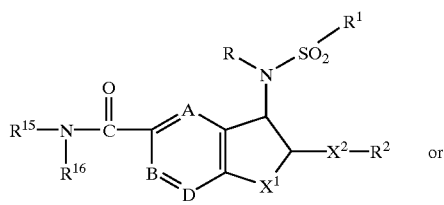

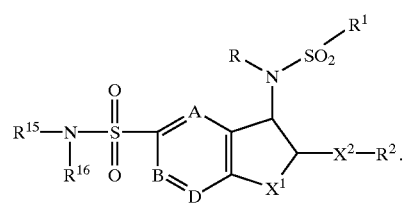

4. The compound as defined in claim 1 having the structure

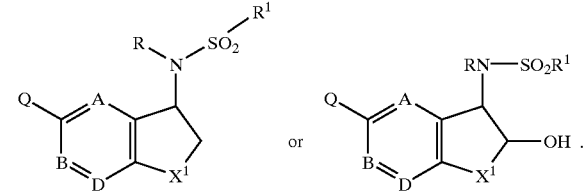

5. The compound as defined in claim 1 wherein

R is H;

$R^1$ is aryl;

$X^2$ is O or a single bond;

$R^2$ is H;

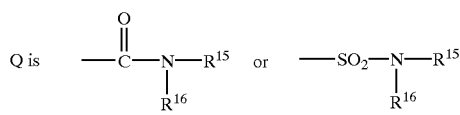

where $R^{15}$ and $R^{16}$ are independently H, aryl, aralkyl or aminoalkyl.

6. The compound as defined in claim 1 having the structure

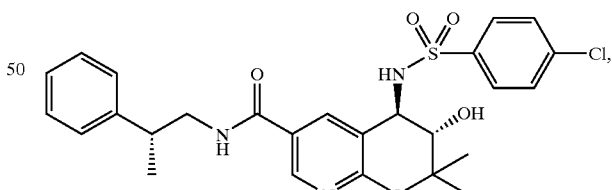

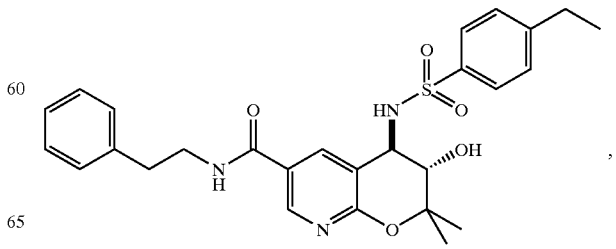

235
-continued
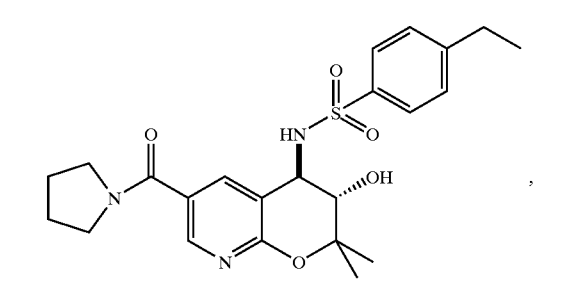
,
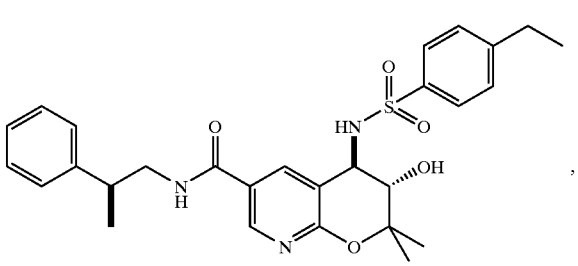
,
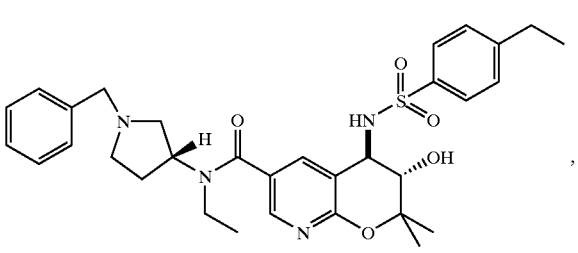
,
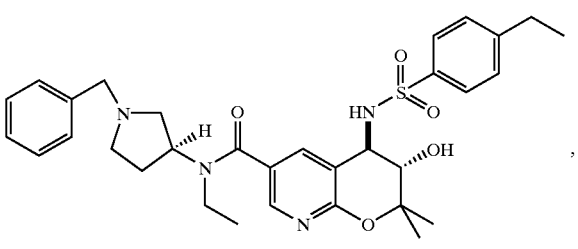
,
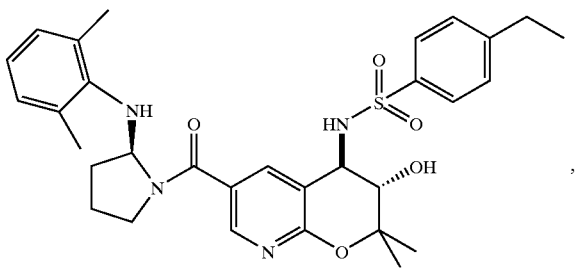
,
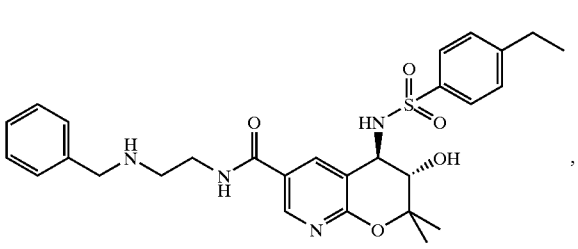
,
236
-continued
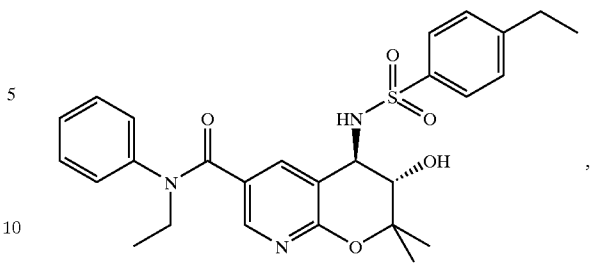
,
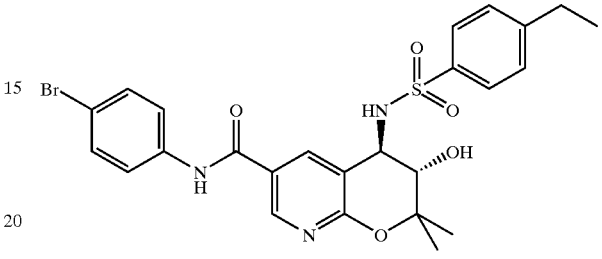
,
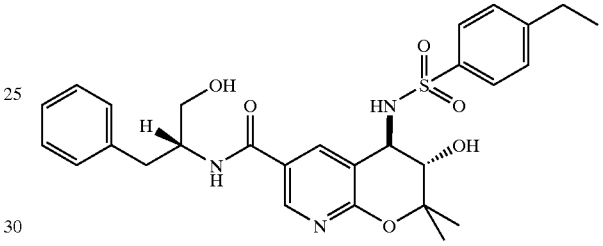
,
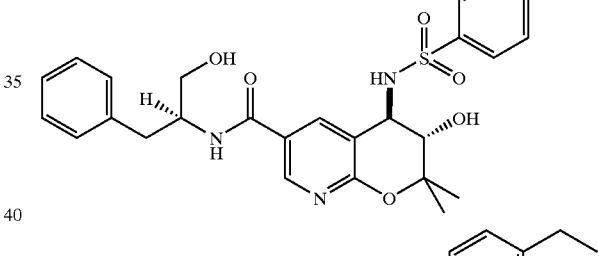
,
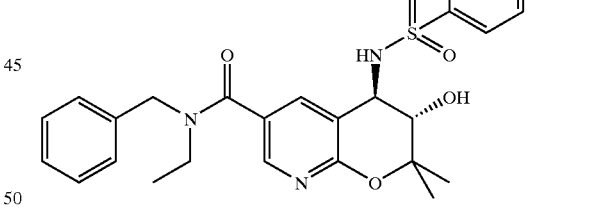
,
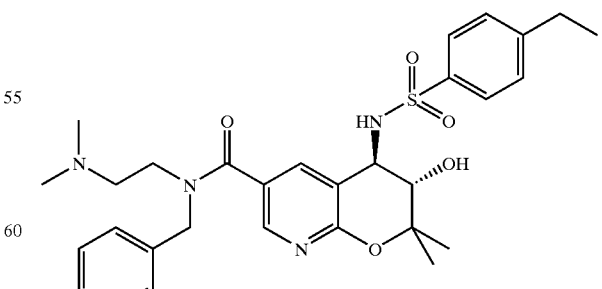
or

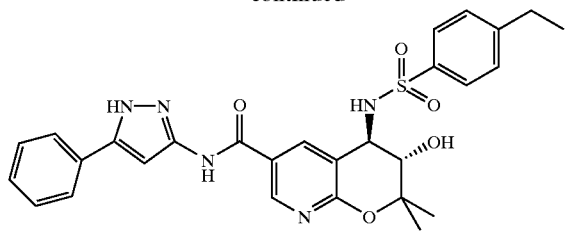

7. A compound having the structure

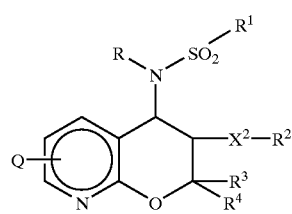

where R is H

R[1] is phenyl or phenyl substituted with alkyl or halogen;
$X^2$ is O;
$R^2$ is H;
$R^3$ is alkyl;
$R^4$ s alkyl;
and Q is

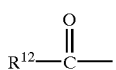

where

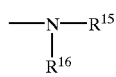

where $R^{15}$ and $R^{16}$ are independently selected from H, alkyl, arylalkyl, aryl, heterocyclo, cycloalkyl, amino, aminoalkyl or heterocycloalkyl or $R^{15}$ and $R^{16}$ can be taken together with the nitrogen to which they are attached to form a 5- to 8-membered ring which may optionally contain an additional nitrogen atom in the ring and/or an amino group or an aminoalkyl group attached to the ring.

8. The compound as defined in claim 7 wherein $R^1$ is p-ethylphenyl or p-chlorophenyl.

9. The compound as defined in claim 1 having the structure

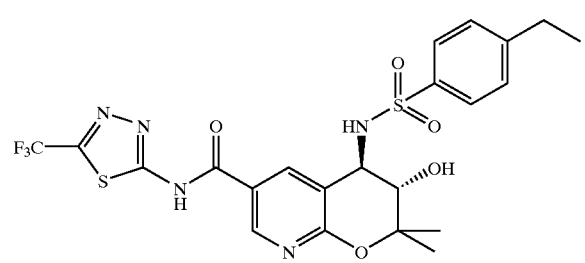

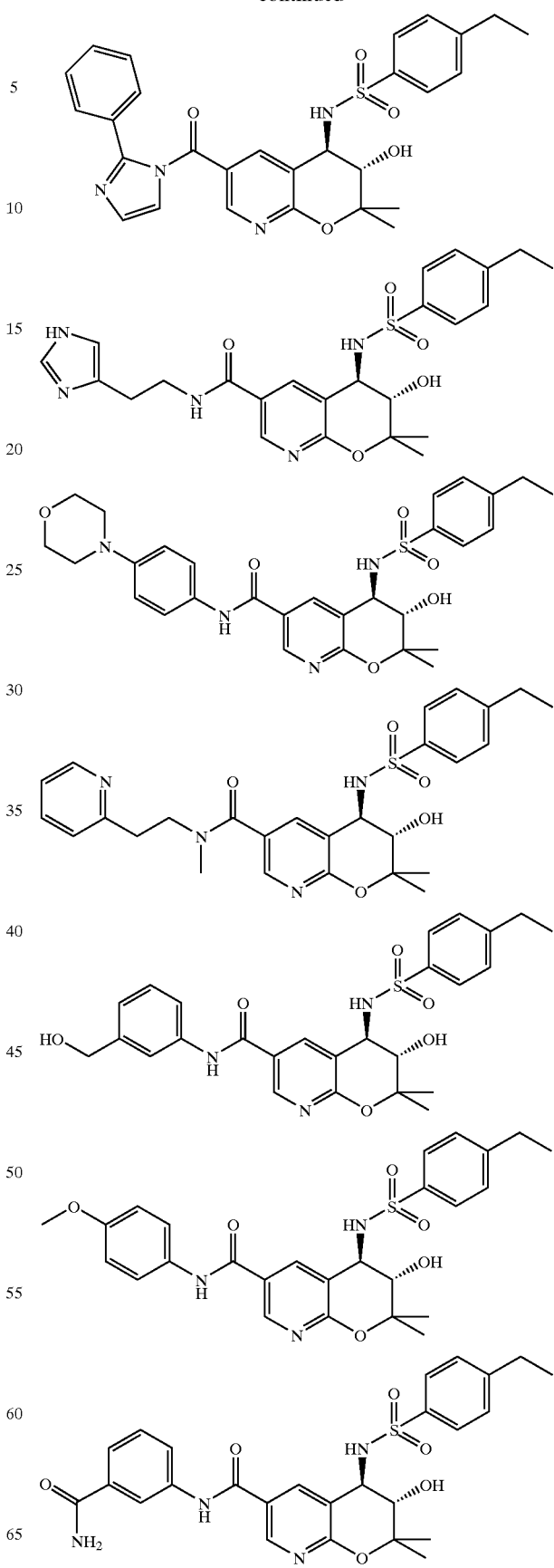

239
-continued
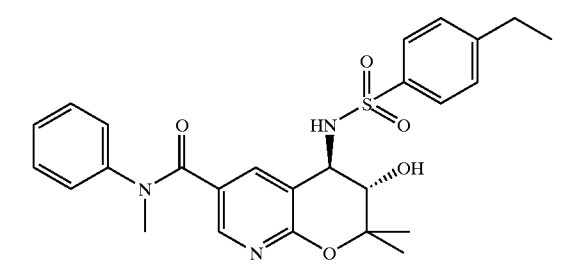
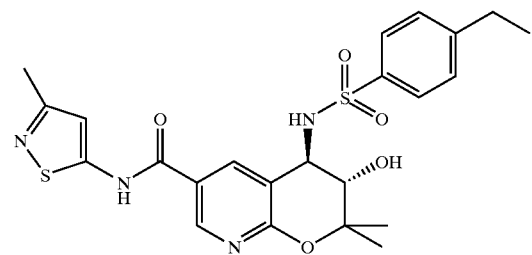
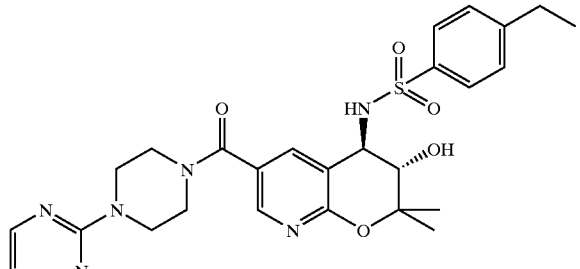
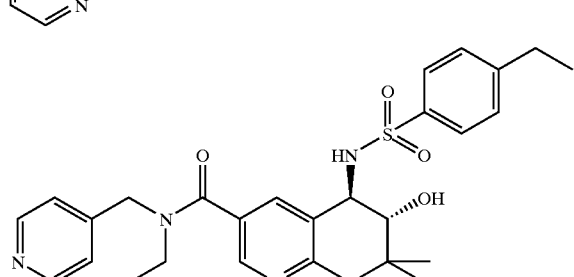
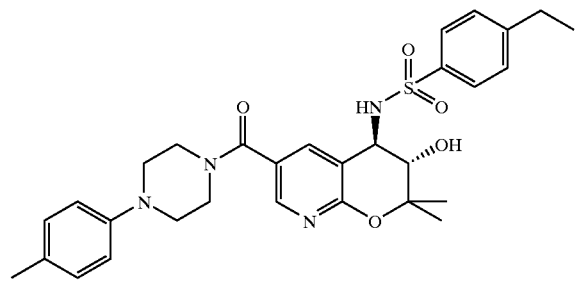
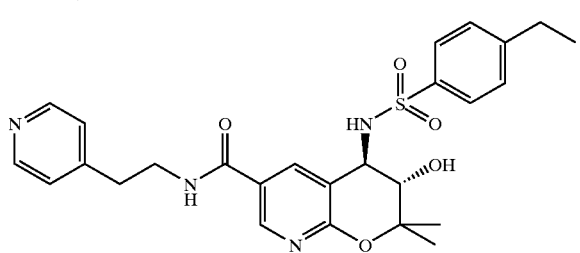
240
-continued
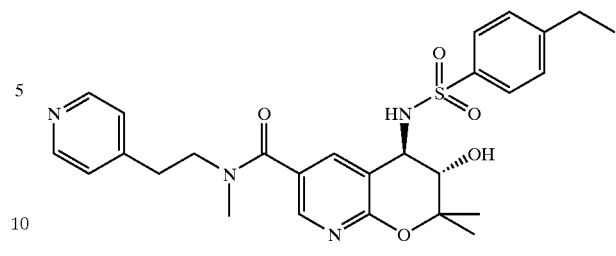
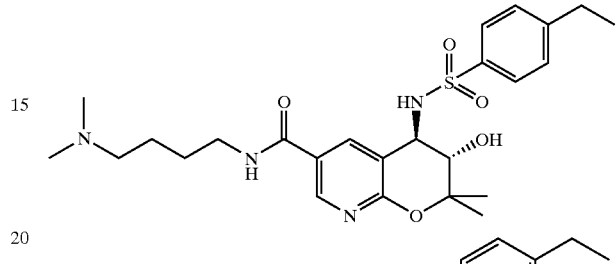
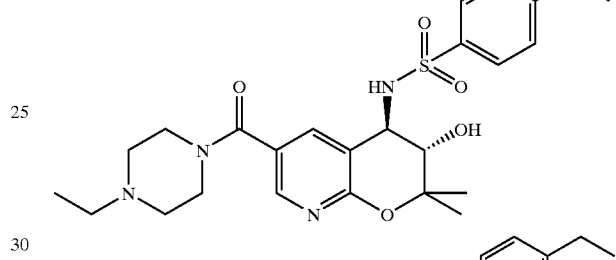
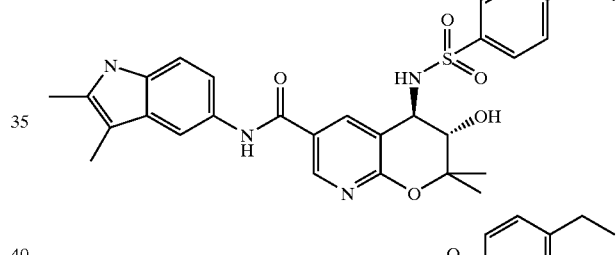
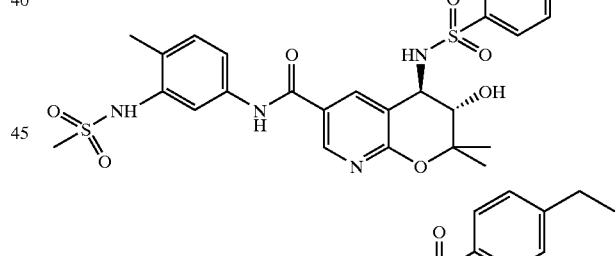
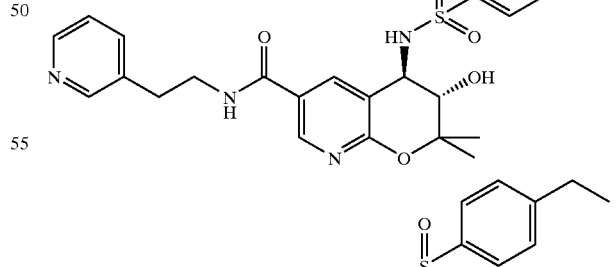

241
-continued
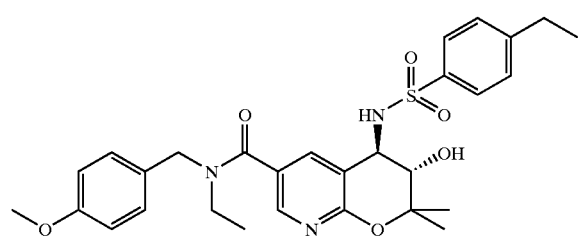
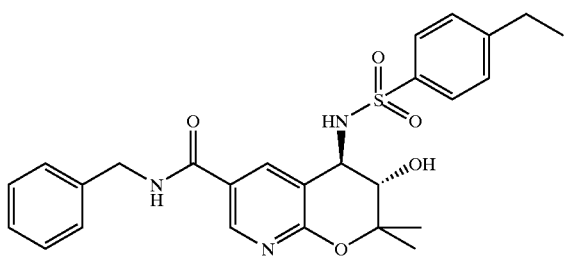
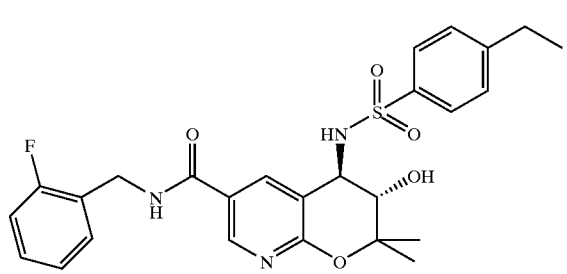
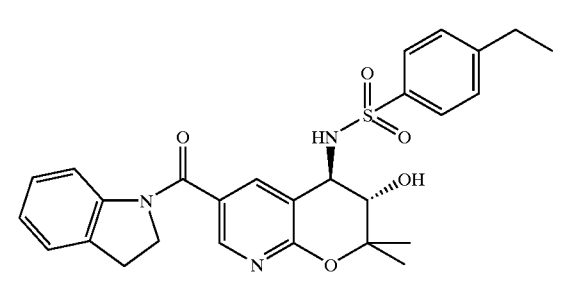
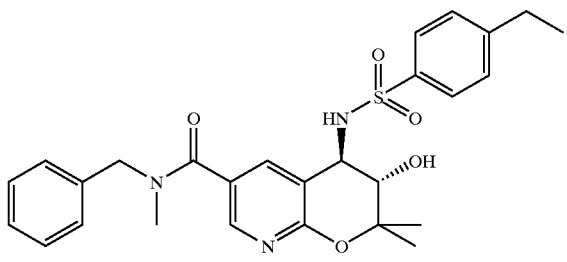
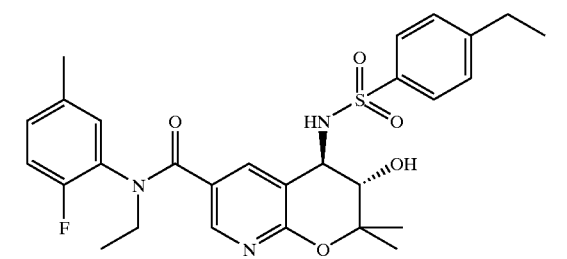
242
-continued
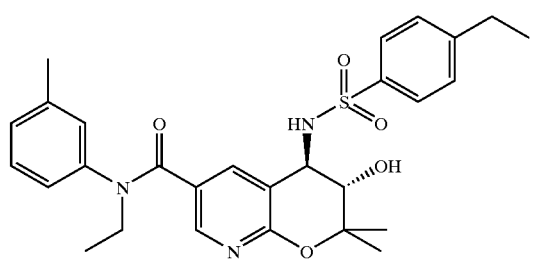
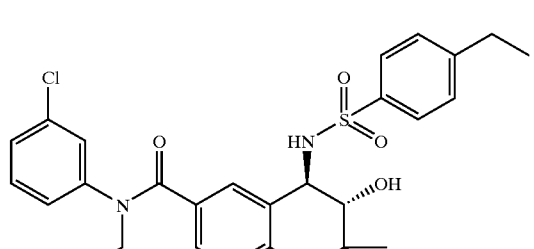
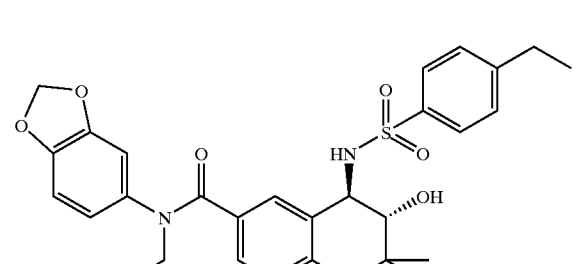
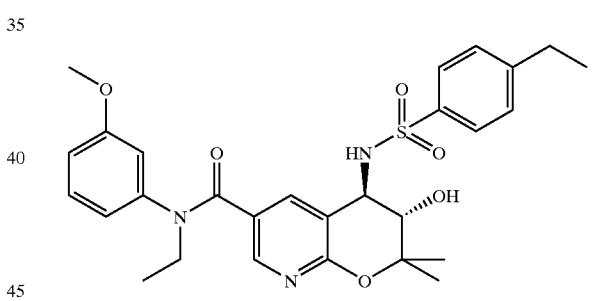
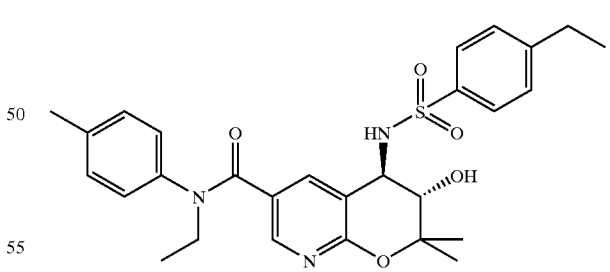
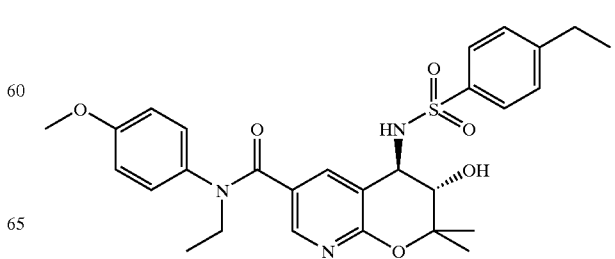

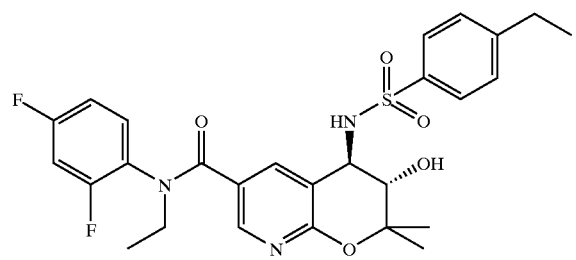
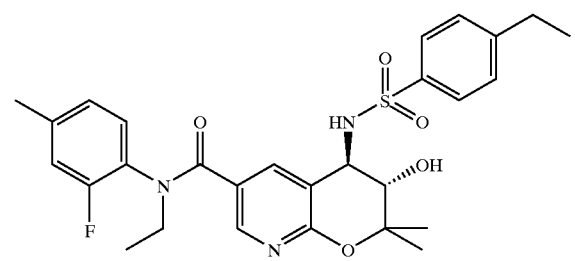
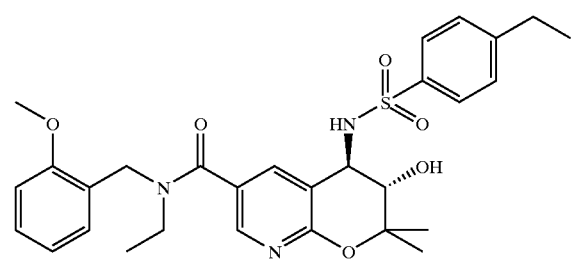
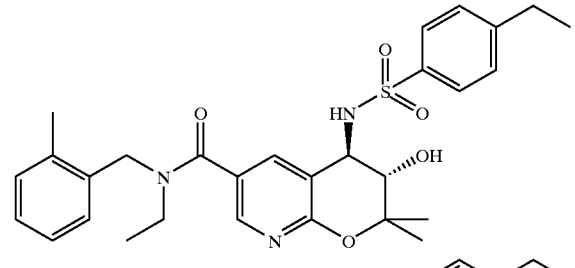
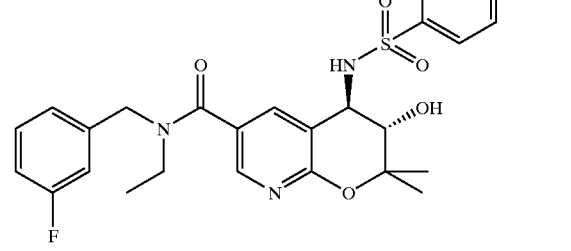
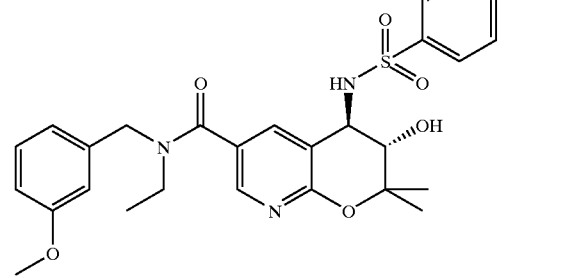
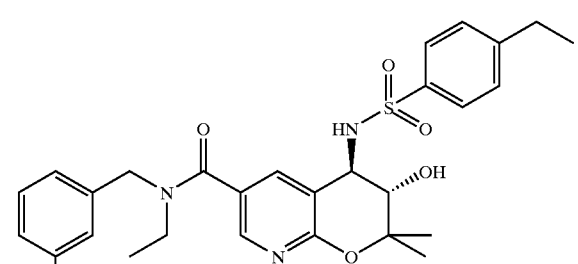
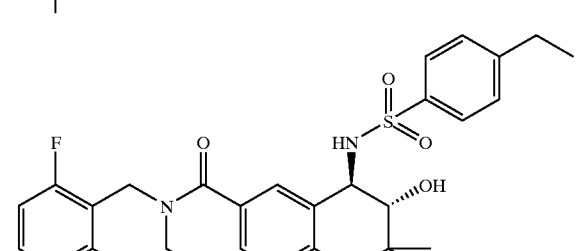
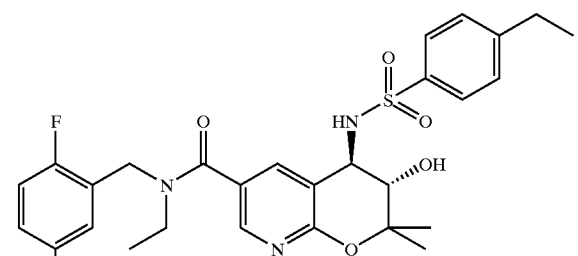
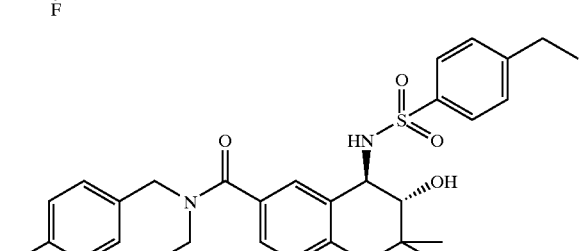
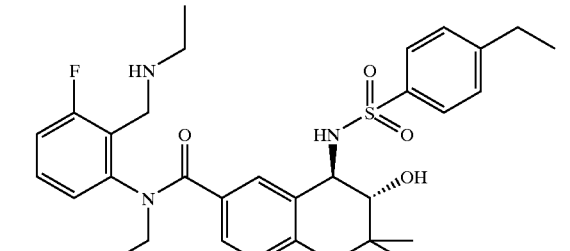
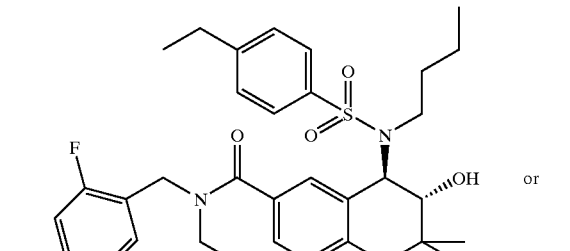
or

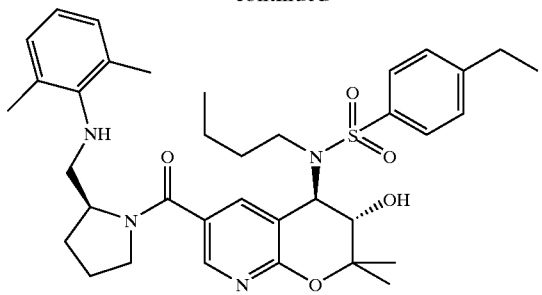

10. A pharmaceutical composition comprising a compound as defined in claim 1 and a pharmaceutically acceptable carrier therefor.

11. A method for preventing or treating cardiac arrhythmia or atrial arrhythmia, which comprises administering to a mammalian species in need of treatment a therapeutically effective amount of a compound which has the structure

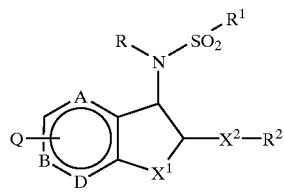

or pharmaceutically acceptable salts thereof, prodrug esters thereof, or all stereoisomers thereof, wherein A and B are CH and D is N;

$X^1$ is
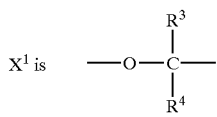

wherein the heteroatom is linked to the aromatic ring; (where $R^3$ and $R^4$ are independently H, alkyl, arylalkyl or cycloalkyl, or $R^3$ and $R^4$ can be taken together with the carbon to which they are attached to form a 5 to 8 carbon containing ring);

R is H, alkyl, alkenyl, aryl, arylalkyl, heterocycloalkyl, cycloalkyl, or cycloalkylalkyl;

$R^1$ is arylalkyl, aryl, alkenyl, heteroaryl, heteroarylalkyl,

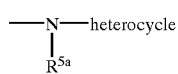

(where $R^{5a}$ is H, alkyl, alkenyl, aryl, arylalkyl, cycloalkyl or cycloalkylalkyl), or

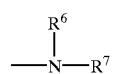

(where $R^6$ and $R^7$ are independently selected from aryl, arylalkyl or cycloalkyl;

$X^2$ is a bond,

or —O— (where $R^8$ is H, alkyl, alkenyl, aryl, arylalkyl, cycloalkyl or cycloalkylalkyl);

$R^2$ is H, alkyl arylalkyl,

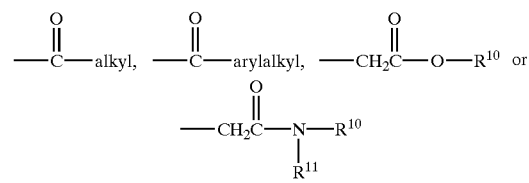

(where $R^{10}$ and $R^{11}$ are independently selected from H, alkyl, arylalkyl or cycloalkyl, or $R^{10}$ and $R^{11}$ can be taken together with the nitrogen to which they are attached to form a 5- to 8-membered ring); and

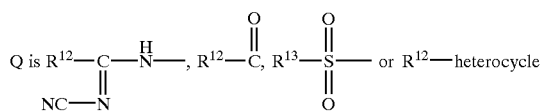

(where $R^{12}$ is alkyl, arylalkyl, aryl

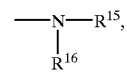

heterocycle, heterocycloalkyl

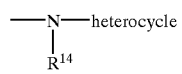

(where $R^{14}$ can be any of the $R^8$ groups), $CF_3$, alkoxy, aryloxy, arylalkoxy, cycloalkyl or cycloalkylalkyl, and where $R^{15}$ and $R^{16}$ are independently selected from H, alkyl, arylalkyl, aryl, heterocyclo, amino, aminoalkyl, cycloalkyl or heterocycloalkyl, or $R^{15}$ and $R^{16}$ can be taken together with the nitrogen to which they are attached to form a 5- to 8-membered ring which may optionally contain an additional nitrogen atom in the ring and/or an amino group or an aminoalkyl group attached to the ring); and $R^{13}$ is

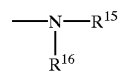

(wherein this moiety is as defined with respect to $R^{12}$).

* * * * *